US007422862B2

(12) United States Patent
Reed et al.

(10) Patent No.: US 7,422,862 B2
(45) Date of Patent: Sep. 9, 2008

(54) METHODS FOR IDENTIFYING MODULATORS OF APOPTOSIS

(75) Inventors: John C Reed, Rancho Santa Fe, CA (US); Bin Guo, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 762 days.

(21) Appl. No.: 10/306,878

(22) Filed: Nov. 27, 2002

(65) Prior Publication Data
US 2003/0175819 A1      Sep. 18, 2003

Related U.S. Application Data

(60) Provisional application No. 60/334,149, filed on Nov. 28, 2001.

(51) Int. Cl.
  *G01N 33/53*   (2006.01)
  *C07K 14/00*   (2006.01)
(52) U.S. Cl. .................. 435/7.8; 435/7.1; 530/325; 530/326; 530/350
(58) Field of Classification Search .............. 435/4; 530/387.1
See application file for complete search history.

(56) References Cited

U.S. PATENT DOCUMENTS

| 4,405,712 | A |  | 9/1983 | Vande Woude et al. |
| 4,650,764 | A |  | 3/1987 | Temin et al. |
| 5,264,563 | A |  | 11/1993 | Huse |
| 5,501,979 | A |  | 3/1996 | Geller et al. |
| 5,506,138 | A |  | 4/1996 | Gelboin et al. |
| 5,561,063 | A |  | 10/1996 | Hock et al. |
| 5,604,090 | A |  | 2/1997 | Alexander et al. |
| 5,674,703 | A |  | 10/1997 | Woo et al. |
| 5,693,508 | A |  | 12/1997 | Chang |
| 5,700,470 | A |  | 12/1997 | Saito et al. |
| 5,719,054 | A |  | 2/1998 | Boursnell et al. |
| 5,731,172 | A |  | 3/1998 | Saito et al. |
| 5,739,018 | A |  | 4/1998 | Miyanohara et al. |
| 6,130,317 | A |  | 10/2000 | Reed et al. |
| 6,165,732 | A |  | 12/2000 | Korsmeyer et al. |
| 6,245,885 | B1 |  | 6/2001 | Shore et al. |
| 2003/0105000 | A1 | * | 6/2003 | Pero et al. ........... 514/12 |
| 2003/0176671 | A1 | * | 9/2003 | Reed et al. .......... 536/23.1 |

FOREIGN PATENT DOCUMENTS

EP           1 221 480 A1  * 10/2002
WO     WO 01/21787 A1   *  3/2001

OTHER PUBLICATIONS

Niikura et al. "Humanin", 2004, Molecular Neurobiology 30(3):327-340.*
Bowie et al (Science, 1990, 247:1306-1310).*
Burgess et al (J of Cell Bio. 111:2129-2138, 1990).*
Lazar et al (Molecular and Cellular Biology, 1988, 8:1247-1252).*
Bowie et al (Science, 1990, 257:1306-1310).*
Scott et al (Nature Genetics, 1999, 21:440-443).*
Bork (Genome Research, 2000, 10:398-400).*
Day et al. (Mol. Endo. 2005 19:1675-1686).*
Alouani, "Scintillation proximity binding assay," *Methods Mol. Biol.* 138:135-41 (2000).
Altschul et al., "Basic local alignment search tool," *J Mol Biol.* 215:403-10 (1990).
Bauminger and Wilchek, "The use of carbodiimides in the preparation of immunizing conjugates," *Methods in Enzymology* 70:151-9 (1980).
Chen and Shapiro, "Affinity NMR," *Anal Chem.* 71:669A-675A (1999).
Cherfils et al., "Protein-protein recognition analyzed by docking simulation," *Proteins* 11:271-80 (1991).
Chou et al., "Solution structure of BID, an intracellular amplifier of apoptotic signaling," *Cell* 96:615-24 (1999).
Degterev et al., "Identification of small-molecule inhibitors of interaction between the BH3 domain and Bcl-xL," *Nat. Cell Biol.* 3:173-182 (2001).
Deutscher, "Setting up a laboratory," *Methods Enzymol.* 182:19-23 (1990).
Eckert et al., "Inhibiting HIV-1 entry: discovery of D-peptide inhibitors that target the gp41 coiled-coil pocket," *Cell* 99:103-115 (1999).
Egleton and Davis, "Bioavailability and transport of peptides and peptide drugs into the brain," *Peptides* 18:1431-1439 (1997).
Eichler et al., "Peptide, peptidomimetic, and organic synthetic combinatorial libraries," *Med. Res. Rev.* 15:481-496 (1995).
Elbashir et al., "Duplexes of 21-nucleotide RNAs mediate RNA interference in cultured mammalian cells," *Nature* 411:494-498 (2001).
Fancy, "Elucidation of protein-protein interactions using chemical cross-linking or label transfer techniques," *Curr Opin Chem Biol.* 4:28-33 (2000).
Fields and Song, "A novel genetic system to detect protein-protein interactions," *Nature* 340:245-246 (1989).
Francis et al., "Combinatorial libraries of transition-metal complexes, catalysts and materials," *Curr. Opin. Chem. Biol.* 2:422-428 (1998).
Galfre and Milstein, "Preparation of monoclonal antibodies: strategies and procedures," *Methods Enzymol.* 73:3-46 (1981).

(Continued)

*Primary Examiner*—Karen A. Canella
*Assistant Examiner*—Peter J Reddig
(74) *Attorney, Agent, or Firm*—McDermott Will & Emery LLP

(57) ABSTRACT

The invention provides a method of identifying an effective compound that modulates the binding of Humanin to Bax or Bid. The invention also provides a method of identifying an effective compound that modulates an activity of Bax or Bid. In addition, the invention provides a method of identifying a Humanin-like compound that binds to Bax or Bid or modulates an activity of Bax or Bid, or inhibits the apoptotic activity of Bax or Bid. The invention further provides an isolated polypeptide containing a mitochondrial-derived form of Humanin (SEQ ID NO:3) or a functional fragment thereof where the fragment contains the methionine at position 16 of SEQ ID NO:3.

13 Claims, 8 Drawing Sheets

OTHER PUBLICATIONS

Gallop et al., "Applications of combinatorial technologies to drug discovery. 1. Background and peptide combinatorial libraries," *J. Med. Chem.* 37:1233-51 (1994).

Gervais et al., "Involvement of caspases in proteolytic cleavage of Alzheimer's amyloid-beta precursor protein and amyloidogenic A beta peptide formation," *Cell* 97:395-406 (1999).

Gordon et al., "Applications of combinatorial technologies to drug discovery. 2. Combinatorial organic synthesis, library screening strategies, and future directions," *J. Med. Chem.* 37:1385-1401 (1994).

Gossen and Bujard, "Tight control of gene expression in mammalian cells by tetracycline-responsive promoters," *Proc. Natl. Acad. Sci. USA* 89:5547-5551 (1992).

Gossen et al., "Transcriptional activation by tetracyclines in mammalian cells," *Science* 268:1766-1769 (1995).

Hajduk et al., "High-throughput nuclear magnetic resonance-based screening," *J. Med. Chem.* 42:2315-2317 (1999).

Hashimoto et al., "A rescue factor abolishing neuronal cell death by a wide spectrum of familial Alzheimer's disease genes and Aβ" *PNAS* 98:6336-6341 (2001).

Hengartner, "The biochemistry of apoptosis," *Nature* 407:770-776 (2000).

Horwell, "The 'peptoid' approach to the design of non-peptide, small molecule agonists and antagonists of neuropeptides," *Trends Biotechnol.* 13:132-134 (1995).

Huse et al., "Generation of a large combinatorial library of the immunoglobulin repertoire in phage lambda," *Science* 246:1275-1281 (1989).

Ikeda et al., "Gd-enhanced dynamic magnetic resonance imaging of breast masses," *Top Magn. Reson. Imaging* 10:143-151 (1999).

Jayasena, "Aptamers: An emerging class of molecules that rival antibodies in diagnostics," *Clinical Chemistry* 45:1628-1650 (1999).

Jin and Reed, "Yeast and apoptosis," *Nat. Rev. Mol. Cell Biol.* 3:453-459 (2002).

Jürgensmeier et al., "Bax directly induces release of cytochrome *c* from isolated mitochondria," *Proc. Natl. Acad. Sci. USA* 95:4997-5002 (1998).

Kermer et al., "Bag1 is a regulator and marker of neuronal differentiation," *Cell Death Differ.* 9:405-413 (2002).

Lau et al., "Conjugation of doxorubicin to monoclonal anti-carcinoembryonic antigen antibody via novel thiol-directed cross-linking reagents," *Bioorg. Med. Chem.* 3:1299-1304 (1995).

Leblanc et al., Caspase-6 role in apoptosis of human neurons, amyloidogenesis, and Alzheimer's disease, *The Journal of Biological Chemistry* 274:23426-23436 (1999).

Lee et al., "Glucocorticoids regulate expression of dihydrofolate reductase cDNA in mouse mammary tumour virus chimaeric plasmids," *Nature* 294:228-232 (1981).

Lengauer and Rarey, "Computational methods for biomolecular docking," *Curr. Opin. Struct. Biol.* 6:402-406 (1996).

Lipton and Rosenberg, "Excitatory amino acids as a final common pathway for neurologic disorders," *N. Engl. J. Med.* 330:613-622 (1994).

Loo et al., "Application of mass spectrometry for target identification and characterization," *Med. Res. Rev.* 19:307-319 (1999).

Martin et al., "Mechanisms for neuronal degeneration in amyotrophic lateral sclerosis and in models of motor neuron death," *Int. J. Mol. Med.* 5:3-13 (2000).

Martin, "Neuronal death in amyotrophic lateral sclerosis is apoptosis: possible contribution of a programmed cell death mechanism," *J. Neuropathol. Exp. Neurol.* 58:459-471 (1999).

McDonnell et al., "Solution structure of the proapoptotic molecule BID: a structural basis for apoptotic agonists and antagonists," *Cell* 96:625-634 (1999).

McLafferty et al., "Techview: biochemistry. Biomolecule mass spectrometry," *Science* 284:1289-1290 (1999).

Mendelsohn and Brent, "Applications of interaction traps/two-hybrid systems to biotechnology research," *Curr. Opin. Biotechnol.* 5:482-486 (1994).

Monot et al., "Representation of affinity in the case of co-operativity in protein ligand binding," *Fundam. Clin. Pharmacol.* 8:18-25 (1994).

Montal and Mueller, "Formation of bimolecular membranes from lipid monolayers and a study of their electrical properties," *Proc. Nat. Acad. Sci. USA* 69:3561-3566 (1972).

Nechushtan et al., "Conformation of the Bax C-terminus regulates subcellar location and cell death," *EMBO J.* 18:2330-2341.

No et al., "Ecdysone-inducible gene expression in mammalian cells and transgenic mice," *Proc. Natl. Acad. Sci. USA* 93:3346-3351 (1996).

Oltvai et al., "Bcl-2 heterodimerizes in vivo with a conserved homolog, Bax, that accelerates programmed cell death," *Cell* 74:609-619 (1993).

Osawa et al., "Recent evidence for evolution of the genetic code," *Microbiological Reviews* 56:229-264 (1992).

Palma et al., "BiGGER: a new (soft) docking algorithm for predicting protein interactions," *Proteins* 39:372-384 (2000).

Parker and Tofts, "Pharmacokinetic analysis of neoplasms using contrast-enhanced dynamic magnetic resonance imaging," 10:130-142 (1999).

Pervushin et al., "Attenuated $T_2$ relaxation by mutual cancellation of dipole-dipole coupling and chemical shift anisotropy indicates an avenue to NMR structures of very large biological macromolecules in solution," *Proc. Natl. Acad. Sci. USA* 94:12366-12371 (1997).

Reed et al., "Structure-function analysis of Bcl-2 family proteins. Regulators of programmed cell death," *Adv. Exp. Med. Biol.* 406:99-112 (1996). (Abstract Only).

Rowland et al., "Preclinical investigation of the antitumour effects of anti-CD19-idarubicin immunoconjugates," *Cancer Immunol. Immunother.* 37:195-202 (1993).

Schendel et al., "Channel formation by antiapoptotic protein Bcl-2," *Proc. Natl. Acad. Sci. USA* 94:5113-5118 (1997).

Schendel et al., "Ion channel activity of the BH3 only Bcl-2 family member, BID," *J. Biol. Chem.* 274:21932-21936 (1999).

Schutz, "The pharmacological basis of receptor binding," *Wien. Klin. Wochenschr.* 103:438-442 (1991). (Abstract Only).

Shih et al., "Internalization of an intact doxorubicin immunoconjugate," *Cancer Immunol. Immunother.* 38:92-98 (1994).

Shoichet and Kuntz, "Protein docking and complementarity," *J. Mol. Biol.* 221:327-346 (1991).

Shuker et al., "Discovering high-affinity ligands for proteins: SAR by NMR," *Science* 274:1531-1534 (1996).

Sivam et al., "Therapeutic efficacy of a doxorubicin immunoconjugate in a preclinical model of spontaneous metastatic human melanoma," *Cancer Res.* 55:2352-2356 (1995).

Sofia, "Carbohydrate-based combinatorial libraries," *Mol. Divers.* 3:75-94 (1997-1998).

Stanfield et al., "Dual conformations for the HIV-1 gp120 V3 loop in complexes with different neutralizing fabs," *Structure Fold. Des.* 7:131-142 (1999).

Stubbs, "Application of magnetic resonance techniques for imaging tumour physiology," *Acta. Oncol.* 38:845-853 (1999).

Suzuki et al., "Structure of Bax: coregulation of dimer formation and intracellular localization," *Cell* 103:645-654 (2000).

Tajima et al., "Evidence for in vivo production of Humanin peptide, a neuroprotective factor against Alzheimer's disease-related insults," *Neurosci. Lett.* 324:227-231 (2002).

Tietze and Lieb, "Domino reactions for lib„,rary synthesis of small molecules in combinatorial chemistry," *Curr. Opin Chem. Biol.* 2:363-371 (1998).

Uetsuki et al., "Activation of neuronal caspase-3 by intracellular accumulation of wild-type Alzheimer amyloid precursor protein," *The Journal of Neuroscience* 19:6955-6964 (1999).

Wang et al., "BID: A novel BH3 domain-only death agonist," *Genes Dev.* 10:2859-2869 (1996).

Ward et al., "Binding activities of a repertoire of single immunoglobulin variable domains secreted from *Escherichia coli.*," *Nature* 341:544-546 (1989).

Wei et al., "Proapoptotic BAX and BAK; a requisite gateway to mitochondrial dysfunction and death," *Science* 292:727-730 (2001).

Winter and Harris, "Humanized antibodies," *Immunol. Today* 14:243-246 (1993).

Yao et al., "Functional ecdysone receptor is the product of EcR and Ultraspiracle genes," *Nature* 366:476-479 (1993).

Zelphati et al., "Intracellular delivery of proteins with a new lipid-mediated delivery system," *The Journal of Biological Chemistry* 276:35103-35110 (2001).

Zha et al., "Structure-function comparison of the proapoptotic protein Bax in yeast and mammalian cells," *Molecular and Cellular Biology* 16:6494-6508 (1996).

Zhang et al., "Role of BAX in the apoptotic response to anticancer agents," *Science* 290:989-992 (2000).

Hashimoto et al., "Mechanisms of neuroprotection by a novel rescue humanin from Swedish mutant amyloid precursor protein," *Biochem. Biophys. Res. Commun.* 283:460-468 (2001).

Leonard et al., "Bid regulation of neuronal apoptosis," *Brain Res. Dev. Brain Res.* 128:187-190 (2001).

Reed, J., "Double identity for proteins of the Bcl-2 family," *Nature* 387:773-776 (1997).

Satterthwait et al., "Conformational restriction of peptidyl immunogens with covalent replacements for the hydrogen bond," *Vaccine* 6:99-103 (1988).

Xu and Reed, "Bax inhibitor-1, a mammalian apoptosis suppressor identified by functional screening in yeast," *Mol. Cell.* 1:337-346 (1998).

Yin, XM, "Signal transduction mediated by Bid, a pro-death Bcl-2 family proteins, connects the death receptor and mitochondria apoptosis pathways," *Cell. Res.* 10:161-167 (2000).

Yin, XM, "Bid, a critical mediator for apoptosis induced by the activation of R1 death receptors in hepatocytes," *J. Mol. Med.* 78:203-211 (2000).

Zamzami et al., "Bid acts on the permeability transition pore complex to induce apoptosis," *Oncogene* 19:6342-6350 (2000).

\* cited by examiner

A

Human Mitochondrion Genome

GenBank AF346981

B

MAPRGFSCLLLLTSEIDLPVKRRA  SEQ ID NO: 2

MAPRGFSCLLLLTSEMDLPVK  SEQ ID NO: 3

C

```
                        SEQUENCE LISTING

<160> NUMBER OF SEQ ID NOS: 28

<210> SEQ ID NO 1
<211> LENGTH: 75
<212> TYPE: DNA
<213> ORGANISM: Homo sapiens
<220> FEATURE:
<221> NAME/KEY: CDS
<222> LOCATION: (1)...(75)

<400> SEQUENCE: 1 atg gct cca cga ggg ttc agc tgt ctc tta ctt tta acc agt gaa att    48
Met Ala Pro Arg Gly Phe Ser Cys Leu Leu Leu Leu Thr Ser Glu Ile
 1               5                  10                  15 gac ctg ccc gtg aag agg cgg gca taa                                75
Asp Leu Pro Val Lys Arg Arg Ala  *
                20

<210> SEQ ID NO 2
<211> LENGTH: 24
<212> TYPE: PRT
<213> ORGANISM: Homo sapiens

<400> SEQUENCE: 2

Met Ala Pro Arg Gly Phe Ser Cys Leu Leu Leu Leu Thr Ser Glu Ile
 1               5                  10                  15

Asp Leu Pro Val Lys Arg Arg Ala
                20

<210> SEQ ID NO 3
<211> LENGTH: 21
<212> TYPE: PRT
<213> ORGANISM: Homo sapiens

<400> SEQUENCE: 3

Met Ala Pro Arg Gly Phe Ser Cys Leu Leu Leu Leu Thr Ser Glu Met
 1               5                  10                  15

Asp Leu Pro Val Lys
                20

<210> SEQ ID NO 4
<211> LENGTH: 579
<212> TYPE: DNA
<213> ORGANISM: Homo sapiens
<220> FEATURE:
<221> NAME/KEY: CDS
<222> LOCATION: (1)...(579)

<400> SEQUENCE: 4 atg gac ggg tcc ggg gag cag ccc aga ggc ggg ggg ccc acc agc tct    48
Met Asp Gly Ser Gly Glu Gln Pro Arg Gly Gly Gly Pro Thr Ser Ser
 1               5                  10                  15 gag cag atc atg aag aca ggg gcc ctt ttg ctt cag ggt ttc atc cag    96
Glu Gln Ile Met Lys Thr Gly Ala Leu Leu Gln Gly Phe Ile Gln
                20                  25                  30 gat cga gca ggg cga atg ggg ggg gag gca ccc gag ctg gcc ctg gac   144
Asp Arg Ala Gly Arg Met Gly Gly Glu Ala Pro Glu Leu Ala Leu Asp
            35                  40                  45
```

-continued

```
ccg gtg cct cag gat gcg tcc acc aag aag ctg agc gag tgt ctc aag      192
Pro Val Pro Gln Asp Ala Ser Thr Lys Lys Leu Ser Glu Cys Leu Lys
 50                  55                  60 cgc atc ggg gac gaa ctg gac agt aac atg gag ctg cag agg atg att      240
Arg Ile Gly Asp Glu Leu Asp Ser Asn Met Glu Leu Gln Arg Met Ile
 65                  70                  75                  80 gcc gcc gtg gac aca gac tcc ccc cga gag gtc ttt ttc cga gtg gca      288
Ala Ala Val Asp Thr Asp Ser Pro Arg Glu Val Phe Phe Arg Val Ala
                     85                  90                  95 gct gac atg ttt tct gac ggc aac ttc aac tgg ggc cgg gtt gtc gcc      336
Ala Asp Met Phe Ser Asp Gly Asn Phe Asn Trp Gly Arg Val Val Ala
                100                 105                 110 ctt ttc tac ttt gcc agc aaa ctg gtg ctc aag gcc ctg tgc acc aag      384
Leu Phe Tyr Phe Ala Ser Lys Leu Val Leu Lys Ala Leu Cys Thr Lys
            115                 120                 125 gtg ccg gaa ctg atc aga acc atc atg ggc tgg aca ttg gac ttc ctc      432
Val Pro Glu Leu Ile Arg Thr Ile Met Gly Trp Thr Leu Asp Phe Leu
130                 135                 140 cgg gag cgg ctg ttg ggc tgg atc caa gac cag ggt ggt tgg gac ggc      480
Arg Glu Arg Leu Leu Gly Trp Ile Gln Asp Gln Gly Gly Trp Asp Gly
145                 150                 155                 160 ctc ctc tcc tac ttt ggg acg ccc acg tgg cag acc gtg acc atc ttt      528
Leu Leu Ser Tyr Phe Gly Thr Pro Thr Trp Gln Thr Val Thr Ile Phe
                165                 170                 175 gtg gcg gga gtg ctc acc gcc tcg ctc acc atc tgg aag aag atg ggc      576
Val Ala Gly Val Leu Thr Ala Ser Leu Thr Ile Trp Lys Lys Met Gly
                180                 185                 190 tga                                                                  579
 *
```

<210> SEQ ID NO 5
<211> LENGTH: 192
<212> TYPE: PRT
<213> ORGANISM: Homo sapiens

<400> SEQUENCE: 5

```
Met Asp Gly Ser Gly Glu Gln Pro Arg Gly Gly Gly Pro Thr Ser Ser
 1               5                   10                  15

Glu Gln Ile Met Lys Thr Gly Ala Leu Leu Leu Gln Gly Phe Ile Gln
                20                  25                  30

Asp Arg Ala Gly Arg Met Gly Gly Glu Ala Pro Glu Leu Ala Leu Asp
            35                  40                  45

Pro Val Pro Gln Asp Ala Ser Thr Lys Lys Leu Ser Glu Cys Leu Lys
 50                  55                  60

Arg Ile Gly Asp Glu Leu Asp Ser Asn Met Glu Leu Gln Arg Met Ile
 65                  70                  75                  80

Ala Ala Val Asp Thr Asp Ser Pro Arg Glu Val Phe Phe Arg Val Ala
                     85                  90                  95

Ala Asp Met Phe Ser Asp Gly Asn Phe Asn Trp Gly Arg Val Val Ala
                100                 105                 110

Leu Phe Tyr Phe Ala Ser Lys Leu Val Leu Lys Ala Leu Cys Thr Lys
            115                 120                 125

Val Pro Glu Leu Ile Arg Thr Ile Met Gly Trp Thr Leu Asp Phe Leu
130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
```

165                 170                 175
Val Ala Gly Val Leu Thr Ala Ser Leu Thr Ile Trp Lys Lys Met Gly
            180                 185                 190

<210> SEQ ID NO 6
<211> LENGTH: 588
<212> TYPE: DNA
<213> ORGANISM: Homo sapiens
<220> FEATURE:
<221> NAME/KEY: CDS
<222> LOCATION: (1)...(585)

<400> SEQUENCE: 6 atg gac tgt gag gtc aac aac ggt tcc agc ctc agg gat gag tgc atc        48
Met Asp Cys Glu Val Asn Asn Gly Ser Ser Leu Arg Asp Glu Cys Ile
1               5                   10                  15 aca aac cta ctg gtg ttt ggc ttc ctc caa agc tgt tct gac aac agc        96
Thr Asn Leu Leu Val Phe Gly Phe Leu Gln Ser Cys Ser Asp Asn Ser
            20                  25                  30 ttc cgc aga gag ctg gac gca ctg ggc cac gag ctg cca gtg ctg gct       144
Phe Arg Arg Glu Leu Asp Ala Leu Gly His Glu Leu Pro Val Leu Ala
        35                  40                  45 ccc cag tgg gag ggc tac gat gag ctg cag act gat ggc aac cgc agc       192
Pro Gln Trp Glu Gly Tyr Asp Glu Leu Gln Thr Asp Gly Asn Arg Ser
    50                  55                  60 agc cac tcc cgc ttg gga aga ata gag gca gat tct gaa agt caa gaa       240
Ser His Ser Arg Leu Gly Arg Ile Glu Ala Asp Ser Glu Ser Gln Glu
65                  70                  75                  80 gac atc atc cgg aat att gcc agg cac ctc gcc cag gtc ggg gac agc       288
Asp Ile Ile Arg Asn Ile Ala Arg His Leu Ala Gln Val Gly Asp Ser
                85                  90                  95 atg gac cgt agc atc cct ccg ggc ctg gtg aac ggc ctg gcc ctg cag       336
Met Asp Arg Ser Ile Pro Pro Gly Leu Val Asn Gly Leu Ala Leu Gln
            100                 105                 110 ctc agg aac acc agc cgg tcg gag gag gac cgg aac agg gac ctg gcc       384
Leu Arg Asn Thr Ser Arg Ser Glu Glu Asp Arg Asn Arg Asp Leu Ala
        115                 120                 125 act gcc ctg gag cag ctg ctg cag gcc tac cct aga gac atg gag aag       432
Thr Ala Leu Glu Gln Leu Leu Gln Ala Tyr Pro Arg Asp Met Glu Lys
    130                 135                 140 gag aag acc atg ctg gtg ctg gcc ctg ctg ctg gcc aag aag gtg gcc       480
Glu Lys Thr Met Leu Val Leu Ala Leu Leu Leu Ala Lys Lys Val Ala
145                 150                 155                 160 agt cac acg ccg tcc ttg ctc cgt gat gtc ttt cac aca aca gtg aat       528
Ser His Thr Pro Ser Leu Leu Arg Asp Val Phe His Thr Thr Val Asn
                165                 170                 175 ttt att aac cag aac cta cgc acc tac gtg agg agc tta gcc aga aat       576
Phe Ile Asn Gln Asn Leu Arg Thr Tyr Val Arg Ser Leu Ala Arg Asn
            180                 185                 190 ggg atg gac tga                                                        588
Gly Met Asp
        195

<210> SEQ ID NO 7
<211> LENGTH: 195
<212> TYPE: PRT
<213> ORGANISM: Homo sapiens

<400> SEQUENCE: 7

Met Asp Cys Glu Val Asn Asn Gly Ser Ser Leu Arg Asp Glu Cys Ile
1               5                   10                  15

-continued

```
        Thr Asn Leu Leu Val Phe Gly Phe Leu Gln Ser Cys Ser Asp Asn Ser
                     20                  25                  30

Phe Arg Arg Glu Leu Asp Ala Leu Gly His Glu Leu Pro Val Leu Ala
                         35                  40                  45

Pro Gln Trp Glu Gly Tyr Asp Glu Leu Gln Thr Asp Gly Asn Arg Ser
                     50                  55                  60

Ser His Ser Arg Leu Gly Arg Ile Glu Ala Asp Ser Glu Ser Gln Glu
        65                  70                  75                  80

Asp Ile Ile Arg Asn Ile Ala Arg His Leu Ala Gln Val Gly Asp Ser
                             85                  90                  95

Met Asp Arg Ser Ile Pro Pro Gly Leu Val Asn Gly Leu Ala Leu Gln
                        100                 105                 110

Leu Arg Asn Thr Ser Arg Ser Glu Glu Asp Arg Asn Arg Asp Leu Ala
                    115                 120                 125

Thr Ala Leu Glu Gln Leu Leu Gln Ala Tyr Pro Arg Asp Met Glu Lys
                130                 135                 140

Glu Lys Thr Met Leu Val Leu Ala Leu Leu Ala Lys Lys Val Ala
        145                 150                 155                 160

Ser His Thr Pro Ser Leu Leu Arg Asp Val Phe His Thr Thr Val Asn
                            165                 170                 175

Phe Ile Asn Gln Asn Leu Arg Thr Tyr Val Arg Ser Leu Ala Arg Asn
                        180                 185                 190

Gly Met Asp
                195

<210> SEQ ID NO 8
<211> LENGTH: 408
<212> TYPE: DNA
<213> ORGANISM: Homo sapiens
<220> FEATURE:
<221> NAME/KEY: CDS
<222> LOCATION: (1)...(408)

<400> SEQUENCE: 8 ggc aac cgc agc agc cac tcc cgc ttg gga aga ata gag gca gat tct        48
Gly Asn Arg Ser Ser His Ser Arg Leu Gly Arg Ile Glu Ala Asp Ser
 1               5                  10                  15 gaa agt caa gaa gac atc atc cgg aat att gcc agg cac ctc gcc cag       96
Glu Ser Gln Glu Asp Ile Ile Arg Asn Ile Ala Arg His Leu Ala Gln
             20                  25                  30 gtc ggg gac agc atg gac cgt agc atc cct ccg ggc ctg gtg aac ggc      144
Val Gly Asp Ser Met Asp Arg Ser Ile Pro Pro Gly Leu Val Asn Gly
         35                  40                  45 ctg gcc ctg cag ctc agg aac acc agc cgg tcg gag gag gac cgg aac      192
Leu Ala Leu Gln Leu Arg Asn Thr Ser Arg Ser Glu Glu Asp Arg Asn
     50                  55                  60 agg gac ctg gcc act gcc ctg gag cag ctg ctg cag gcc tac cct aga      240
Arg Asp Leu Ala Thr Ala Leu Glu Gln Leu Leu Gln Ala Tyr Pro Arg
 65                  70                  75                  80 gac atg gag aag gag aag acc atg ctg gtg ctg gcc ctg ctg ctg gcc      288
Asp Met Glu Lys Glu Lys Thr Met Leu Val Leu Ala Leu Leu Leu Ala
                 85                  90                  95 aag aag gtg gcc agt cac acg ccg tcc ttg ctc cgt gat gtc ttt cac      336
Lys Lys Val Ala Ser His Thr Pro Ser Leu Leu Arg Asp Val Phe His
            100                 105                 110 aca aca gtg aat ttt att aac cag aac cta cgc acc tac gtg agg agc      384
Thr Thr Val Asn Phe Ile Asn Gln Asn Leu Arg Thr Tyr Val Arg Ser
        115                 120                 125
```

```
                tta gcc aga aat ggg atg gac tga                            408
                Leu Ala Arg Asn Gly Met Asp *
                    130                 135
```

<210> SEQ ID NO 9
<211> LENGTH: 135
<212> TYPE: PRT
<213> ORGANISM: Homo sapiens

<400> SEQUENCE: 9

```
Gly Asn Arg Ser Ser His Ser Arg Leu Gly Arg Ile Glu Ala Asp Ser
  1               5                  10                  15

Glu Ser Gln Glu Asp Ile Ile Arg Asn Ile Ala Arg His Leu Ala Gln
             20                  25                  30

Val Gly Asp Ser Met Asp Arg Ser Ile Pro Pro Gly Leu Val Asn Gly
         35                  40                  45

Leu Ala Leu Gln Leu Arg Asn Thr Ser Arg Ser Glu Glu Asp Arg Asn
     50                  55                  60

Arg Asp Leu Ala Thr Ala Leu Glu Gln Leu Leu Gln Ala Tyr Pro Arg
 65                  70                  75                  80

Asp Met Glu Lys Glu Lys Thr Met Leu Val Leu Ala Leu Leu Leu Ala
                 85                  90                  95

Lys Lys Val Ala Ser His Thr Pro Ser Leu Leu Arg Asp Val Phe His
            100                 105                 110

Thr Thr Val Asn Phe Ile Asn Gln Asn Leu Arg Thr Tyr Val Arg Ser
        115                 120                 125

Leu Ala Arg Asn Gly Met Asp
    130                 135
```

<210> SEQ ID NO 10
<211> LENGTH: 7
<212> TYPE: PRT
<213> ORGANISM: Artificial Sequence
<220> FEATURE:
<223> OTHER INFORMATION: Synthetic construct

<400> SEQUENCE: 10

```
Pro Lys Lys Lys Arg Lys Val
  1               5
```

<210> SEQ ID NO 11
<211> LENGTH: 9
<212> TYPE: PRT
<213> ORGANISM: Artificial Sequence
<220> FEATURE:
<223> OTHER INFORMATION: Synthetic construct

<400> SEQUENCE: 11

```
Cys Asn Ser Arg Leu His Leu Arg Cys
  1               5
```

<210> SEQ ID NO 12
<211> LENGTH: 9
<212> TYPE: PRT
<213> ORGANISM: Artificial Sequence
<220> FEATURE:
<223> OTHER INFORMATION: Synthetic construct

<400> SEQUENCE: 12

```
Val Leu Arg Glu Gly Pro Ala Gly Gly
  1               5
```

```
<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
cctcattgta cccattctaa tcgc                                              24

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
gtagaagagc gatggtgaga gc                                                22

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ctccctctct cctactcctg ctcg                                              24

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
ggtatagaat ggggtctcct cctcc                                             25

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
atggctccac gagggttc                                                     18

<210> SEQ ID NO 18
<211> LENGTH: 18
<212> TYPE: DNA
<213> ORGANISM: Artificial Sequence
<220> FEATURE:
<223> OTHER INFORMATION: Primer

<400> SEQUENCE: 18
ttatgcccgc ctcttcac                                                     18

<210> SEQ ID NO 19
<211> LENGTH: 15
<212> TYPE: DNA
<213> ORGANISM: Artificial Sequence
<220> FEATURE:
<223> OTHER INFORMATION: Primer
```

```
<400> SEQUENCE: 19
atggacgggt ccggg                                                        15

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
tcagcccatc ttcttccag                                                    19

<210> SEQ ID NO 21
<211> LENGTH: 26
<212> TYPE: DNA
<213> ORGANISM: Artificial Sequence
<220> FEATURE:
<223> OTHER INFORMATION: Primer

<400> SEQUENCE: 21
ggctcgagat ggctccacga gggttc                                            26

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
ggaagcttac ttcacgggca ggtccatttc                                        30

<210> SEQ ID NO 23
<211> LENGTH: 35
<212> TYPE: DNA
<213> ORGANISM: Artificial Sequence
<220> FEATURE:
<223> OTHER INFORMATION: Primer

<400> SEQUENCE: 23
ggctcgagga atggctccac gagggttcag cgctc                                  35

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
ggaagctttt atgcccgcct cttcac                                            26

<210> SEQ ID NO 25
<211> LENGTH: 21
<212> TYPE: RNA
<213> ORGANISM: Artificial Sequence
<220> FEATURE:
<223> OTHER INFORMATION: synthetic construct of RNA and DNA
      oligonucleotide
<220> FEATURE:
<221> NAME/KEY: misc_feature
<222> LOCATION: (1)...(19)
<223> OTHER INFORMATION: ribonucleotide
<220> FEATURE:
<221> NAME/KEY: misc_feature
<222> LOCATION: (20)...(21)
```

-continued

```
<223> OTHER INFORMATION: n = deoxyribonucleotide thymine

<400> SEQUENCE: 25
ccagugaaau ugaccugccn n                                              21

<210> SEQ ID NO 26
<211> LENGTH: 21
<212> TYPE: RNA
<213> ORGANISM: Artificial Sequence
<220> FEATURE:
<223> OTHER INFORMATION: synthetic construct of RNA and DNA
      oligonucleotide
<220> FEATURE:
<221> NAME/KEY: misc_feature
<222> LOCATION: (1)...(19)
<223> OTHER INFORMATION: ribonucleotide
<220> FEATURE:
<221> NAME/KEY: misc_feature
<222> LOCATION: (20)...(21)
<223> OTHER INFORMATION: n = deoxyribonucleotide thymine

<400> SEQUENCE: 26
ggcaggucaa uuucacuggn n                                              21

<210> SEQ ID NO 27
<211> LENGTH: 21
<212> TYPE: RNA
<213> ORGANISM: Artificial Sequence
<220> FEATURE:
<223> OTHER INFORMATION: synthetic construct of RNA and DNA
      oligonucleotide
<220> FEATURE:
<221> NAME/KEY: misc_feature
<222> LOCATION: (1)...(19)
<223> OTHER INFORMATION: ribonucleotide
<220> FEATURE:
<221> NAME/KEY: misc_feature
<222> LOCATION: (20)...(21)
<223> OTHER INFORMATION: n= deoxyribonucleotide thymine

<400> SEQUENCE: 27
ccgaugaaau ugaccugccn n                                              21

<210> SEQ ID NO 28
<211> LENGTH: 21
<212> TYPE: RNA
<213> ORGANISM: Artificial Sequence
<220> FEATURE:
<223> OTHER INFORMATION: synthetic construct of RNA and DNA
      oligonucleotide
<220> FEATURE:
<221> NAME/KEY: misc_feature
<222> LOCATION: (1)...(19)
<223> OTHER INFORMATION: ribonucleotide
<220> FEATURE:
<221> NAME/KEY: misc_feature
<222> LOCATION: (20)...(21)
<223> OTHER INFORMATION: n = deoxyribonucleotide thymine

<400> SEQUENCE: 28
ggcaggucaa uuucaucggn n                                              21
```

METHODS FOR IDENTIFYING MODULATORS OF APOPTOSIS

This application claims benefit of the filing date of U.S. Provisional Application No. 60/334,149, filed Nov. 28, 2001, and which is incorporated herein by reference.

This invention was made with government support under grant number GM60554 awarded by the National Institutes of Health. The United States Government has certain rights in this invention.

BACKGROUND OF THE INVENTION

This invention relates generally to the fields of molecular biology and molecular medicine and more specifically to polypeptides involved in the regulation of neuronal apoptotic cell death.

Apoptosis is the term used to describe a type of cellular death that occurs in many tissues as a normal physiological process. This form of cellular demise involves the activation of a built-in genetic program for cell suicide by which cells essentially autodigest. The remnants of these dead cells are then cleared by neighboring phagocytic cells, without resulting in inflammation or scarring. Apoptosis thus stands in marked contrast to cell death caused, for example, by oxygen-deprivation in the settings of myocardial infarction or stroke, where cells lose their energy supplies, rupture and spill their contents into the extracellular milieu. This type of cell death or necrosis often results in inflammation and undesirable consequences.

Apoptosis is required for normal tissue turnover, for the proper development and maintenance of the immune system, for the development of the nervous system, and for the elimination of virus-infected cells. It is a well-ordered process that is characterized by DNA fragmentation, chromatin condensation, membrane blebbing and cell shrinkage. Cells undergoing apoptosis ultimately disassemble into membrane-enclosed vesicles (apoptotic bodies) that are engulfed by neighboring cells and phagocytes, thus preventing an inflammatory response. In addition, apoptosis can be induced to occur by cellular, hormonal or other stimuli to remove unwanted cells from the body. For example, apoptosis occurs in the female reproductive tissues with each menstrual cycle via loss of hormonal stimulation in the absence of a successful pregnancy.

In contrast to the effect of apoptosis in normal cellular processes, when aberrantly regulated, the death of cells through apoptosis can lead to a variety of disease states and pathological conditions. For example, the death of neurons that occurs in diseases such as Alzheimer's dementia and Parkinson's disease shows many hallmarks of apoptosis. Additionally, cell death caused by viral infection can occur through apoptosis in many cases, including T-cell death induced by the human immunodeficiency virus (HIV). Autoimmune diseases, where immune cells inappropriately attack normal tissues, is due, in part, to a failure of apoptosis to occur. In addition, a lack of apoptosis can also play a role in tumorigenesis.

In the nervous system, apoptosis is normally involved in the loss of redundant neurons during fetal development. However, the dysregulation of apoptosis in the nervous system can result in unintended neuronal cell death and can be involved in neurodegenerative diseases such as Alzheimer's disease, Parkinson's disease and Amyotrophic Lateral Sclerosis (ALS). Alzheimer's disease is the most common form of dementia and the fourth leading cause of deaths in adults after heart disease, cancer and stroke. It is estimated that one in ten Americans over the age of 65, and nearly one half of those over the age of 85, have Alzheimer's disease. Amyloid b-protein (ABP) has been identified as a possible causative agent of this disease. Addition of ABP, or of specific fragments of this polypeptide, to cultured neurons and neuronal cell lines results in cell death. Expression of Bcl-2 in these cultured cells can reduce neuronal cell death induced by ABP indicating that apoptosis can contribute to neuronal cell death in Alzheimer's disease. Currently there are no biological screening procedures or effective treatments that can stop the progression of Alzheimer's disease.

Thus there exists a need to identify polypeptide interactions that regulate apoptosis and identify compounds that bind to these polypeptides or modulate the interaction of these polypeptides. The present invention satisfies this need and provides related advantages as well.

SUMMARY OF THE INVENTION

The invention provides a method of identifying an effective compound that modulates the binding of Humanin to Bax, by: (a) contacting Humanin with Bax under conditions suitable to form a Humanin-Bax complex; (b) contacting the Humanin-Bax complex with a candidate compound; and (c) determining the ability of the candidate compound to modulate the binding of Humanin to Bax, where modulation of the binding of Humanin to Bax indicates that the candidate compound is an effective compound that modulates the binding of Humanin to Bax.

The invention also provides a method of identifying an effective compound that modulates an activity of Bax, by: (a) contacting Humanin with Bax under conditions suitable to form a Humanin-Bax complex; (b) measuring an activity of Bax; (c) contacting the Humanin-Bax complex with a candidate compound; (d) determining the amount of activity of Bax in the presence of the candidate compound; and (e) comparing the amount of activity from step (b) with the amount of activity from step (d), where modulation of an activity of Bax indicates that the candidate compound is an effective compound that modulates an activity of Bax.

The invention also provides a method of identifying an effective compound that modulates the binding of Humanin to Bid, by: (a) contacting Humanin with Bid under conditions suitable to form a Humanin-Bid complex; (b) contacting the Humanin-Bid complex with a candidate compound; and (c) determining the ability of the candidate compound to modulate the binding of Humanin to Bid, where modulation of the binding of Humanin to Bid indicates that the candidate compound is an effective compound that modulates the binding of Humanin to Bid.

The invention also provides a method of identifying an effective compound that modulates an activity of Bid, by: (a) contacting Humanin with Bid under conditions suitable to form a Humanin-Bid complex; (b) measuring an activity of Bid; (c) contacting the Humanin-Bid complex with a candidate compound; (d) determining the amount of activity of Bid in the presence of the candidate compound; and (e) comparing the amount of activity from step (b) with the amount of activity from step (d), where modulation of an activity of Bid indicates that the candidate compound is an effective compound that modulates an activity of Bid.

The invention further provides an isolated polypeptide containing the amino acid sequence designated as SEQ ID NO:3, or a functional fragment thereof, where the fragment contains the methionine at position 16 of SEQ ID NO:3.

BRIEF DESCRIPTION OF THE DRAWINGS

FIG. 3A shows the location of Humanin in the human mitochondrial genome. FIG. 3B shows the difference between Humanin translated in the cytosol (SEQ ID NO:2) compared to mitochondria (SEQ ID NO:3), based on differences in the mitochondrial genetic code. Humanin from mitochondria can contain a methionine at position 16 instead of an isoleucine and lack three amino acids at the C-terminus. FIG. 3C shows the results of a reverse transcription polymerase chain reaction assay (RT-PCR) of purified mitochondria RNA isolated from 293T cells. Primers specific for Bax, Humanin, NADH dehydrogenase subunit I, and cytochrome c oxidase subunit I were used, respectively.

DETAILED DESCRIPTION OF THE INVENTION

There are two major apoptotic pathways known in mammalian cells (see Hengatner, M. O., *Nature* 407:770-776). One pathway is through "death receptors" such as CD95 and tumor necrosis factor receptor I at the cell surface. The other pathway is the mitochondrial pathway which is used in response to extracellular cues and internal insults such as DNA damage. In the death receptor pathway, binding of a ligand to a death receptor induces the formation of a death inducing signaling complex which recruits the Fas-associated death domain protein (FADD) and multiple procaspase-8 molecules, resulting in caspase-8 activation through induced proximity. In the mitochondrial pathway, Bcl-2 pro- and anti-apoptotic family member polypeptides in mitochondrial membranes compete to regulate cytochrome c exit. If cyotochrome c is released it can associate with Apaf-1 which in turn binds procaspase-9 to form an apoptosome.

Several polypeptides, including Bcl-2 and Bcl-2 related polypeptides, are known to be involved in the process of apoptosis. The Bcl-2 related family is comprised of well over a dozen polypeptides that have different functions. Bcl-2 was first discovered because of its involvement in B-cell lymphomas in humans. Bcl-2 has been shown to promote cell survival by blocking apoptosis. In contrast, the Bcl-2 related polypeptides Bax and Bid have been shown to promote apoptosis. Bax is a 192 amino acid polypeptide that was first discovered based on its similarity to Bcl-2 (Oltvai et al., *Cell* 74:609-619 (1993)). The ratio of anti-apoptotic Bcl-2 to pro-apoptotic Bax can be used as an indicator of whether a cell will die or survive. Bid is a 195 amino acid polypeptide that is related to Bcl-2, although more distantly than Bax. Bid can act as a point of contact between the death receptor and mitochondrial apoptosis pathways. Bid can be cleaved by caspase-8 into a truncated form, t-Bid, which increases its pro-death activity and results in its translocation to the mitochondria where it promotes cytochrome c exit. Unlike Bcl-2, which is post-translationally inserted into intracellular membranes, Bax and Bid can shuttle between the cytosol and organelles.

Humanin is a recently discovered 24 amino acid polypeptide that is thought to be secreted from the cell (Hashimoto et al., *Proc. Natl. Acad. Sci. USA* 98: 6336-6341 (2001)). Humanin prevents neuronal cell death induced by familial Alzheimer's disease genes and b-amyloid. However, Humanin does not protect cells from death induced by other agents such as Q79 or superoxide dismutase-1 mutants. The mechanism by which Humanin protects neurons from cell death induced by familial Alzheimer's disease genes and b-amyloid is unknown. Furthermore, Humanin has not been reported to bind to, or act on, any other polypeptides within a cell.

Figure 1:
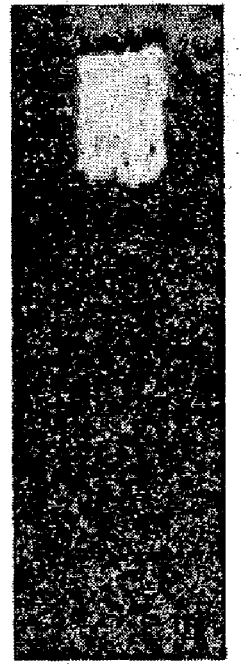
FIG. 1 shows the growth, on leucine deficient media, of yeast cells containing different constructs from a yeast two-hybrid assay. In addition, the results of a lacZ filter assay is shown. For this assay, pGilda-Bax (S184K) and pJG4-5-HN were transfected into yeast strain EGY48.
Figure 2:
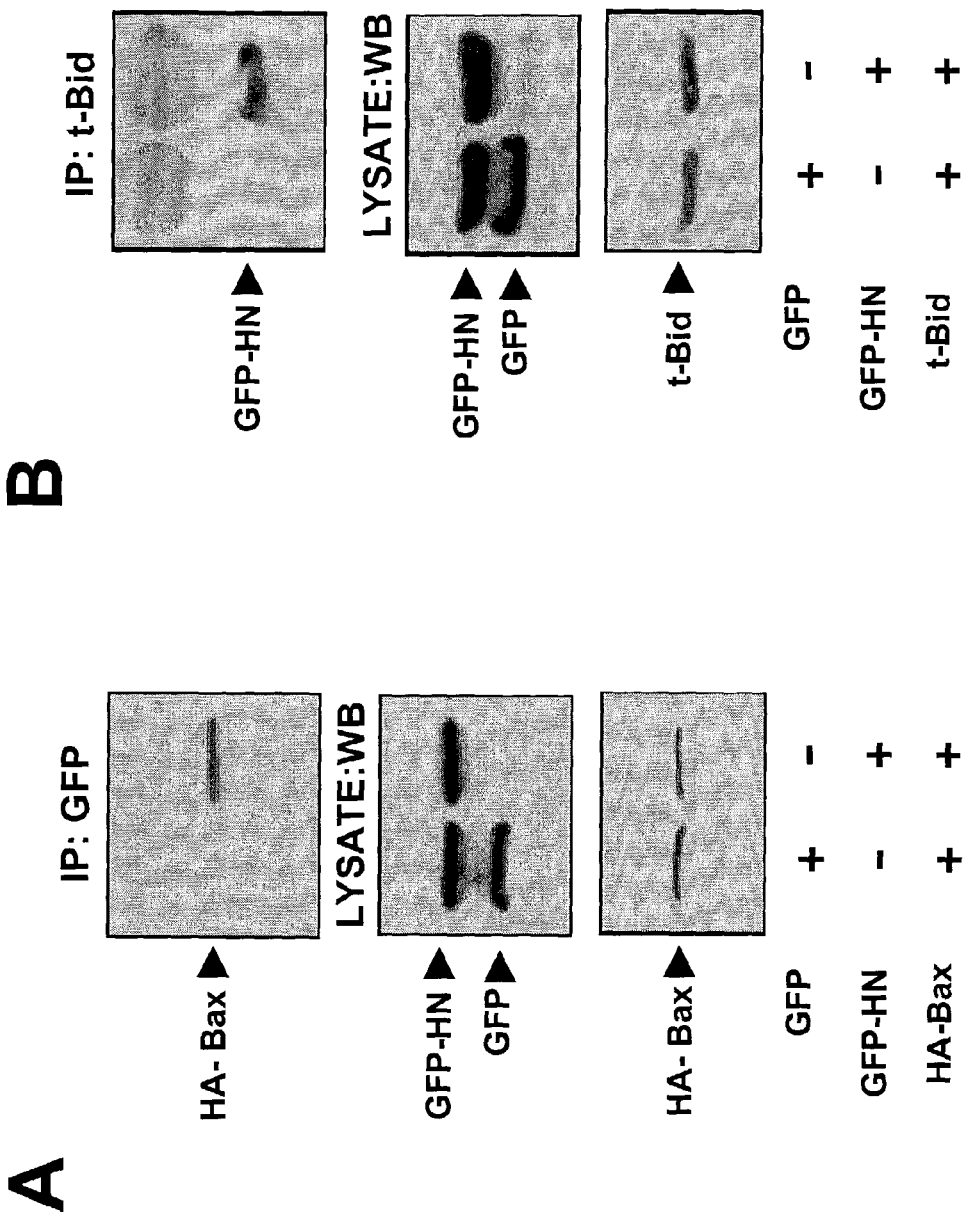
FIG. 2 shows immunoprecipitation assays where GFP and GFP-HN were co-transfected into 293T cells with (A) HA-Bax or (B) tBid. The lysates were immunoprecipitated with (A) anti-GFP antibody or (B) anti-tBid antibody and blotted with (A) anti-HA antibody or (B) anti-GFP antibody. The data shown were obtained using the cytosolic form of Humanin; however, both cytosolic and mitochondrial forms of Humanin were tested and the results were the same.

Disclosed herein is the discovery that Humanin can bind to and inhibit the pro-apoptotic function of Bax and Bid. The discovery that Bax can interact with Humanin came from a yeast two-hybrid screening assay that was performed to identify any polypeptides that interact with Bax. A mutant form of Bax that does not induce apoptosis was used (Nechushtan, et al. *EMBO J.* 18:2330-2341 (1990)). This assay is described in Example I. Several positive clones were sequenced from this assay and one of these clones contained a cDNA that encoded the Humanin gene. The Humanin polypeptide had not been reported to interact with any other polypeptides so several assays were performed to confirm that Humanin did interact with Bax. First, Humanin and Bax were assayed in the yeast two-hybrid system. As shown in FIG. 1, Humanin and Bax were co-expressed into yeast cells and cells that expressed both Humanin and Bax were able to grow on selection media indicating that the Humanin and Bax were interacting. The interaction of Humanin and Bax was further confirmed using a co-immunoprecipitation assay and a co-localization assay as described in Example II and shown in FIG. 2. In addition, a fragment of Bid, t-Bid, was found to interact with Humanin using the co-immunoprecipitation assay as shown in FIG. 2. Furthermore, transfection of the Humanin gene along with Bax or Bid resulted in a decrease of Bax- or Bid-induced apoptosis as described in Example V and shown in FIG. 4.

The discovery, disclosed herein, of Humanin-Bax and Humanin-Bid complexes enables the design of diagnostics and therapeutics based on these interactions. For example, this discovery enables the design of convenient high-throughput assays for identifying compounds that mimic or modulate the interaction between Humanin and Bax or Bid.

The interaction between Humanin and Bax or Bid can be used advantageously as a basis for the design of pharmaceutical screening assays. For example, compounds from chemical libraries can be tested for modulating the binding of Humanin to Bax or Bid. In addition, Humanin-like compounds can be designed and tested for binding to Bax or Bid. Similarly, Bax- or Bid-like compounds can be designed and tested for binding to Humanin. Several binding assay formats are well known in the art that are amenable for high-throughput screening. The use of these assays requires the knowledge of a stable interaction between two macromolecules such as Humanin and Bax or Humanin and Bid, as disclosed herein.

Figure 4:
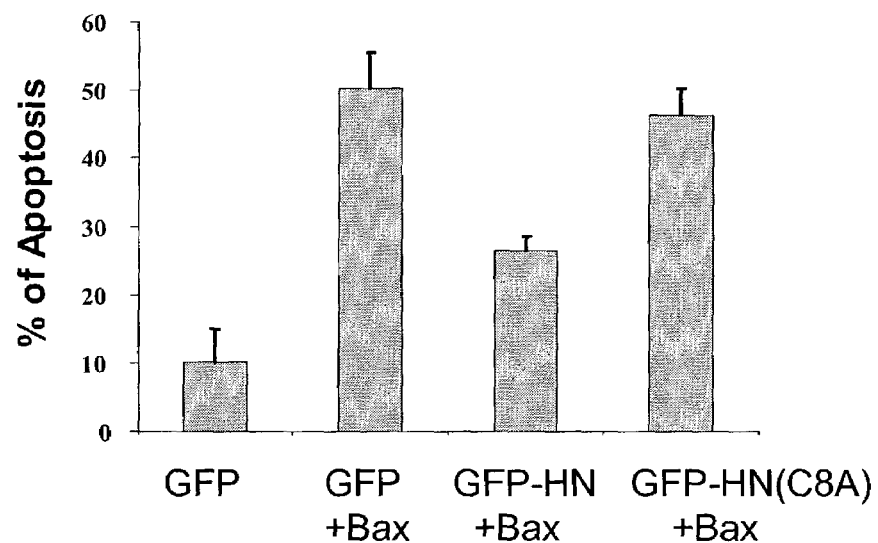
FIG. 4 shows the percentage of apoptosis in primary rat hippocampal neuronal cell line CSM14.1 cells co-transfected with GFP, GFP-Humanin, GFP-Humanin (C8A) and (A) Flag-Bax or (B) t-Bid. Apoptosis was examined by DAPI staining. The data shown were obtained using the cytosolic form of Humanin; however, both cytosolic and mitochondrial forms of Humanin were tested and the results were the same.
Figure 4:
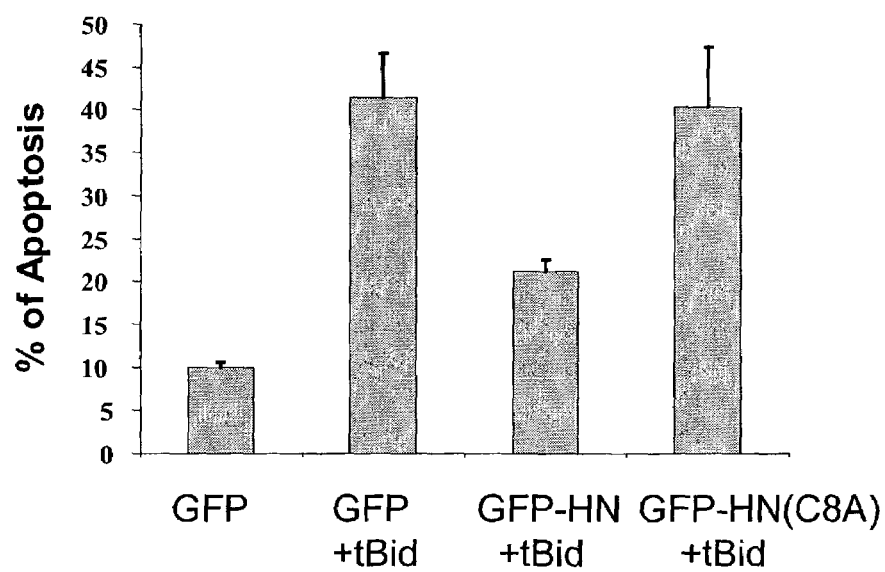

A functional interaction between Humanin and Bax and Humanin and Bid is also disclosed. As shown in FIG. 4, Humanin decreases Bax-induced apoptosis and Bid-induced apoptosis. A mechanism for how Bax decreases Bax-induced apoptosis is also disclosed herein. As shown in Example XI and FIGS. 7A-E, Humanin can suppress Bax translocation to mitochondria. Furthermore, as shown in Example XII and FIG. 7F, Humanin can stabilize the latent conformation of Bax in which its C-terminal tail is docked onto a hydrophobic crevice on the surface of the Bax molecule. These discoveries can also be used in the design of high-thoroughput functional screening assays. For example, Humanin-like compounds can be tested for their effect on Bax-induced apoptosis or Bid-induced apoptosis.

The interaction between Humanin and Bax or Bid also can be used advantageously for designing pharmaceutical compounds directly. The site of interaction between Humanin and Bax or Bid can be explored using several techniques well known in the art such as, for example, X-ray crystallography, nuclear magnetic radiation (NMR), and structure-function mutagenesis. The three dimensional structures of Bid (Chou et al., *Cell* 96:615-624 (1999); McDonnell et al., *Cell* 96:625-634 (1999)) and Bax (Suzuki et al., *Cell* 103:645-654 (2000)) are known. Knowledge of the three dimensional shape of the interaction site between Humanin and Bax or Bid can be used to design drugs that can mimic or modulate these interactions. This type of rational drug design requires the knowledge that Humanin interacts with Bax and Bid, as disclosed herein.

The discovery of Humanin-Bax and Humanin-Bid complexes can also be used to design diagnostic assays. The detection of these complexes or different amounts of these complexes within cells can be used to predict whether a cell will survive or undergo apoptosis. For example, when Bax or Bid is in a complex with Humanin a cell can be more likely to survive than when Bax and Bid are not bound to Humanin. These complexes can be detected by several methods, for example, using an antibody that specifically recognizes the complex. Determination of the apoptotic status of cells can be useful, for example, for the diagnosis of neurodegenerative diseases or cancer.

Figure 3:
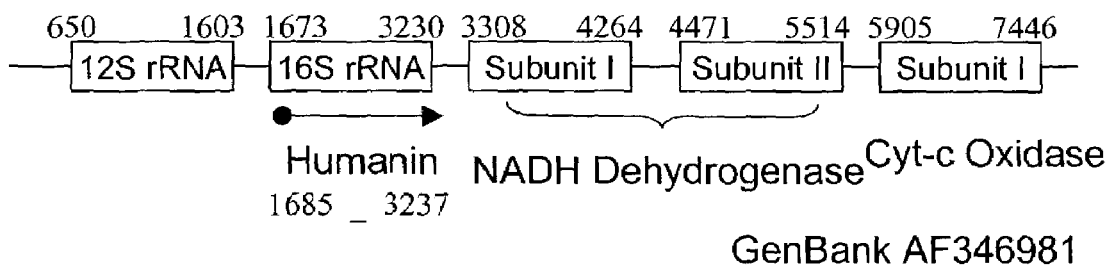
FIG. 3.
Figure 3:
Figure 3:
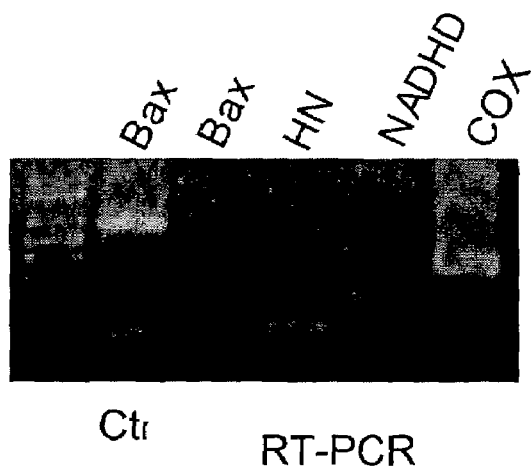

The Humanin polypeptide has been published as the 24 amino acid sequence shown in FIG. 3B (SEQ ID NO:2). Disclosed herein is evidence that Humanin is transcribed in mitochondria (see FIG. 3C). Based on this finding, and the mitochonrial genetic code, the invention provides a mitochondrial-derived Humanin polypeptide comprising the 21 amino acid sequence shown in FIG. 3B (SEQ ID NO:3). Humanin translated in mitochondria is predicted to contain one amino acid difference compared to the published Humanin polypeptide. As shown in FIG. 3, Humanin translated in the mitochondrial (mtHumanin) is predicted to contain a methionine (M) at residue 16 instead of an isoleucine (I) as found in the published form of Humanin. In addition, the mitochondrial form of Humanin is predicted to lack the three amino acid sequence arginine (R)-arginine (R)-alanine (A) at the carboxyl-terminus of the polypeptide. Since Humanin can be transcribed in mitochondria, the mitochondrial-derived form of Humanin can be considered a biologically relevant form of Humanin. This form of Humanin can be used in diagnostic and therapeutic methods as disclosed herein and apparent to one skilled in the art.

The invention provides methods for identification of compounds that modulate the binding of Humanin to Bax or Bid or modulate an activity of Bax or Bid. In addition, the invention provides a method of identifying Humanin-like compounds that bind to Bax or Bid or modulate an activity of Bax or Bid. In one embodiment, the invention provides a method of identifying Humanin-like compounds that bind to Bax or Bid using a competition assay. The invention also provides a method of diagnosing and/or treating a pathology characterized by an increased or decreased level of a Humanin-Bax or Humanin-Bid complex in a subject. The invention further provides a mitochrondrial derived form of Humanin of a different sequence than the cytosolic form and methods of diagnosing and/or treating a pathology characterized by Bax- or Bid-induced cell death.

As used herein, the term "Bax" refers to a polypeptide with substantially the same amino acid sequence as that shown in SEQ ID NO:5 (human Bax) that specifically binds to SEQ ID NO:2 or 3 (cytosolic or mitochondrial-derived Humanin, respectively). The GenBank accession number for the nucleotide sequence of human Bax is L22473. "Substantially the same amino acid sequence" is intended to mean an amino acid sequence contains a considerable degree of sequence identity or similarity, such as at least 70%, 80%, 90%, 95%, 98%, or 100% sequence identity or similarity, to a reference amino acid sequence. Conservative and non-conservative amino acid changes, gaps, and insertions to an amino acid sequence can be compared to a reference sequence using available algorithms and programs such as the Smith-Waterman algorithm and the BLAST homology search program (Altschul et al., *J. Mol. Biol.* 215:403-410 (1990)).

The term "specifically binds" is intended to mean the polypeptide will have an affinity for the target polypeptide that is measurably higher than its affinity for a non-specific interaction. Bax can bind to Humanin with low or high affinity so long as the binding is sufficient to be detectable. For example, Bax can bind Humanin with a binding affinity (Kd) of about $10^{-4}$ M or less, $10^{-5}$ M or less, $10^{-6}$ M or less, about $10^{-7}$ M or less, including about $10^{-8}$ M or less, such as $10^{-9}$ M or less. Several methods for detecting or measuring polypeptide binding are known in the art and disclosed herein.

It is understood that a fragment of Bax can be sufficient in order to produce this activity. For example, fragments of Bax which retain substantially the Humanin-binding function of the entire polypeptide are included within the definition. Fragments can include, for example, amino terminal, carboxyl terminal, or internal deletions of a full length Bax polypeptide. For example, a fragment can contain at least about 10, 20, 50, 75, 100, 125, 150, 175, or 190 or more contiguous or non-contiguous amino acid residues of a full-length Bax polypeptide. Polypeptide fragments can be generated, for example, using recombinant DNA methods or enzymatic or chemical cleavage of larger polypeptides. In addition, various molecules, such as other polypeptides, carbohydrates, or lipids, or small molecules can be attached to Bax including fragments of Bax. For example, Bax can contain a label moiety, a sequence such as a FLAG epitope, or be fused to another polypeptide such as a DNA binding domain.

It is understood that limited modifications to the Bax polypeptide can be made without destroying the ability of Bax to specifically bind to SEQ ID NO:2 or 3. For example, Bax is intended to include other Bax family members such as those polypeptides that are found to exhibit the above sequence homologies. Such members include, for example, homologs of Bax that can be cloned from other organisms such as monkeys, cows, rats, mice, chickens, frogs, flies or worms. The sequence of homologs of human Bax are available in the database. For example, the GenBank accession number for mouse Bax is L22472.

Various modifications of the Bax primary amino acid sequence can result in polypeptides having substantially equivalent, decreased, or enhanced function as compared to the sequence set forth as SEQ ID NO:5. Those skilled in the art recognize that such modifications can be desirable at times in order to enhance the bioactivity, bioavailability or stability of Bax, or to facilitate its synthesis or purification. Contemplated amino acid substitutions to the native sequence of Bax can include, for example, conservative changes, wherein a substituted amino acid has similar structural or chemical properties (e.g., replacement of a polar amino acid with another polar amino acid; replacement of a charged amino acid with a similarly charged amino acid, etc.). Those skilled in the art also recognize that nonconservative changes (e.g., replacement of an uncharged polar amino acid with an non-polar amino acid; replacement of a charged amino acid with an uncharged polar amino acid, etc.) can also be made without affecting a function of Bax. In addition, a variety of polypeptide modifications are known in the art for constraining the structure of polypeptides to enhance stability or binding (Cabezas and Satterthwait, *J. Am. Chem. Soc.* 121:3862-3875 (1999); Stanfield et al., *Structure* 7:131-142 (1999)).

A polypeptide can be modified by naturally occurring modifications such as post-translational modifications, including phosphorylation, lipidation, prenylation, sulfation, hydroxylation, acetylation, addition of carbohydrate, addition of prosthetic groups or cofactors, formation of disulfide bonds, proteolysis, assembly into macromolecular complexes, and the like. Chemical modifications of the polypeptide such as, for example, alkylation, acylation, carbamylation, and iodination can also be used so long as the polypeptide retains its ability to specifically bind to SEQ ID NO:2 or 3.

Those skilled in the art can determine which residues and which regions of a Bax sequence are likely to be tolerant of modification and still retain an ability to specifically bind to SEQ ID NO:2 or 3. For example, amino acid substitutions or chemical or enzymatic modifications at residues that are less well conserved between species are more likely to be tolerated than substitutions at highly conserved residues. Accordingly, an alignment can be performed among Bax sequences of various species to determine residues and regions in which modifications are likely to be tolerated. Additional guidance for determining residues and regions of Bax likely to be tolerant of modification is provided by studies of Bax fragments and variants. For example, the BH3 and transmembrane domains of Bax are important for apoptotic function as determined by structure-function comparisons of Bax in yeast and mammalian cells (Zha et al., *Mol. Cell. Biol.* 16:6494-6508 (1996); Reed et al., *Adv. Exp. Med. Biol.* 406: 99-112 (1996)).

As used herein, the term "Bid" refers to a polypeptide with substantially the same amino acid sequence as that shown in SEQ ID NO: 7 (human Bid) that specifically binds to SEQ ID NO:2 or 3 (cytosolic or mitochondrial-derived Humanin, respectively). The GenBank accession number for the nucleotide sequence of human Bid is AF042083. The definition of substantially the same amino acid sequence and specific binding is the same as stated above for Bax. For example, Bid can bind Humanin with a binding affinity (Kd) of about $10^{-4}$ M or less, $10^{-5}$ M or less, $10^{-6}$ M or less, about $10^{-7}$ M or less, including about $10^{-8}$ M or less, such as $10^{-9}$ M or less.

As with Bax it is understood that a fragment of Bid can be sufficient in order to produce this activity. For example, fragments of Bid which retain substantially the Humanin binding function of the entire polypeptide are included within the definition. Fragments can include, for example, amino terminal, carboxyl terminal, or internal deletions of a full length Bid polypeptide. For example, a fragment can contain at least about 10, 20, 50, 75, 100, 125, 135, 150, 175 or 190 or more contiguous or non-contiguous amino acid residues of a native Bid polypeptide. For example, a truncated fragment of Bid called t-Bid is shown herein to bind to Humanin. This 22 kD full length Bid polypeptide is cleaved into the 15 kD truncated form of Bid by caspase-8. The t-Bid polypeptide has the polypeptide sequence substantially the same as that shown in SEQ ID NO:9. In addition, various molecules, such as other polypeptides, carbohydrates, lipids, or small molecules can be attached to Bid including fragments of Bid such as t-Bid. For example, Bid can contain a sequence such as a c-myc epitope or be fused to another polypeptide such as a transcriptional activation domain.

It is understood that limited modifications to the Bid polypeptide can be made without destroying the ability of Bid to specifically bind to SEQ ID NO:2 or 3. For example, Bid is intended to include other Bid family members such as those polypeptides that are found to exhibit the above sequence homologies. Such members include, for example, homologs of Bid that can be cloned from other organisms such as monkeys, cows, rats, mice, chickens, frogs, flies or worms. The sequence of homologs of human Bid can be found in the database.

Various modifications of the Bid primary amino acid sequence can result in polypeptides having substantially equivalent, decreased, or enhanced function as compared to the sequences set forth as SEQ ID NOS: 7 or 9. Contemplated modifications include all of those listed above for the Bax polypeptide. Those skilled in the art can determine which residues and which regions of a Bid sequence are likely to be tolerant of modification and still retain an ability to specifically bind to SEQ ID NO:2 or 3. Additional guidance for determining residues and regions of Bid likely to be tolerant of modification is provided by studies of Bid fragments such as t-Bid. In addition, mutagenesis studies have shown that the BH3 domain of Bid is important for pro-apoptotic activity (Wang et al., *Genes Dev.* 10:2859-2869 (1996)).

As used herein, the term "Humanin" refers to a polypeptide with substantially the same amino acid sequence as that shown in SEQ ID NO:2 or 3 (cytosolic or mitochondrial-derived Humanin, respectively) that specifically binds to SEQ ID NO:5 (Bax) or SEQ ID NO: 7 or 9 (Bid or t-Bid, respectively). The GenBank accession number for the nucleotide sequence of human Humanin is AY029066. The definition of substantially the same amino acid sequence and specific binding is the same as stated above for Bax. For example, Humanin can bind Bax or Bid with a binding affinity (Kd) of about $10^{-4}$ M or less, $10^{-5}$ M or less, $10^{-6}$ M or less, about $10^{-7}$ M or less, including about $10^{-8}$ M or less, such as $10^{-9}$ M or less.

As with Bax, it is understood that a fragment of Humanin can be sufficient in order to produce this activity. For example, fragments of Humanin which retain substantially the Bax or Bid binding function of the entire polypeptide are included within the definition. Fragments can include, for example, amino terminal, carboxyl terminal, or internal deletions of either full length Humanin polypeptides. For example, a fragment can contain at least about 5, 7, 9, 11, 13, 15, 17, 19, 21, or 23 contiguous or non-contiguous amino acid residues of a full-length Humanin polypeptide. As disclosed herein in Table I, fragments of Humanin can be generated that retain Bax binding activity and the ability to decrease Bax-induced apoptosis. In addition, various molecules, such as other polypeptides, carbohydrates, lipids or small molecules can be attached to Humanin including fragments of Humanin. For example, Humanin can contain a sequence such as a histidine tag or be fused to another polypeptide such as a green fluorescent protein (GFP).

It is understood that limited modifications to the Humanin polypeptide can be made without destroying the ability of Humanin to specifically bind to SEQ ID NO: 5, 7, or 9. For example, Humanin is intended to include both the cytosolic (SEQ ID NO:2) and the mitochondrial-derived (SEQ ID NO:3) forms of Humanin in addition to Humanin family members such as those polypeptides that are found to exhibit the above sequence homologies. Such members include, for example, homologs of Humanin that can be cloned from other organisms such as monkeys, cows, rats, mice, chickens, frogs, flies or worms. In addition, the inventors have identified about 30 copies of the Humanin nucleotide sequence, some identical to SEQ ID NO: 1 and some with small modifications, in the human genome. In addition, using BLAST searches, the inventors have found that cDNAs identical or similar to Humanin are expressed in plants, nematodes, rats, mice and many other species (GenBank Accession numbers for Humanin and Humanin-like cDNAs are: BQ250660 {Wheat Triticum aestivun}, AI209224 {Nematode Onchorcerca volvulus}, BG667570 {Rat}, BM250174 {Mouse}).

Various modifications of the Humanin primary amino acid sequence can result in polypeptides having substantially equivalent, decreased, or enhanced function as compared to the sequences set forth as SEQ ID NOS: 2 and 3. Contemplated modifications include all of those described above for the Bax and Bid polypeptides. Those skilled in the art recognize that such modifications can be desirable at times in order to enhance the bioactivity, bioavailability or stability of Humanin, or to facilitate its synthesis or purification.

Those skilled in the art can determine which residues and in which regions of a Humanin sequence are likely to be tolerant of modification and still retain an ability to bind Bax or Bid at a detectable level. For example, as described above an alignment can be performed among Humanin sequences of various species to determine residues and regions in which modifications are likely to be tolerated. Additional guidance for determining residues and regions of Humanin likely to be tolerant of modification is provided by studies of Humanin fragments and variants. For example, since both the cytosolic and mitochondrial forms of Humanin bind to Bax and Bid, the carboxyl-terminal three residues of cytosolic Humanin are likely to be tolerant to modification.

The discovery that Humanin can bind to Bax and Bid and that co-expression of Humanin in cells that express Bax or Bid can rescue cells from Bax- or Bid-induced apoptosis, implicates the formation of a complex between Humanin and Bax or Humanin and Bid in the regulation of apoptosis. An increase in the amount or stability of a Humanin-Bax or Humanin-Bid complex can reduce or prevent apoptotic cell death, while a reduction in the amount or stability of a Humanin-Bax or Humanin-Bid complex can increase or induce apoptotic cell death. Free Bax or Bid can be involved in the initiation of apoptosis, while Bax or Bid sequestered in a complex with Humanin can be prevented from initiating apoptosis. It can be desirable to reduce or prevent apoptotic cell death, for example, in neurodegenerative diseases such as Alzheimer's disease. Alternatively, it can be desirable in some cases to increase or induce apoptotic cell death, for example, in tumors.

Methods of the invention are directed to the formation of Humanin-Bax or Humanin-Bid complexes and to compounds that can modulate the amount or stability of these complexes. For example, methods of the invention are directed to identifying an effective compound that modulates the binding of Humanin to Bax or Bid. In addition, methods of the invention are directed to identifying a Humanin-like compound that binds to Bax or Bid or modulates an activity of Bax or Bid. Furthermore, the methods of the invention are directed to identifying an effective compound that modulates an activity of Bax or Bid when complexed to Humanin.

In one aspect, the invention provides a method of identifying an effective compound that modulates the binding of Humanin to Bax by (a) contacting Humanin with Bax under conditions suitable to form a Humanin-Bax complex; (b) contacting the Humanin-Bax complex with a candidate compound; and (c) determining the ability of the candidate compound to modulate the binding of Humanin to Bax, where modulation of the binding of Humanin to Bax indicates that the candidate compound is an effective compound that modulates the binding of Humanin to Bax.

While the invention is often described below with specific embodiments to a Humanin-Bax complex or to Humanin-like compounds, it is understood that Humanin-Bid complexes and Bax-like compounds and Bid-like compounds can also be similarly used in the methods of the invention as described herein. Therefore, the invention also provides a method of identifying an effective compound that modulates the binding of Humanin to Bid by (a) contacting Humanin with Bid under conditions suitable to form a Humanin-Bid complex; (b) contacting the Humanin-Bid complex with a candidate compound; and (c) determining the ability of the candidate compound to modulate the binding of Humanin to Bid, where modulation of the binding of Humanin to Bid indicates that the candidate compound is an effective compound that modulates the binding of Humanin to Bid.

Humanin can be contacted with Bax, or Bid, either in an in vitro or in vivo environment. As used herein, the term "in vivo" is intended to mean within a living organism or living cell. A living organism includes for example, multi-cellular organisms such as a humans, animals, insects, or worms, and uni-cellular organisms such as a single-celled protozoan, yeast cell, or bacterium. In addition, a living cell derived from an organism used directly or grown in cell culture is considered to be an in vivo environment. For example, an oocyte removed from an organism such as a frog used directly or grown in a tissue culture dish would constitute an in vivo environment.

As used herein, the term "in vitro" is intended to mean in an artificial environment outside of a living organism or cell. Assays performed in a test tube, 96 well plate, or other assay format outside of an organism are considered in vitro assays. Experiments performed in cells or tissues that have been fixed and are therefore dead (sometimes referred to as in situ experiments) are considered an in vitro experiment. In addition, experiments using cell-free extracts from cells are considered to be in vitro experiments.

For an in vitro assay, Humanin and Bax or Bid polypeptides can be added together directly in a solution under conditions that are suitable for the formation of a complex. For example, this contact can occur in a test tube, microcentrifuge tube, or 96 well plate. In vitro assays can utilize isolated polypeptides or cell-free extracts derived from cell lines, yeast or bacteria. Polypeptides, such as those used for in vitro assays, can be of recombinant origin, purified from cellular or tissue sources, or chemically synthesized.

The isolated polypeptides used in the methods of the invention can be obtained using well-known recombinant methods (see, for example, Sambrook et al., supra, 1989; Ausubel et al., supra, 1999). An example of a method for preparing the invention polypeptides is to express nucleic acids encoding Bax, Bid, or Humanin in a suitable host cell, such as a bacterial cell, a yeast cell, an amphibian cell such as an oocyte, or a mammalian cell, using methods well known in the art, and recovering the expressed polypeptide, again using well-known purification methods, so described herein. Polypeptides can be isolated directly from cells that have been transformed with expression vectors as described herein. Recombinantly expressed polypeptides of the invention can also be expressed as fusion polypeptides with appropriate affinity tags, such as glutathione S transferase (GST) or poly His, and affinity purified.

The polypeptides of the invention can be prepared in substantially purified form using conventional biochemical purification methods, starting either from tissues containing the desired polypeptides or from recombinant sources. Polypeptides can be isolated by a variety of methods well-known in the art, for example, precipitation, gel filtration, ion-exchange, reverse-phase and affinity chromatography, and the like. Other well-known methods are described in Deutscher et al., *Guide to Protein Purification: Methods in Enzymoloqy Vol.* 182, (Academic Press, (1990)). The methods and conditions for biochemical purification of a polypeptide of the invention can be chosen by those skilled in the art, and purification monitored, for example, by an immunological assay or a functional assay.

The polypeptides of the invention, including fragments, and polypeptides with modifications, can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer. Methods for synthesizing polypeptides are well known in the art (see, for example, M. Bodanzsky, *Principles of Peptide Synthesis* (1st ed. & 2d rev. ed.), Springer-Verlag, New York, N.Y. (1984 & 1993), see Chapter 7; Stewart and Young, *Solid Phase Peptide Synthesis,* (2d ed.), Pierce Chemical Co., Rockford, Ill. (1984)).

Conditions suitable for the formation of a polypeptide complex in vitro are dependent on the characteristics of the polypeptides within the complex. For example, the overall charge of the polypeptides can be considered when adjusting the salt concentration or pH of a binding solution to optimize the stability of the complex. Usually a salt concentration and pH in the physiological range, for example, about 100 mM KCl and pH 7.0 are reasonable starting points. In addition, other components such as glycerol or protease inhibitors can be added to the solution, for example, to inhibit polypeptide degradation. The stability of the polypeptide complex and can be effected by the temperature of the binding reaction. The optimal temperature for binding can be experimentally determined by those skilled in the art. For example, binding reactions can be performed on ice (4° C.), at room temperature (about 25° C.) or at body temperature (37° C.)

Alternatively, a Humanin-Bax or Humanin-Bid complex can be formed in vivo. For example, these polypeptides can be recombinantly expressed in a living cell, such a cell in a human, or a cell line, a yeast cell or bacterial cell. These polypeptides can be expressed in a cell that does not normally contain one or both of these polypeptides, or in a cell that does express one or both of these polypeptides. For example, it can be desirable to over-express these polypeptides in a cell that expresses these polypepeptides at a low level.

Expression vectors containing Bax, Bid, or Humanin nucleic acids can be used in recombinant expression of these polypeptides in cells. Suitable expression vectors are well-known in the art and include vectors capable of expressing nucleic acid operatively linked to a regulatory sequence or element such as a promoter region or enhancer region that is capable of regulating expression of such nucleic acid. Appropriate expression vectors include those that are replicable in eukaryotic cells and/or prokaryotic cells and those that remain episomal or those which integrate into the host cell genome. Promoters or enhancers, depending upon the nature of the regulation, can be constitutive or regulated. The regulatory sequences or regulatory elements are operatively linked to a nucleic acid of the invention such that the physical and functional relationship between the nucleic acid and the regulatory sequence allows transcription of the nucleic acid.

Suitable vectors for expression in prokaryotic or eukaryotic cells are well known to those skilled in the art (see, for example, Ausubel et al., supra, 1999). Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. Vectors are useful for subcloning and amplifying a Bax, Bid or Humanin nucleic acid molecule and for recombinantly expressing a Bax, Bid or Humanin polypeptide. A vector can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art. One skilled in the art will know or can readily determine an appropriate promoter for expression in a particular host cell.

Vectors useful for expression of a Bax, Bid or Humanin polypeptide can contain a regulatory element that provides tissue specific or inducible expression of an operatively linked nucleic acid. One skilled in the art can readily determine an appropriate tissue-specific promotor or enhancer that allows expression of a Bax, Bid or Humanin polypeptide or nucleic acid in a desired tissue. Any of a variety of inducible promoters or enhancers can also be included in the vector for regulatable expression of a Bax, Bid or Humanin polypeptide or nucleic acid. Such inducible systems, include, for example, tetracycline inducible system (Gossen & Bizard, *Proc. Natl. Acad. Sci. USA*, 89:5547-5551 (1992); Gossen et al., *Science,* 268:1766-1769 (1995); Clontech, Palo Alto, Calif.); metal-lothionein promoter induced by heavy metals; insect steroid hormone responsive to ecdysone or related steroids such as muristerone (No et al., *Proc. Natl. Acad. Sci. USA,* 93:3346-3351 (1996); Yao et al., *Nature,* 366:476-479 (1993); Invitrogen, Carlsbad, Calif.); mouse mammory tumor virus (MMTV) induced by steroids such as glucocortocoid and estrogen (Lee et al., *Nature,* 294:228-232 (1981); and heat shock promoters inducible by temperature changes.

In addition, viral vectors such as retroviral, adenovirus, adeno-associated virus, lentivirus, and herpesvirus vectors can be used to express Bax, Bid or Humanin polypeptides into a cell. Viral based systems provide the advantage of being able to introduce relatively high levels of a heterologous nucleic acid into a variety of cells. Additionally, such viruses can introduce heterologous DNA into nondividing cells. Suitable viral vectors for introducing invention nucleic acid encoding a Bax, Bid or Humanin polypeptide into mammalian cells (e.g.,neuronal cell lines) are well known in the art. These viral vectors include, for example, Herpes simplex virus vectors (U.S. Pat. No. 5,501,979), Vaccinia virus vectors (U.S. Pat. No. 5,506,138), Cytomegalovirus vectors (U.S. Pat. No. 5,561,063), Modified Moloney murine leukemia virus vectors (U.S. Pat. No. 5,693,508), adenovirus vectors (U.S. Pat. Nos. 5,700,470 and 5,731,172), adeno-associated virus vectors (U.S. Pat. No. 5,604,090), constitutive and regulatable retrovirus vectors (U.S. Pat. Nos. 4,405,712; 4,650,764 and 5,739,018, respectively), papilloma virus vectors (U.S. Pat. Nos. 5,674,703 and 5,719,054), and the like.

Bax-, Bid- or Humanin-encoding vectors can be introduced into cells using transfection methods well-known to one skilled in the art. Such methods include, for example, infection using viral vectors, lipofection, electroporation, particle bombardment and transfection. Detailed procedures for these methods can be found in Sambrook et al., *Molecular Cloning: A Laboratory Manual* (Cold Spring Harbor Laboratory Press, 1989) and the references cited therein). Useful mammalian expression vectors and methods of introducing such vectors into mammalian cells either ex vivo or in vivo, for expression of the encoded polypeptide, are well known in the art. For example, a plasmid expression vector can be introduced into a cell by calcium-phosphate mediated transfection, DEAE-Dextran-mediated transfection, lipofection, polybrene- or polylysine-mediated transfection, electroporation, or by conjugation to an antibody, gramacidin S, artificial viral envelopes or other intracellular carriers. A viral expression vector can be introduced into a cell in an expressible form by infection or transduction, for example, or by encapsulation in a liposome.

Following transfection, cells expressing recombinant Bax, Bid, or Humanin, or increased levels of these polypeptides can be selected for use in the methods of the invention. In addition, polypeptides can be delivered directly into cells using a lipid-mediated delivery system (Zelphati et al., *J. Biol. Chem.* 276:35103-35110 (2001)). A quantitative assay such as, for example, immunoblot analysis, immunoprecipitation and ELISA can determine the amount of the polypeptides of the invention in the transfected cells. Such methods are known to one skilled in the art and can be found in Ausubel et al., *Current Protocols in Molecular Bioloqy* (John Wiley and Sons, 1989) or in Harlow et al., *Antibodies: A Laboratory Manual* (Cold Spring Harbor Laboratory Press, 1988)).

Additionally, recombinant cells containing Bax, Bid or Humanin nucleic acids can be used in the methods of the invention. The recombinant cells are generated by introducing into a host cell a vector containing a Bax, Bid or Humanin nucleic acid molecule. The recombinant cells are transducted, transfected or otherwise genetically modified. Exemplary host cells that can be used to express recombinant Bax, Bid or Humanin molecules include mammalian primary cells; established mammalian cell lines, such as COS, CHO, HeLa, NIH3T3, HEK 293, IMR-32, GT1-7 and PC12 cells; amphibian cells, such as *Xenopus embryos* and oocytes; and other vertebrate cells. Exemplary host cells also include insect cells such as Drosophila and *Spodoptera frugiperda* (e.g. for use in well-known baculovirus expression systems, such as described in Murakimi et al., 2001, *Cytokine*, 13(1):18-24, and the like), yeast cells such as *Saccharomyces cerevisiae, Saccharomyces pombe,* or *Pichia pastoris,* and prokaryotic cells such as *Escherichia coli.*

In addition to recombinantly expressing Bax, Bid, or Humanin polypeptides in a cell, a cell that endogenously expresses these polypeptides can be used directly in the methods of the invention. For example, a cell that already contains a Humanin-Bax or Humanin-Bid complex can be contacted with a compound. Therefore, the invention provides a method of identifying an effective compound that modulates the binding of Humanin to Bax, by (a) obtaining a cell that contains a Humanin-Bax complex; (b) contacting the cell containing the Humanin-Bax complex with a candidate compound; and (c) determining the ability of the candidate compound to modulate the binding of Humanin to Bax, where modulation of the binding of Humanin to Bax indicates that the candidate compound is an effective compound that modulates the binding of Humanin to Bax. For example, an antibody can be used to detect modulation of Humanin-Bax complex levels. In addition, the invention provides an analogous method of identifying an effective compound that modulates the binding of Humanin to Bid.

Humanin and Bax or Bid complexes can be detected by several methods, for example, using an antibody that specifically recognizes the complex. Other methods for detecting these complexes include detecting labeled Humanin bound to Bax or Bid which is immobilized. For example, a Humanin peptide or active fragment can be conjugated to a radiolabel, fluorescent label or enzyme label such as alkaline phosphatase, horse radish peroxidase or luciferase. Labeled Humanin can then bind to Bax or Bid which is immobilized for example, on a solid support such as a latex bead. Unbound Humanin is washed away and the amount of bound Humanin can be detected based on its label. Fluorescently labeled Humanin can also be bound to Bax or Bid in solution and bound complexes detected, for example using a fluorescence polarization assay (FPA). An example of a FPA is shown in Example VI and FIG. 5C. In addition, Humanin and Bax or Bid complexes can be detected using surface plasmon resonance as detected by a BIA Core chip. Furthermore, the binding of Humanin to $^{15}$N-labeled Bax or Bid can be detected using NMR.

As used herein the term "modulate" an activity refers to a compound's ability to alter an activity. For example, a compound can increase or decrease the binding or other activity of a polypeptide or complex of polypeptides. Such modulatory compounds include agonists, which increase an activity, and antagonists which decrease an activity. One skilled in the art understands that an increase or decrease in an activity is dependent on the particular assay used and takes into account the variability inherent in the assay. Assays to identify compounds that modulate an activity, for example the binding of Humanin to Bax or Bid, are described herein. As understood by those of skill in the art, assay methods for identifying compounds that modulate an activity generally require comparison to a "control." One type of a control is a reaction or cell that is treated substantially the same as the test reaction or cell exposed to the compound, with the distinction that the control reaction or cell is not exposed to the compound.

Several types of compounds can be assayed using the methods of the invention. As used herein, the term "compound" is intended to mean an isolated macromolecule of natural or synthetic origin that can be assayed using the methods of the invention. A compound includes, for example, a polypeptide, peptidomimetic, non-peptidyl compound, carbohydrate, lipid, an antibody or antibody fragment, a small organic or inorganic molecule, or a nucleotide sequence such as an aptamer. For example, a compound can be a small organic compound obtained from a combinatorial chemical library. A compound can have a known or unknown structure. A compound which is assayed in the methods of the invention is called a "candidate compound" and if the candidate compound has the desired activity it is called an "effective compound." One compound or more than one compound can be used in the methods of the invention.

A useful compound in the methods of the invention includes a Humanin-like compound. As used herein, the term "Humanin-like compound" is intended to mean a compound that is structurally related to Humanin or specifically binds to Bax, Bid (including t-Bid) in the same manner as Humanin. However, in contrast to Humanin, the Bax- or Bid-binding activity of a Humanin-like compound is not necessarily known a priori. A Humanin-like compound has physical characteristics that are similar to Humanin such as a similar topology or shape, or similar charge and charge spacing characteristics of Humanin.

A Humanin-like compound includes, for example, derivatives or analogues of Humanin polypeptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by polypeptide bonds. Similarly, the term also includes cyclic polypeptides and other conformationally constrained structures. Specific examples of modifications, analogs and derivatives can be found described in, for example, Roberts and Vellaccio, *The Peptides: Analysis, Synthesis, Bioloqy,* Eds. Gross and Meinhofer, Vol. 5, p. 341, Academic Press, Inc., New York, N.Y. (1983), and *Burger's Medicinal Chemistry and Drug Discovery,* Ed. Manfred E. Wolff, Ch. 15, pp. 619-620, John Wiley & Sons Inc., New York, N.Y. (1995)).

Humanin-like compounds also include peptidomimetics of Humanin. Peptidomimetics, which include chemically modified polypeptides, polypeptide-like molecules containing non-naturally occurring amino acids, peptoids and the like, have a structure substantially the same as the reference polypeptides upon which the peptidomimetic is derived (see, for example, "Burger's Medicinal Chemistry and Drug Discovery", 1995, supra). A peptidomimetic shows a considerable degree of structural identity when compared to the reference polypeptide and exhibits characteristics which are recognizable or known as being derived from or related to the reference polypeptide. Peptidomimetics include, for example, organic structures which exhibit similar properties such as charge and charge spacing characteristics of the reference polypeptide. Peptidomimetics also can include constrained structures so as to maintain optimal spacing and charge interactions of the amino acid functional groups.

Similarly, "Bax-like compound" and "Bid-like compound" is intended to mean a compound that is structurally related to Bax or Bid, respectively, or specifically binds to Humanin in the same manner as Bax or Bid, respectively. The Humanin-binding activity of the compound is not necessarily known a priori.

A candidate compound can be a polypeptide such as an antibody or antibody fragment. The antibody or antibody fragment can have binding affinity for any type of antigen including a polypeptide antigen or a small molecule antigen. These antibodies can be monoclonal antibodies or polyclonal antibodies. In addition, an antibody or antibody fragment can have binding affinity specifically for a Bax, Bid, or Humanin polypeptide. In addition to being a candidate or effective compound, an antibody or antibody fragment with affinity for a Bax, Bid, or Humanin polypeptide of the invention can be used to determine the amounts of these polypeptides either alone or in a complex.

An antibody can modulate the level of one or both of the polypeptides of the invention within a complex. For example, an antibody can block the binding site of the polypeptide or remove the polypeptide from its normal location. In addition, an antibody can increase or decrease the stability of the complex. For example, the binding of an antibody to a complex can induce a conformational change in one or both polypeptides that effects the stability of their interaction.

An isolated anti-Bax, anti-Bid, and anti-Humanin antibody having specific reactivity with Bax, Bid or Humanin, respectively can be used in the methods of the invention. These antibodies can be either monoclonal or polyclonal antibodies as well as antigen binding fragments of such antibodies. Cell lines producing monoclonal antibodies having specific reactivity with a polypeptide or complex of the invention can also be useful in providing a source of antibodies. An anti-Bax, anti-Bid, or anti-Humanin antibody, or antibody fragment is characterized by having specific binding activity for a Bax, Bid, or Humanin polypeptide or a polypeptide portion thereof of at least about $1 \times 10^5$ $M^{-1}$. Thus, Fab, $F(ab')_2$, Fd and Fv fragments of these antibodies which retain specific binding activity for a Bax, Bid, or Humanin polypeptide, are included within the definition of an antibody. Specific binding activity of a polypeptide of the invention can be readily determined by one skilled in the art. For example, specific binding activity of a Humanin polypeptide can be determined by comparing the binding activity of an anti-Humanin antibody to a Humanin polypeptide versus a control polypeptide that is not a Humanin polypeptide. In addition, an antibody can specifically recognize a complex of polypeptides. For example, an antibody can specifically bind to an epitope that includes amino acids from two different polypeptides that are in contact with each other. Methods of preparing polyclonal or monoclonal antibodies are well known to those skilled in the art (see, for example, Harlow and Lane, *Antibodies: A Laboratory Manual,* Cold Spring Harbor Laboratory Press (1988)).

In addition, the term antibody as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (*Science* 246:1275-1281 (1989)). These and other methods of making, for example, chimeric, humanized, CDR-grafted, single chain, and bifunctional antibodies are well known to those skilled in the art (Winter and Harris, *Immunol. Today* 14:243-246 (1993); Ward et al., *Nature* 341:544-546 (1989); Harlow and Lane, supra, 1988); Hilyard et al., *Protein Enqineering: A practical approach* (IRL Press 1992); Borrabeck, *Antibody Engineerinq,* 2d ed. (Oxford University Press 1995)).

A candidate compound can also include a nucleic acid or nucleotide sequence. Exemplary nucleotide sequences can include an anti-sense nucleotide sequence, an RNA molecule, or an aptamer sequence. For example, a nucleotide sequence, such as an aptamer, can bind to one or more components of a Bax-Humanin or Bid-Humanin complex and modulate the level or stability of that complex. Aptamers are nucleic acid sequences that have three dimensional structures capable of binding small molecular targets including metal ions, organic dyes, drugs, amino acids, co-factors, aminoglycosides, antibiotics, nucleotide base analogs, nucleotides and polypeptides (Jayasena, S. D., *Clinical Chemistry* 45:9, 1628-1650, (1999)). Nucleotide sequences can be modified by several methods known in the art in order to increase the stability of these nucleotide sequences within cells.

A sub-class of candidate compounds include the Humanin-like, Bax-like, and Bid-like compounds. These compounds are structurally related to Humanin, Bax, and Bid respectively, however their functional binding activity is not necessarily known a priori and so these compounds are assayed in the methods of the invention.

A Humanin-like compound can be a random compound, isolated based on a Humanin-like function, that when characterized is found to be structurally related to Humanin. Several methods are known in the art for determining the structure of a compound. For example, the structure of compounds that contain amino acid or nucleotide sequences can be determined using sequencing methods. Also, for example, several methods are known in the chemical arts for determining the structure of small molecules.

In addition, a Humanin-like compound can be rationally designed based on the structure of Humanin. For example, Humanin can be used as a template for the design of a library of peptidomimetics. As described earlier, a peptidomimetic refers to a non-peptide compound that is a topological analog of the corresponding polypeptide. Such a peptidomimetic can, for example, retain some or all of the functional groups of the amino acids shown to be functionally important in the polypeptide. A peptidomimetic can also, for example, consist partially or completely of a non-peptide backbone used in the art in the design of other peptidomimetics, such as a glucose scaffold, a pyrrolidinone scaffold, a steroidal scaffold, a benzodiazepine scaffold, or the like. Peptidomimetics can provide various advantages over polypeptides, and can be useful for oral administration since they can be stable when administered to a subject during passage throughout the digestive tract. In addition, peptidomimetics can be designed to allow for better penetration of the blood brain barrier (BBB)

Methods of rationally designing peptidomimetics of peptides are known in the art. For example, the rational design of three peptidomimetics based on the sulfated 8-mer peptide CCK26-33, and of two peptidomimetics based on the 11-mer peptide Substance P, and related peptidomimetic design principles, are described in Horwell, *Trends Biotechnol.* 13:132-134 (1995). Individual, rationally designed peptidomimetics of the polypeptides of the invention can be assayed for their ability to bind a relevant polypeptide, or to have some other activity using one or more of the assays described herein. Similarly, a plurality of peptidomimetic compounds, such as variants of a peptidomimetic lead compound, or a plurality of other compounds, can be assayed simultaneously or sequentially using the binding and functional assays described herein.

Methods for producing pluralities of candidate compounds to use in screening for effective compounds, including chemical or biological molecules such as simple or complex organic molecules, metal-containing compounds, carbohydrates, peptides, polypeptides, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.,* 2:363-371 (1998); Sofia, *Mol. Divers.* 3:75-94 (1998); Eichler et al., *Med. Res. Rev.* 15:481-496 (1995); and the like. Libraries containing large numbers of natural and synthetic compounds also can be obtained from commercial sources. Combinatorial libraries of molecules can be prepared using well known combinatorial chemistry methods (Gordon et al., *J. Med. Chem.* 37: 1233-1251 (1994); Gordon et al., *J. Med. Chem.* 37: 1385-1401 (1994); Gordon et al., *Acc. Chem. Res.* 29:144-154 (1996); Wilson and Czarnik, eds., *Combinatorial Chemistry: Synthesis and Application,* John Wiley & Sons, New York (1997)).

Compounds can be introduced into an assay, for example, by direct addition to a binding solution or by addition to cell culture media containing a target cell of interest. Depending on the chemical characteristics of the compound, one skilled in the art can adjust solution conditions to avoid precipitation of the compound out of solution. When adding a compound to a cell, some compounds, based on chemical structure, will enter the cell while other compounds will require some facilitation to penetrate the cell membrane. Several methods can be used to facilitate penetration of a compound through the cell membrane. For example, several lipids are known in the art which can chaperone compounds through a cell membrane. In addition, transformation or transfection methods such as electroporation or calcium phosphate precipitation can be used. In addition, spheroblasts, which are yeast cells lacking the cell wall, can be prepared by one skilled in the art.

Several assays are known in the art that can be used to determine the ability of a candidate compound to modulate the binding of Humanin to Bax or Bid. In addition, these binding assays can be used to assess the binding of a compound such as a Humanin-like compound to a polypeptide such as Bax or Bid. Analogously, these assays can be used to assess the binding of a compound such as a Bax-like compound or a Bid-like compound to a Humanin polypeptide. These binding assays include, for example, a two-hybrid assay, co-immunoprecipitation assay, co-localization assay, scintillation proximity assay (SPA), UV or chemical cross-linking, biomolecular interaction analysis (BIA), mass spectrometry (MS), nuclear magnetic resonance (NMR), and fluorescence polarization assays (FPA). These assays can be low- or high-throughput assays. In addition, these assays can be direct binding assays or competition binding assays (Yamamura et al., Methods in Neurotransmitter Receptor Analysis, Raven Press, New York).

Exemplary methods include, for example, transcription based assays such as reporter assays and two-hybrid assays, including yeast and mammalian two-hybrid assays. Such assays are well known in the art and can be found in standard reference texts such as Sambrook et al., supra, and Ausubel et al., supra, 1999. An example of a yeast two-hybrid assay is described in Example I.

Other methods for detecting the ability of a candidate compound to modulate the binding of Humanin to Bax or Bid or to assess the binding of a compound such as a Humanin-like compound to a polypeptide such as Bax or Bid include, for example, assaying a compound in co-immunoprecipitation assays, co-localization assays, ELISA assays, and FACS analysis, which are described, for example, in Harlow and Lane, Eds., *Antibodies: A Laboratory Manual,* Cold Spring Harbor Laboratory (1988). A candidate compound, for example a polypeptide, can be added to a Humanin-Bax or Humanin-Bid co-immunoprecipitation assay as described in Example II to determine whether the compound can modulate the binding of Humanin to Bax or Bid. In addition, for example, a Humanin-like compound can be added to Bax or Bid in the co-immunoprecipitation assay to determine whether the Humanin-like compound can bind to Bax or Bid.

High-thoroughput methods for detecting a modulatory compound or for detecting the binding of a Humanin-like compound to Bax or Bid can include, for example, a scintillation proximity assay (SPA) (Alouani, *Methods Mol. Biol.* 138:135-41 (2000)) or a fluorescence polarization assay (FPA) (Degterev, et al., *Nature Cell Biology* 3:173-182 (2001)). SPA involves the use of a fluomicrosphere coated with an acceptor molecule, such as an antibody, to which a ligand will bind selectively in a reversible manner. This assay can be used, for example to detect a Humanin-like compound that binds to Bax. For example, Bax can be bound to a fluomicrosphere using a Bax antibody and a $^3$H or $^{125}$I labeled Humanin-like compound can be added. If the labeled Humanin-like compound binds to Bax, the radiation energy from the Humanin-like compound is absorbed by the fluomicrosphere. This induces the fluomicrosphere to produce light which is easily measured. In addition, an SPA assay can be used to detect modulation of a Humanin-Bax or Humanin-Bid complex by a candidate compound. For example, Humanin can be bound to the fluormicrosphere and the amount of light generated in the presence of Bax can be measured. A candidate compound can then be added to the reaction and the amount of light generated can be measured and compared to the reaction without the compound.

A fluorescence polarization assay (FPA) can also be used, for example, to detect modulation of a Humanin-Bax or Humanin-Bid complex by a candidate compound. For example, Humanin can be labeled with a fluorophore such as Oregon Green (Molecular Probes, Eugene OR) and bound to a GST-Bax fusion protein. A candidate compound can be added and the displacement of fluorescently labeled Humanin from the GST-Bax fusion protein can be measured using a spectrophotometer, for example an Analyst plate reader (LJL Biosystems). An example of a FPA can be found herein in Example VI and FIG. 5C.

Another example of a method for detecting a modulatory compound or for detecting the binding of a Humanin-like compound to Bax or Bid can include, for example, UV or chemical cross-linking (Fancy, *Curr. Opin. Chem. Biol.* 4:28-33 (2000)) or a biomolecular interaction analysis (BIA) (Weinberger et al., *Pharmacogenomics* 1:395-416 (2000)). The binding of a Humanin-like compound to Bax or Bid can be determined by cross-linking these two components, if they interact, using UV or a chemical cross-linking agent. In addition, a biomolecular interaction analysis (BIA) can detect whether two components interact. One component, for example, Bax can be bound to a BIA chip and a second component such as a Humanin-like compound can be passed over the chip. If the two components interact an electrical signal is generated. This type of assay can also be used to detect compounds that modulate an interaction, for example a Humanin-Bax interaction. For example, Bax can be bound to the chip and Humanin can be passed over the chip. A candidate compound is then added and the signal is measured to determine the effect of the compound on the binding of Bax to Humanin.

Further examples of a method for detecting a modulatory compound or for detecting the binding of a Humanin-like compound to Bax or Bid can include, for example, mass spectrometry (MS) (McLafferty et al., *Science* 284:1289-1290 (1999) and Degterev, et al., *Nature Cell Biology* 3:173-182 (2001)), or nuclear magnetic resonance (NMR) (Shuker etal., *Science* 274:1531-1534 (1996), Hajduk et al., *J. Med. Chem.* 42:2315-2317 (1999), and Chen and Shapiro, *Anal. Chem.* 71:669A-675A (1999)). Mass spectrometry can be used to measure polypeptide interactions without the need for first labeling the polypeptides. For example, a polypeptide, such as Bax, can be covalently attached to a SELDI chip (Ciphergen) and the binding of a second component such as a Humanin-like compound to the immobilized polypeptide can be monitored by mass spectrometry. The samples embedding in the matrix can be analyzed for mass by matrix-assisted laser desorption ionization time-of-flight (MALDI-TOF) mass spectrometry. Likewise NMR spectroscopy can detect the interaction of two components. For example $^1H/\ ^{15}N$ HSQC spectra can be recorded by adding different amounts of a candidate compound and Humanin into $^{15}N$-labeled Bax/ $His_6$.

In addition, virtual computational methods (see for example, Shukur et al., supra 1996; Lengauer et al., 1996, *Current Opinions in Structural Biology*, 6:402-406; Choichet et al., 1991, *Journal of Molecular Biology*, 221:327-346; Cherfils et al., 1991, *Proteins*, 11:271-280; Palma et al., 2000, *Proteins*, 39:372-384; Eckert et al., 1999, *Cell* 99:103-115; Loo et al., 1999, *Med. Res. Rev.*, 19:307-319; Kramer et al., *J. Biol. Chem.*, (2000)), and the like can be used. Exemplary virtual computational methodology involves virtual docking of small-molecule compounds on a virtual representation of the polypeptide structure. In addition, other methods for detecting a modulatory compound or for detecting the binding of a Humanin-like compound to Bax or Bid can include, for example, any of those listed for screening for Bax inhibitory proteins as in U.S. Pat. No. 6,130,317.

The number of different compounds to screen in a particular assay can be determined by those skilled in the art, and can be 2 or more, such as 5, 10, 15, 20, 50 or 100 or more different compounds. For certain applications, such as when a library of random compounds is to be screened, and for automated procedures, it may be desirable to screen $10^3$ or more compounds, such as $10^5$ or more compounds, including $10^7$ or more compounds. Compounds can be screened individually or several compounds can be screen together. For example, several compounds can be added to one well of a multi-well plate and if a positive signal is obtained from that well the compounds can be separated into individual wells and re-tested for the desired activity. Testing several compounds at one time in a multiplexed reaction can allow a large number of compounds to be tested in a shorter period of time.

The methods of the invention identify effective compound that can increase or decrease the binding of Humanin to Bax or Bid. In addition, effective compounds can increase or decrease the stability of Humanin-Bax or Humanin-Bid complexes. The stability of a complex can be assessed by determining the on/off rate of the components of the complex. For example, Scatchard analysis can be used determine the on/off rate of the components of a complex (Schutz W., *Wien Klin Wochenschr* 103:438-42 (1991); Monot, et al. *Fundam Clin Pharmacol* 81:18-25 (1994)).

The invention further provides a method for modulating an activity mediated by a Bax or Bid polypeptide by contacting the polypeptide with an effective, modulating amount of an compound that modulates Bax or Bid activity. Modulation of an activity in a particular assay can be determined by quantitating levels of activity within the assay. As understood by those of skill in the art, assay methods for identifying compounds that modulate an activity generally require comparison to a control or standard.

In addition to methods that identify compounds that modulate the binding of Humanin to Bax, the invention also provides several methods to identify a Humanin-like compound that binds to Bax. These methods include, for example, direct binding assays, survival assays, and competition assays.

The invention provides a method for identifying a Humanin-like compound that binds to Bax, by: (a) contacting the Humanin-like compound with Bax, under conditions suitable to form a complex; and (b) determining the ability of the Humanin-like compound to bind Bax. The contacting of the Humain-like compound with Bax can occur in vitro such as within a test tube, or in vivo such as within a yeast or bacterial cell. The assays described above such as the two-hybrid assay, co-immunoprecipitation assay, co-localization assay, scintillation proximity assay (SPA), UV or chemical cross-linking, biomolecular interaction analysis (BIA), mass spectrometry (MS), nuclear magnetic resonance (NMR), and fluorescence polarization assays (FPA) can be used to determine the ability of the Humanin-like compound to bind to Bax or Bid.

The invention also provides a method of determining the level of binding between a Humanin-like compound and Bax by: (a) contacting the Humanin-like compound with Bax under conditions suitable to form a complex; (b) determining the amount of binding of the Humanin-like compound to Bax; and (c) comparing the amount of binding of the Humanin-like compound to Bax, to the amount of binding of Humanin to Bax in a reference sample. Again, the contacting can be performed in vitro or in vivo and the assay methods described above, for example, a biomolecular interaction analysis (BIA) can be used.

In addition to measuring the binding of a Humanin-like compound to Bax or Bid using the assays described above, the invention also provides a survival or selection type of assay. The invention provides a method for identifying a Humanin-like compound that inhibits the apoptotic activity of Bax by: (a) expressing Bax in a cell, wherein expression results in the death of said cell; (b) exposing the cell to a Humanin-like compound; and (c) detecting the survival of the cell, where survival indicates that the Humanin-like compound binds to Bax. This type of assay can be performed, for example in a mammalian cell such as the cells used in Example IV and FIG. 4, or in a non-mammalian cell such as a yeast cell. In addition, for example, the Bax polypeptide can be expressed from an inducible expression vector, as described earlier. Furthermore an analogous assay can be used where cell death is induced by Bid or t-Bid.

An example of a survival assay can be to express a Bax in a mammalian cell line under the control of an inducible promoter so that in the presence of the inducer the cells are no longer able to grow in culture. This cell line can be aliquoted into a 96 well plate with media that contains the inducer. A compound or Humanin-like compound can be then be added to these cells or expressed in these cells. The cells are then incubated under conditions amenable for cell growth for two to three days. The amount of cell growth can be measured by a variety of assays. For example, optical density measurements of the well using a standard spectrophotometer, uptake of dyes such as trypan blue or alomar blue, uptake of $^3$H or any other cell viability assay. As a positive control, full length Humanin can be added to or expressed in these cells resulting in cell growth.

Another example of a survival assay system can be to express a mammalian Bax in yeast. For this assay, a yeast cell strain can be constructed with a mammalian Bax under the control of an inducible promoter. Expression of the mammalian Bax polypeptide in yeast will result in yeast cell death. A compound or Humanin-like compound can be added to or expressed in this yeast cell stain and compounds that modulate Bax-induced cell death will result in the survival or growth of yeast colonies. Yeast cell survival can be easily detected by identifying colonies on solid media or can be measured in liquid cultures by optical density.

The invention also provides a competition assay format for the detection of a Humanin-like compound that binds to Bax. The invention provides a method for identifying a Humanin-like compound that binds to Bax, by: (a) contacting Humanin with Bax under conditions suitable to form a Humanin-Bax complex; (b) contacting the Humanin-Bax complex with the Humanin-like compound; and (c) determining the ability of the Humanin-like compound to bind to Bax. This type of assay can be performed, for example, in vitro in a 96 well plate.

The method described above can be performed, for example, utilizing a labeled Humanin polypeptide. As used herein, the terms "label" refer to molecules that are either directly or indirectly involved in the production of a detectable signal. Any label can be linked to polypeptides or compounds used in the methods of the invention. These atoms or molecules can be used alone or in conjunction with additional reagents. Such labels are themselves well-known in clinical diagnostic chemistry.

The labeling means can be a fluorescent labeling compound that chemically binds to polypeptides without denaturation to form a fluorochrome (dye) that is a useful fluorescent tracer. In addition, a radioactive moiety can be attached to or incorporated within a polypeptide of the invention. For example, a polypeptide can be iodinated with $^{125}$I or can be synthesized in the presence of $^{35}$S labeled amino acids, using methods well known in the art. See, for example, Galfre et al., *Meth. Enzymol.*, 73:3-46 (1981). Conventional means of polypeptide conjugation or coupling by activated functional groups are also applicable. See, for example, Aurameas et al., *Scand. J. Immunol.*, Vol. 8, Suppl. 7:7-23 (1978), Rodwell et al., *Biotech.*, 3:889-894 (1984), and U.S. Pat. No. 4,493,795.

An example of a competition assay as described above can be to contact a known amount of $^{125}$I labeled Humanin with Bax in a microcentrifuge,tube under conditions suitable to form a Humanin-Bax complex. A Humanin-like compound can then be added to above mixture and allowed to interact for a specified period of time. An antibody to Bax can then be added and antibody-Bax complex can be precipitated using for example, a protein A sepharose bead. The amount of radioactivity in the pellet compared to the supernatant indicates whether the Humanin-like compound was able to compete with the labeled Humanin for binding to Bax. Alternatively, the Humanin-like compound can be labeled and the Humanin used in complex can be unlabeled. Competition assays can also be performed using an SPA, FPA and BIA format as described previously above.

Also provided herein are methods of identifying a site on Humanin that interacts with Bax or Bid, said method comprising, constructing a plurality of Humanin mutants; contacting the Humanin mutants with Bax or Bid under conditions that permit Bax or Bid binding to native Humanin; and selecting a Humanin mutant that does not bind to Bax or Bid, thereby identifying a site on Humanin that interacts with Bax or Bid. The same procedure can be used to identify a site on Bax or Bid that interacts with Humanin. Methods for constructing mutants are well-known in the art including single or multiple amino-acid deletions or substitutions, truncated mutants, and the like. Once a region containing a binding site on Humanin or Bax or Bid is identified, this site can be used as a target in bioassays to identify compounds that can bind to and modulate this site.

Techniques of structural biology can also be used to identify sites on Humanin or Bax and Bid required for their interactions, using techniques such as X-ray crystallography, photoaffinity labeling, MALDI mass spectrometry (see, e.g., Kramer et al., *J. Biol. Chem.*, supra, (2000) and the like); and high speed NMR using TROSY (transverse relaxation-optimized spectroscopy; see, e.g., Pervushin et al., *PNAS, USA,* 94:12366-12371 (1997)) methods. Exemplary virtual computational methods include, for example, protein-protein docking prediction (as described in, e.g., Lengauer et al., *Current Opinions in Structural Bioloqy,* 6:402-406 (1996); Choichet et al., *Journal of Molecular Bioloqy,* 221:327-346 (1991); Cherfils et al., *Proteins,* 11:271-280 (1991); Palma et al., *Proteins,* 39:372-384 (2000); and the like).

In addition to identifying a Humanin-like compound that binds to Bax, the invention also provides a method for identifying a Humanin-like compound that modulates an activity of Bax by: (a) measuring an activity of Bax; (b) contacting Bax with a Humanin-like compound under conditions suitable to form a Humanin-like compound/Bax complex; (c) determining the amount of activity of Bax when bound to the Humanin-like compound and (d) comparing the amount of activity of from step (a) with the amount of activity from step (c). The contacting of Bax with a Humanin-like compound can be performed in vitro or in vivo.

The activity of Bax can be increased or decreased by the Humanin-like compound. In addition, an analogous assay can be used to identify a Humanin-like compound that binds to Bid. Furthermore, an analogous assay can be used to identify a Bax-like compound or a Bid-like compound that binds to Humanin.

Several activities of Bax, or Bid, can be measured. For example, Bax can form dimers with Bcl-2 related polypeptides, homodimerize or self-associate, translocate from the cytosol to mitochondria upon activation, integrate into membranes, for example in a mitochondrial membrane, form a pore, and induce cell death. In addition, Bid can translocate from the cytosol to mitochondria upon activation, form dimers with Bcl-2 related polypeptides, integrate into membranes such as mitochondrial membranes, trigger Bax activation and pore formation, and induce cell death. Furthermore, Bax and Bid can indirectly activate the caspase cascade by causing the release of cytochrome c from the mitochondria. When this released cytochrome c associates with Apaf-1, activate procaspase-9 can be activated which initiates a cascade of caspases. All of these steps can be measured using assays well known in the art or described herein.

Induction of apoptosis by Bax or Bid can involve different mechanisms. For example, Bcl-2 family members are known to heterodimerize and homodimerize in a way that regulates the activities of the polypeptides in the dimer. For example, the anti-apoptotic Bcl-2 polypeptide can dimerize with and thereby inactivate the pro-apoptotic Bax polypeptide. The ratio of Bcl-2 to Bax can indicate whether a cell will undergo apoptosis or survive. Dimerization of Bcl-2 family member polypeptides in mitochondrial membranes can be a mechanism to regulate apoptosis at the mitocondrial level. This dimerization can be achieved when the BH3 domain of one molecule binds into a pocket formed by the BH1, BH2, and BH3 domains of another family member. In addition, Bcl-2 family members in mitochondrial membranes can interact with other polypeptides. For example, in C. elegans the Bcl-2 homologue CED-9 protects cells from death by directly binding to an sequestering the Apaf-1 homologue CED-4.

Assays for determining whether Bax or Bid can form dimers with other Bcl-2 family members are well known in the art and include all the protein-protein interaction assays described herein. For example, the ability of Bax to dimerize with Bcl-2 can be detected using an immunoprecipitation assay as described by Oltvai et al. supra (1993).

Bcl-2 family members can insert into synthetic lipid bilayers, oligomerize, and form channels with discrete conductances. It has been proposed that Bcl-2 family members can form a pore in the mitochondria through which cytochrome c and other polypeptides can be released. In addition, proapoptotic Bcl-2 family members can recruit other mitochondrial outer membrane proteins into forming a pore or channel. For example, several Bcl-2 family members can bind to the voltage-dependent anion channel (VDAC) polypeptide and regulate its channel activity. Furthermore, it is possible that Bcl-2 family members control the homoeostasis of the mitochondria so that apoptotic signals result in rupture of the mitochondrial outer membrane and release of cytochrome c.

Assays for measuring the formation of a pore in a lipid bilayer include ion-efflux or dye efflux assays using unilammelar liposomes or electrical measurements in planar bilayer membranes such as those described in Schendel et al., *J. Biol. Chem.* 274:21932-21936 (1999); Schendel et al., *Proc. Natl. Acad. Sci USA* 94:5113-5188 (1997); and Montal et al., *Proc. Natl. Acad. Sci USA* 69:3561-3566 (1972). Both Bax and t-Bid are able to form pores in lipid bilayers.

Bax and Bid can indirectly activate the caspase cascade by causing the release of cytochrome c from the mitochondria. Assays to detect cells with active caspases can be performed, for example by staining these cells using a CaspaTag kit (Intergen). In addition, the invention provides a method for identifying a Humanin-like compound that modulates an activity of Bax by measuring an activity downstream of Bax. For example, the invention provides a method for identifying a Humanin-like compound that modulates an activity of Bax by: (a) expressing Bax in a cell, where expression results in the activation of an enzyme; (b) expressing in the cell a Humanin-like compound; and (c) detecting the level of the enzyme, where modulation of the enzyme level indicates that the Humanin-like compound modulates an activity of Bax. The enzyme can be, for example, a caspase.

In addition to identifying a Humanin-like compound that modulates an activity of Bax, the invention provides a method of identifying any effective compound that modulates an activity of Bax by: (a) contacting Humanin with Bax under conditions suitable to form a Humanin-Bax complex; (b) measuring an activity of Bax; (c) contacting the Humanin-Bax complex with a candidate compound; (d) determining the amount of activity of Bax in the presence of the candidate compound; and (e) comparing the amount of activity from step (b) with the amount of activity from step (d), where modulation of an activity of Bax indicates that the candidate compound is an effective compound that modulates an activity of Bax.

The contacting of Humanin with Bax and the Humanin-Bax complex with a candidate compound can be performed in vitro or in vivo. All of the candidate compounds listed above including a polypeptide, peptidomimetic, non-peptidyl compound, carbohydrate, lipid, a synthetic compound, a natural product, an antibody or antibody fragment, a small organic molecules, a small inorganic molecule, and a nucleotide sequence can be used in this assay. Furthermore, the same assays described above for detecting an activity of Bax can be used.

In addition to identifying a Humanin-like compound that modulates an activity of Bax or Bid, an analogous method can be used to identify a Bax-like compound or Bid-like compound that modulates an activity of Humanin. An activity of Humanin that can be measured is its ability to decrease apoptosis in cells transfected with Bax or Bid. Another activity of Humanin is its ability to decrease apoptosis in cells transfected with familial Alzheimer's genes or beta amyloid fragments. For example, the V642I form of APP is known to cause cell death when transfected into F11 cells (Hashimoto et al., supra (2001)). Several assays well known in the art can be used to measure apoptotic cell death. These assays detect changes in the cell membrane or the digestion of DNA into a ladder. For example, annexin V/PI staining can be performed with an Annexin V-EGFP apoptosis detection kit (PanVera). TUNEL assays can also be used to detect apoptosis, for example using a Fluorescent FragEL kit (Oncogene Research Products).

The invention also provides a method of diagnosing and treating a pathology characterized by a Humanin-Bax or Humanin-Bid complex. For example, the invention provides a method of diagnosing or predicting a pathology characterized by an increased or decreased level of Humanin-Bax complexes in a subject by: (a) obtaining a test sample from the subject; (b) determining the amount of Humanin-Bax complex in the test sample and (c) comparing the amount of Humanin-Bax complex in the test sample with the amount of Humanin-Bax complex in a reference sample, where an increased or decreased amount of the complex in the test sample as compared to the reference sample is diagnostic or predictive of a pathology.

Pathologies that can be characterized by a Humanin-Bax or Humanin-Bid complex can include any disease where Bax or Bid-induced apoptosis is implicated. Such pathologies include stroke, heart attack, autoimmunity, trauma, neuron cell death, inflammatory diseases, and cancer. In this regard, Bax has been implicated through gene ablation studies in mouse models in numerous diseases associated with pathological cell loss, including stroke, Parkinson's disease, and oocyte depletion during menopause, making it a promising target for new therapies. In addition, neurodegenerative diseases such as Alzheimer's disease, Parkinson's disease, Huntington's disease and Amyotrophic Lateral Sclerosis (ALS), and diseases induced by excitoxicity can be included in pathologies characterized by Humanin-Bax or Humanin-Bid complexes. The presence, absence, increased or decreased level of a Humanin-Bax or Humanin-Bid complex can be indicative of one of these pathologies.

Parkinson's disease is a progressive and ultimately fatal neurodegenerative disorder characterized by loss of the pigmented dopaminergic neurons of the substantia nigra. The symptoms of Parkinson's disease can often be managed initially by administration of L-DOPA, the immediate precursor of dopamine. However, reduced efficacy of L-DOPA treatment often occurs possibly because metabolism of the drug prevents effective delivery to the CNS. Programmed cell death has also been implicated to play an important role in this neurodegenerative disorder inasmuch as withdrawal of neurotrophic factors from neurons leads to cell death through a mechanism consistent with apoptosis. Moreover, the absence of inflammatory cells or scar formation in the brains of patients with Parkinson's disease indicates that striatal neuron death can occur through apoptosis as opposed, for example, to necrosis.

ALS is characterized clinically by progressive weakness, muscle atrophy, and eventual paralysis and death. These symptoms are due to the progressive degenerative of upper and lower motor neurons in the brain and spinal cord. Aberrantly occurring apoptosis can be a cause of motor neuron loss in ALS (Martin et al., *J. Neuropathol. Exp. Neurol.* 58:459-471 (1999); Martin et al., *Int. J. Mol. Med.* 5:3-13 (2000)). Motor neurons undergo DNA fragmentation and are eliminated with minimal inflammatory involvement. In addition, mitochrondrial enriched fractions from postmortem samples of ALS motor cortex and spinal cord, show increased Bax and Bak protein levels and reduced Bcl-2 protein levels.

In addition to neurodegenerative disorders, apoptosis has been indicated to result in cell death from glutamate-induced neurotoxicity arising from conditions such as stroke. Glutamate-induced toxicity occurs when glutamate is released from dying neurons in the brain at times of acute injury. Glutamate released by dying neurons in turn binds to specific receptors for glutamate on adjacent healthy neurons, triggering signals that set-off a complex series of biochemical events leading to apoptotic cell death.

As described earlier, Alzheimer's disease (AD) is the most common type of dementia occurring in middle and late life. AD causes profound degeneration of the cerebral cortex and loss of neurons in the neocortex and hippocampus. Inherited cases of AD are linked to mutation in the genes encoding amyloid precursor protein or presenilin proteins. The amyloid hypothesis of AD is based on the premise that generation of a fragment of APP called amyoid-b protien is a critical pathogenic mechanism. Overexpression and intracellular accumulation of APP activates caspase-3, APP is a target of caspase-3 and APP cleavage by caspase-3 or caspase-6 can promote Ab formation (Uetsuki et al., *J. Neurosci.* 19:6955-6964 (1999); Weidemann, et al., *J. Biol. Chem.* 274:5823-5829 (1999); Gervais et al., *Cell* 97:395-406 (1999); LeBlanc et al., *J. Biol. Chem.* 274:23426-23436 (1999)). Currently AD is diagnosed based on a checklist of symptoms, however no biological diagnostic procedures are available and a post-mortem brain biopsy is currently used to confirm the diagnosis of AD.

The invention additionally provides a method of identifying pathologically proliferative cells, such as neoplastic cells, in a sample in order to diagnose cancer, monitor cancer therapy, or assess the prognosis of patients with cancer by determining the presence, absence, increased or decreased level of a Humanin-Bax or Humanin-Bid complex in a sample from a patient. Several cancer chemotherapeutics act through a variety of intracellular targets which culminate in the activation of the apoptotic pathway.

As used herein, the term "neoplastic cell" is intended to mean a cell that exhibits histological or proliferative features of a malignant or premalignant cell. For example, by histological methods, a neoplastic cell can be observed to invade into surrounding normal tissue, have an increased mitotic index, an increased nuclear to cytoplasmic ratio, altered deposition of extracellular matrix, or a less differentiated phenotype. A neoplastic cell can also exhibit unregulated proliferation, such as anchorage independent cell growth, proliferation in reduced-serum medium, loss of contact inhibition, or rapid proliferation compared to normal cells. The diagnostic methods described herein are applicable to the identification of any type of neoplastic cell, such as neoplastic cells present in solid tumors (carcinomas and sarcomas) such as breast, colorectal, gynecological, lung, prostate, bladder, renal, liver, urethral, endocrinal, melanoma, basal cell, central nervous system, lymphoma, stomach, esophageal, squamous cell cancers, as well as all forms of leukemias, and metastases therefrom.

The diagnostic methods described herein can also be adapted for use as prognostic assays. Such an application takes advantage of the observation that alterations in expression or structure of different molecules involved in apoptosis can take place at characteristic stages in the progression of a proliferative disease or of a tumor. Knowledge of the stage of the tumor allows the clinician to select the most appropriate treatment for the tumor and to predict the likelihood of success of that treatment.

In the methods of the invention, a sample to be analyzed is obtained from the individual to be diagnosed. The term "sample," as used herein, means any biological specimen obtained from an individual that contains Humanin, Bax or Bid. A sample can be, for example, whole blood, plasma, saliva or other bodily fluid or tissue containing these polypeptides. One skilled in the art understands that samples such as serum samples can be diluted prior to analysis of polypeptide or polypeptide complex content.

As used herein, the term "subject" is intended to mean any animal containing neurons, for example, a mammal such as a mouse, rat, dog, primate or human. A subject can suffer from or be at high risk of developing any disease related to apoptosis such as autoimmune diseases, cancer, stroke, or a neurodegenerative disorder such as Parkinson's disease, Huntington's disease, Alzheimer's disease, ALS, multiple sclerosis; epilepsy; head or spinal cord injury; optic neuropathies including glaucoma and macular degeneration, and disorders of photoreceptor degeneration such as retinitis pigmentosa; metabolic, mitochondrial or infectious brain abnormalities such as encephalitis, or suffers from neuropathic pain (see, for example, Lipton and Rosenberg, *New Enql. J. Med.* 330: 613 (1994)).

Immunological procedures useful for in vi Lro or in vivo detection of Humanin-Bax or Humanin-Bid complexes in a sample include immunoassays that employ a detectable antibody. Such immunoassays include, for example, immunohistochemistry, immunofluorescence, ELISA assays, radioimmunoassay, FACS analysis, immunoprecipitation, immunoblot analysis, Pandex microfluorimetric assay, agglutination assays, flow cytometry and serum diagnostic assays, which are well known in the art (Harlow and Lane, supra, 1988; Harlow and Lane, *Using Antibodies: A Laboratory Manual*, Cold Spring Harbor Press (1999)). An antibody can be made detectable by various means well known in the art. For example, a detectable marker can be directly attached to the antibody or indirectly attached using, for example, a secondary compound that recognizes a Humanin, Bax, or Bid specific antibody. Useful markers include, for example, radionucleotides, enzymes, binding polypeptides such as biotin, fluorogens, chromogens and chemiluminescent labels.

In accordance with another embodiment of the present invention, there are provided diagnostic systems, preferably in kit form, comprising at least one invention polypeptide or antibody in a suitable packaging material. A suitable diagnostic system includes at least one invention polypeptide or antibody, as a separately packaged chemical reagent(s) in an amount sufficient for at least one assay. A kit containing a Humanin, Bax, or Bid antibody can contain a reaction cocktail that provides the proper conditions for performing an assay, for example, an ELISA or other immunoassay, for determining the level of expression of these polypeptides or a complex of these polypeptides in a sample. In addition a kit can contain control samples that contain known amounts of a Humanin, Bax, or Bid polypeptide and, if desired, a second antibody specific for the anti-Humanin, anti-Bax, or anti-Bid antibody.

The contents of the kit of the invention, for example, antibodies, are contained in packaging material, preferably to provide a sterile, contaminant-free environment. In addition, the packaging material contains instructions indicating how the materials within the kit can be employed both to detect the presence or absence of a particular Humanin, Bax, or Bid polypeptide or complex or to diagnose the presence of, or a predisposition for a condition associated with the presence or absence of these polypeptides or complexes such as Alzheimer's disease. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

The invention also provides a method of treating a pathology characterized by the presence, absence, increased or decreased amount of a Humanin-Bax or Humanin-Bid complex by administering to an individual an effective compound, for example, a Humanin-like compound, determined using the methods of the invention described above for identifying effective compounds.

The effective compounds of the invention described herein can optionally be formulated together with a pharmaceutically acceptable carrier for delivery to a cultured cell or to a subject. Suitable pharmaceutically acceptable carriers are well known in the art and include, for example, aqueous or organic solvents such as physiologically buffered saline, glycols, glycerol, oils or injectable organic esters. A pharmaceutically acceptable carrier can also contain a physiologically acceptable compound that acts, for example, to stabilize or increase the solubility of a pharmaceutical composition. Such a physiologically acceptable compound can be, for example, a carbohydrate, such as glucose, sucrose or dextrans; an antioxidant, such as ascorbic acid or glutathione; a chelating agent; a low molecular weight polypeptide; or another stabilizer or excipient. Pharmaceutically acceptable carriers, including solvents, stabilizers, solubilizers and preservatives, are described, for example, in Martin, *Remington's Pharm. Sci.,* 15th Ed. (Mack Publ. Co., Easton, 1975).

Those skilled in the art can formulate the therapeutic molecules to ensure proper distribution in vivo. For example, the blood-brain barrier (BBB) excludes many highly hydrophilic compounds. To ensure that the effective compounds of the invention cross the BBB, if desired, they can be formulated, for example, in liposomes, or chemically derivatized. For a review of strategies for increasing bioavailability of polypeptide drugs in the brain, and of methods for determining the permeability of polypeptides through the BBB using in vitro and in vivo assays, see Engleton et al., *Peptides* 9:1431-1439 (1997). Strategies that have been successfully used to increase the permeability of other neuropeptides through the BBB are particularly contemplated. For example, modifying the opioid polypeptide analgesic Met-enkephalin with D-penicillamine at two positions, forming a disulfide bridge that conformationally constrains the polypeptide, increases its stability towards BBB endothelial cell proteases and its BBB permeability. Likewise, linking two enkephalin polypeptides, each containing a D-amino acid residue at the second position, with a hydrazide bridge, results in a metabolically stable polypeptide with improved brain penetration. Additionally, halogenation of an enkephalin polypeptide has been shown to increase its BBB permeability. Additional modifications to a polypeptide of the invention that can increase its BBB penetration include conjugating the peptide to a lipophilic moiety, such as a lipophilic amino acid or methyldihydropyridine. Similar modifications to invention polypeptides or peptidomimetics are likewise expected to be advantageous.

Methods of ensuring appropriate distribution in vivo can also be provided by rechargeable or biodegradable devices, particularly where gradients of concentrations of drug in a tissue are desired. Various slow release polymeric devices are known in the art for the controlled delivery of drugs, and include both biodegradable and non- degradable polymers and hydrogels. Those skilled in the art understand that the choice of the pharmaceutical formulation and the appropriate preparation of the composition will depend on the intended use and mode of administration.

The effective compounds of the invention can be administered to a subject by any effective route. Suitable routes for delivering the therapeutic molecules of the invention include topically, intraocularly, intradermally, parenterally, orally, intranasally, intravenously, intramuscularly, intraspinally, intracerebrally and subcutaneously. The present invention also provides compounds containing an acceptable carrier such as any of the standard pharmaceutical carriers, including phosphate buffered saline solution, water and emulsions such as an oil and water emulsion, and various types of wetting agents.

An effective dose of an effective compound of the invention can be determined, for example, by extrapolation from the concentration required for in the binding or Bax activity assays described herein; or from the dose required to modulate cell proliferation. An effective dose of an effective compound of the invention for the treatment of a pathology can also be determined from appropriate animal models, such as transgenic mice. Transgenic mice that over-express beta amyloid are known to exhibit cognitive defects similar to those seen for Alzheimer's patients. An effective dose for treating this disease is a dose that results in either partial or complete reversal of cognitive skills as assayed by several known behavioral assays. Animal models for pathologies such as tumors are well-known in the art. An effective dose for treating this disease is a dose that results in either partial or complete regression of the tumor, reduction in metastasis, reduced discomfort, or prolonged life span. The appropriate dose for treatment of a human subject with a therapeutic molecule of the invention can be determined by those skilled in the art, and is dependent on the nature and bioactivity of the particular compound, the desired route of administration, the gender, age and health of the individual, the number of doses and duration of treatment, and the particular condition being treated.

In addition the invention provides a method of prolonging the in vivo survival of transplanted cells for the treatment of a disease or pathological condition. The method includes increasing the amount or stability of a Humanin-Bax or Humanin-Bid complex in a population of cells and transplanting the population of cells into a subject. Diseases or pathological conditions can include, for example, neurodegenerative diseases, cancer and virus-infected cells.

Cell transplantation is now being explored for the treatment of certain diseases, including Parkinson's and Alzheimer's diseases. For example, potential therapies in animal models of Parkinson's disease have included cell transplantation of genetically modified fibroblasts, which produce L-DOPA in the vicinity of the substantia nigra. Although the results of these experiments have been encouraging, the survival time of the transplanted cells is limited and, therefore, results in only a temporary and minor improvement of the condition.

Transplantation of fetal brain cells, which contain precursors of the dopaminergic neurons, has also been examined as a potential treatment for Parkinson's disease. In animal models and in patients with this disease, fetal brain cell transplantations have resulted in the temporary reduction of motor abnormalities. Furthermore, it appears that the implanted fetal dopaminergic neurons form synapses with surrounding host neurons. However, the transplantation of fetal brain cells is again limited due, for example, to the limited survival time of the implanted neuronal precursors.

In the specific case of Parkinson's disease, intervention by increasing the amount or stability of a Humanin-Bax or Humanin-Bid complex can improve the in vitro and in vivo survival of fetal and adult dopaminergic neurons, their precursors and dopamine-secreting fibroblasts and, thus, can provide a more effective treatment of this disease. Likewise, improved in vivo survival of essentially any cell type to be transplanted will improve the treatment of that disease. For example, neuronal cells or their precursors can be used for the treatment of other neurodegenerative diseases such as Alzheimer's disease and glutamate-induced neuronal cell death by enhancing the in vivo survival of cells.

Cells to be transplanted for the treatment of a particular disease can be genetically modified in vitro so as to increase the amount or stability of a Humanin-Bax or Humanin-Bid complex. Vectors used for transfecting cells ex vivo include adenovirus vectors and adeno-associated virus 2 vectors. Such methods are known within the art and are essentially the same as those described above, except that an increased amount or stability of a Humanin-Bax or Humanin-Bid complex is first achieved within the cells in vitro.

The invention further provides a mitochondrial-derived Humanin polypeptide having substantially the same sequence as in SEQ ID NO:3 and encoded by a nucleotide sequence substantially the same as that shown in SEQ ID NO:1. The Humanin polypeptide has been published as the 24 amino acid sequence shown in FIG. 4B (SEQ ID NO:2). The invention provides evidence, as shown in FIG. 4C, that Humanin is transcribed in mitochondria. As described in Example IV, RNA from mitochrondia was used as a template for an RT-PCR assay. Using primers specific for Humanin, a product corresponding to Humanin was detected and sequenced. Based on this finding, and the mitochondrial genetic code, the invention provides a mitochondrial-derived Humanin polypeptide comprising the 21 amino acid sequence shown in FIG. 4B (SEQ ID NO:3).

Exceptions to the universal genetic code occur in the mitochondria from several species (see Osawa et al., *Microbiol Rev.* 56:229-264 (1992)). A common change is that UGA has the same meaning as UGG, and therefore represents tryptophan instead of termination. This change is found in yeasts, invertebrates and vertebrates, but not in plants. Other changes are characteristic for particular organisms. Table I shows codon usage in the vertebrate mitochondrial genetic code.

Based on the differences in the genetic code in mitochondria, Humanin translated in mitochondria is predicted to contain one amino acid difference compared to the published Humanin polypeptide. As shown in FIG. 4, Humanin translated in the mitochondria (mtHumanin) is predicted to contain a methionine (M) at residue 16 instead of an isoleucine (I) as found in the published form of Humanin. In addition, the mitochondrial form of Humanin is predicted to lack the three amino acid sequence arginine (R)- arginine (R)-alanine (A) at the carboxyl-terminus of the polypeptide due to termination before this sequence. Since Humanin can be transcribed in mitochondria, the mitochondrial-derived form of Humanin can be considered a biologically relevant form of Humanin.

TABLE I

Anti-codons in Vertebrate Mitochondria

| Amino Acid Anti-codon (codon) | | Amino Acid Anti-codon (codon) | | Amino Acid Anti-codon (codon) | | Amino Acid Anti-codon (codon) | |
|---|---|---|---|---|---|---|---|
| Phe (UUU) | GAA | Ser (UCU) | | Tyr (UAU) | GUA | Cys (UGU) | GCA |
| Phe (UUC) | | Ser UCC) | UGA | Tyr (UAC) | | Cys (UGC) | |
| Leu (UUA) | UAA | Ser (UCA) | | Stop (UAA) | | Trp (UGA) | UCA |
| Leu (UUG) | | Ser (UCG) | | Stop (UAG) | | Trp (UGG) | |
| Leu (CUU) | | Pro (CCU) | | His (CAU) | GUG | Arg (CGU) | |
| Leu (CUC) | UAG | Pro (CCC) | UGG | His (CAC) | | Arg (CGC) | UCG |
| Leu (CUA) | | Pro (CCA) | | Gln (CAA) | UUG | Arg (CGA) | |
| Leu (CUG) | | Pro (CCG) | | Gln (CAG) | | Arg (CGG) | |
| Ile (AUU) | GAU | Thr (ACU) | | Asn (AAU) | GUU | Ser (AGU) | GCU |
| Ile (AUC) | | Thr (ACC) | UGU | Asn (AAC) | | Ser (AGC) | |
| Met (AUA) | UAU | Thr (ACA) | | Lys (AAU) | UUU | Stop (AGA) | |
| Met (AUG) | | Thr (ACG) | | Lys (AAG) | | Stop (AGC) | |
| Val (GUU) | | Ala (GCU) | | Asp (GAU) | | Gly (GGU) | GUC |

TABLE I-continued

Anti-codons in Vertebrate Mitochondria

| Amino Acid Anti-codon (codon) | Amino Acid Anti-codon (codon) | Amino Acid Anti-codon (codon) | Amino Acid Anti-codon (codon) |
|---|---|---|---|
| Val (GUC) | Ala (GCC) | Asp (GAC) | Gly (GGC) |
| UAC | UGC | | UCC |
| Val (GUA) | Ala (GCA) | Glu (GAA) | Gly (GGA) |
| | | UUC | |
| Val (GUG) | Ala (GCG) | Glu (GAG) | Gly (GGG) |

The invention provides an isolated polypeptide containing the amino acid sequence designated as SEQ ID NO:3, or a functional fragment thereof, where the fragment contains the methionine at position 16 of SEQ ID NO:3. A functional fragment of SEQ ID NO:3 can be a fragment with the ability to bind to Bax or Bid or the ability to be used as an immunogen to generate anti-Humanin antibodies. Fragments can include, for example, amino terminal, carboxyl terminal, or internal deletions of SEQ ID NO:3 where the fragment contains the methionine at position 16 of SEQ ID NO:3. For example, a fragment can contain at least about 6, 8, 10, 12, 14, 16, 18, or 20 contiguous or non-contiguous amino acid residues of SEQ ID NO:3 where the fragment contains the methionine at position 16 of SEQ ID NO:3. Examples of fragments that contain 8 contiguous amino acid residues of SEQ ID NO:3 where the fragment contains the methionine at position 16 include, for example, LLLLTSEM, LLLTSEMD, LLTSEMDL, LTSEMDLP, TSEMDLPV, and SEMDLPVK. In addition, various molecules or moieties, such as other polypeptides, carbohydrates, lipids or small molecules can be attached to SEQ ID NO:3 including the fragments of SEQ ID NO:3 where the fragment contains the methionine at position 16 of SEQ ID NO:3.

The invention also provides an isolated polypeptide containing the amino acid sequence designated as SEQ ID NO:3, or a functional fragment thereof, where the fragment contains the methionine at position 16 of SEQ ID NO:3, and where the polypeptide has been modified, for example, where non-natural amino acids have been substituted for one or more amino acids. A modification of a polypeptide can include non-naturally occurring derivatives, analogues and functional mimetics thereof generated by, for example, chemical synthesis. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-imbenzylhistidine. Also included as derivatives or analogues are those polypeptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds.

The invention further provides an isolated polypeptide containing the amino acid sequence designated as SEQ ID NO:3, or a functional fragment thereof, where the fragment contains the methionine at position 16 of SEQ ID NO:3, and where the isolated polypeptide contains a targeting molecule or moiety. A targeting molecule is a molecule that can be attached to a Humanin polypeptide of the invention that preferentially directs the polypeptide to a certain region of a cell or to a certain organ or site within the body. For example, the mitochondrial-derived Humanin polypeptide can be fused to the human immunodeficiency virus (HIV) tat polypeptide or to the Drosophila antennapedia membrane penetrating polypeptide sequence in order to target the mitochondrial-derived Humanin polypeptide to a cellular membrane. In addition, for example, a polypeptide such as PKKKRKV (SEQ ID NO:10) from SV40 T antigen is sufficient to cause nuclear import of a cytoplasmic polypeptide to which it is linked. Several targeting molecules are known in the art for targeting different locations within a cell.

In addition, targeting molecules and methods of identifying targeting molecules, are known in the art for preferentially directing polypeptides or other molecules to different organs in the body (see, for example, U.S. Pat. Nos. 6,068,829, 6,232,287, and 6,296,832). For example, a mitochondrial-derived Humanin polypeptide can be expressed as a fusion protein with a polypeptide such as CNSRLHLRC (SEQ ID NO:11) or VLREGPAGG (SEQ ID NO:12), as disclosed in U.S. Pat. No. 6,296,832, which can be used to target the brain. Other polypeptides such as antibodies or antibody fragments can also be used to target a Humanin polypeptide of the invention to a particular site in the body. Methods for generating fusion proteins are well known in the art (see, for example, Sambrook et al., supra, 1989; Ausubel et al., supra, 1999).

An isolated mitochondrial-derived polypeptide or a functional fragment thereof, containing a targeting molecule can be used to target Humanin to sites in the body where Humanin can be beneficial. For example, Humanin can be targeted to a neurological plaque or tangle region in the brain of an Alzheimer's disease patient. In addition, for example, Humanin can be targeted to any region of the body where Bax or Bid-induced apoptosis is occurring inappropriately.

The invention further provides an isolated polypeptide containing the amino acid sequence designated as SEQ ID NO:3, or a functional fragment thereof, where the fragment contains the methionine at position 16 of SEQ ID NO:3, and where the isolated polypeptide contains a detection molecule or moiety. A detection moiety is a moiety that is detectable external to a cell, tissue, or subject to which it is administered and, thus, can be useful for performing a diagnostic study. Typical detection moieties include radioactive molecules or fluorescent molecules. A diagnostic study can be performed in vivo, in situ, or in vitro. For example, a diagnostic study can be performed in a subject, a tissue slice or biopsy sample, cell culture, or in a test tube. An isolated mitochondrial-derived Humanin polypeptide of the invention linked to a detection moiety can be used, for example, in a binding assay to determine the amount of Bax or Bid in a cell extract that is capable of binding Humanin.

The invention further provides antibodies that specifically bind to the mitochondrial-derived form of Humanin designated as SEQ ID NO:3, or a functional fragment thereof, where the fragment contains the methionine at position 16 of SEQ ID NO:3. In addition, the invention provides antibodies that bind to the mitochondrial-derived form of Humanin designated as SEQ ID NO:3, but do not bind to the cytosolic form of Humanin designated as SEQ ID NO:2. Furthermore, the invention provides functional fragments of these antibodies. As used herein, the term "functional fragment" when used in reference to an antibody is intended to refer to a portion of an antibody which still retain some or all of the Humanin binding activity. Such functional fragments can include, for example, antibody functional fragments such as Fv, single chain Fv (scFv), Fab, F(ab'), F(ab)2, F(ab')2, and minibody. Other functional fragments can include, for example, heavy or light chain polypeptides, variable region polypeptides, CDR polypeptides, single domain antibodies, or portions thereof so long as such functional fragments retain binding activity.

Antibodies that bind to Humanin can be used in diagnositic and therapeutic methods. For example, a Humanin antibody can be labeled with a detection moiety and used to detect the presence, absence or amount of Humanin in vivo, in vitro, or in situ. Detection of the presence, absence or amount of Humanin at a site in the body can be useful in the diagnosis of certain diseases. For example, a decreased amount or lack of Humanin can be diagnostic of a disease such as Alzheimer's disease. Alternatively, the presence or an increased amount of Humanin can be diagnostic of a disease such as cancer where beneficial apoptosis has been blocked. In addition, a Humanin antibody can be labeled with a therapeutic moiety such as chemotherapeutic agent and used, for example, to treat a tumor that over-expresses Humanin. Therapies directed to increasing the amount of Humanin in a disease can be achieved by linking the Humanin polypeptide to a targeting molecule and directing Humanin to a particular disease site in the body as described further above.

A moiety, such as a fluorescent molecule, can be linked to a polypeptide, including an antibody, of the invention at any location within the polypeptide. For example, the moiety can be linked to the carboxyl terminus of the polypeptide, the amino terminus of the polypeptide, or at an internal site in the polypeptide. In addition, more than one moiety can be linked to the same polypeptide, for example, a moiety can be linked to the carboxyl terminus and another moiety, of the same or different type, can be linked to the amino terminus of the polypeptide.

Chemistries used for the linkage of various moieties to polypeptides are well known in the art. A moiety such as detection moiety can be linked to a polypeptide, including an antibody, of the invention using, for example, carbodiimide conjugation (Bauminger and Wilchek, *Meth. Enzymol.* 70:151-159 (1980)). Carbodiimides comprise a group of compounds that have the general formula R—N═C═N—R', where R and R' can be aliphatic or aromatic, and are used for synthesis of polypeptide bonds. The preparative procedure is simple, relatively fast, and is carried out under mild conditions. Carbodiimide compounds attack carboxylic groups to change them into reactive sites for free amino groups. Carbodiimide conjugation has been used to conjugate a variety of compounds to carriers for the production of antibodies. The water soluble carbodiimide, 1-ethyl-3-(3-dimethylaminopropyl) carbodiimide (EDC) is useful for conjugating a moiety to a polypeptide, including an antibody of the invention.

In addition to using carbodiimides for the direct formation of polypeptide bonds, EDC also can be used to prepare active esters such as N-hydroxysuccinimide (NHS) ester. The NHS ester, which binds only to amino groups, then can be used to induce the formation of an amide bond with the single amino group of the doxorubicin. The use of EDC and NHS in combination is commonly used for conjugation in order to increase yield of conjugate formation (Bauminger and Wilchek, supra, 1980). Other methods of conjugating moieties to a polypeptide include, for example, sodium periodate oxidation followed by reductive alkylation of appropriate reactants and glutaraldehyde crosslinking. However, it is recognized that, regardless of which method of producing a polypeptide-moiety conjugate of the invention is selected, a determination must be made that the polypeptide or antibody maintains its selectivity and that the moiety maintains its relevant function.

The yield of polypeptide-moiety conjugate formed is determined using routine methods. For example, HPLC or capillary electrophoresis or other qualitative or quantitative method can be used (see, for example, Liu et al., *J. Chromatoqr.* 735:357-366 (1996); Rose et al., *J. Chromatoqr.* 425: 419-412 (1988)). In particular, the skilled artisan will recognize that the choice of a method for determining yield of a conjugation reaction depends, in part, on the physical and chemical characteristics of the specific moiety. Following conjugation, the reaction products are desalted to remove any free polypeptide and free drug.

In one embodiment, a detection moiety such as a radioactive or fluorescent molecule can be linked to an antibody of the invention in order to diagnose, predict, prevent, or monitor diseases involving Humanin or Humanin-deficiency. A diagnostic study can be performed in vivo, in situ, or in vitro. For example, a diagnostic study can be performed in a subject, a tissue slice or biopsy sample, cell culture, or in a test tube.

An antibody of the invention labeled with a detection moiety can be used to detect the presence, absence or amount of Humanin in a subject or in a sample from a subject using methods known to one skilled in the art. For example, a moiety such as a gamma ray emitting radio-nucleotide, for example, indium-111 or technitium-99, can be linked to an antibody of the invention. For in vivo diagnostic studies, this conjugate can be administered to a subject and detected using a solid scintillation detector. Similarly, a positron emitting radionucleotide such as carbon-11 or a paramagnetic spin label such as carbon-13 can be linked to a polypeptide of the invention and, following administration to a subject, the localization of the detection moiety can be detected using positron emission transaxial tomography or magnetic resonance imaging, respectively (van Roggen et al., *Curr. Opin. Rheumatol.* 12:77-83 (2000); Stubbs et al., *Acta Oncol.* 38:845-853 (1999); Ikeda et al., *Topics Maqn. Reson. Imaqinq* 10:143-151 (1999); Parker et al., *Topics Magn. Reson. Imaging* 10:130-142 (1999)). A detection moiety can also be, for example, a MRI contrast dye or a fluorescent agent.

An antibody of the invention labeled with a detectable moiety also can be used to detect the presence, absence or amount of Humanin in a sample derived from a subject. For example, a labeled antibody can be bound to a tissue slice for example, from a tumor biopsy or a post-mortem brain. In addition, for example, a labeled antibody can be used to detect Humanin using any standard immunological assay, for example, an ELISA assay or immunoprecipitation assay. Since a Humanin antibody bound to Humanin is a protein:

protein complex, several of the methods described further above, such as a biomolecular interaction analysis (BIA) and fluorescence polarization assay (FPA) can be used to detect Humanin using a labeled antibody.

A detection moiety linked to a polypeptide of the invention can be used to diagnose, predict, prevent, or monitor diseases involving Humanin or Humanin-deficiency. For example, a Humanin antibody linked to a detection moiety can be used to detect the presence, absence or amount of Humanin in a subject or a sample from a subject in order to diagnose Alzheimer's disease or a tumor that over-expresses Humanin. In addition, the presence, absence or amount of Humanin can be used to predict, and therefore possibly prevent, a disease involving Humanin. Furthermore, labeled antibodies to Humanin can be used to monitor the progress of treatment, for example to determine if the amount of Humanin is decreased in a tumor after treatment.

In another embodiment, an antibody of the invention can contain a therapeutic moiety. A therapeutic moiety can include, for example, a cytotoxic agent, including a chemotherapeutic agent or a radioactive agent, an anti-antigenic agent, a pro-angiogenic agent, and an agent that promotes tissue repair. Cytotoxic chemotherapy or radiation therapy is the basis of the systemic treatment of disseminated malignant tumors. However, a limitation of the currently used cytotoxic agents is that these agents have a narrow therapeutic index. As such, the dose of these cytotoxic agents generally is limited by undesirable toxicity. However, coupling of an antibody of the invention to a cytotoxic agent can effectively increase the concentration of the cytotoxic agent at a site of Humanin over-expression, such as a tumor, and reduce side effects associated with the presence of the toxic agent in other tissues.

Chemotherapeutic agents include, for example, anthracyclins, alkylating agents, vinca alkaloids, nucleotide analogs, cis-platinum, doxoribicin, methotrexate and mitomycin C. A chemotherapeutic agent useful in the invention can be, for example, an anthracyclin such as doxorubicin, which is a commonly used cancer chemotherapeutic agent and is useful for treating breast cancer (Sivam et al., *Cancer Res.* 55:2352-2356 (1995); Lau et al., *Bioorg. Med. Chem.* 3:1299-1304 (1995); Shih et al., *Cancer Immunol. Immunother.* 38:92-98 (1994); Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, supra, 1997; Steiner, In "Angiogenesis: Key principles-Science, technology and medicine," pp. 449-454 (eds. Steiner et al.; Birkhauser Verlag, 1992)), which can contribute to its effectiveness in treating cancer. Other anthracyclins, including idarubicin and daunorubicin, also can be linked to an antibody of the invention and delivered effectively to angiogenic vasculature (Rowland et al., *Cancer Immunol. Immunother.* 37:195-202 (1993); Aboud-Pirak et al., *Biochem. Pharmacol.* 38:641-648 (1989)).

The polypeptides and antibodies of the invention described herein can optionally be formulated together with a pharmaceutically acceptable carrier for delivery to a cultured cell or to a subject as described further above. Pharmaceutically acceptable carriers, including solvents, stabilizers, solubilizers and preservatives, are described, for example, in Martin, supra, 1975. As described above those skilled in the art can formulate the therapeutic molecules to ensure proper distribution in vivo. For example, strategies for increasing the bioavailability of polypeptide drugs in the brain, and methods for determining the permeability of polypeptides through the BBB using in vitro and in vivo assays can be found in Engleton et al. supra, 1997. In addition, the polypeptides and antibodies of the invention can be administered to a subject by any effective route such as, for example intravenously, intraspinally, intracerebrally and subcutaneously. Furthermore, an effective dose of a polypeptide or antibody of the invention can be determined, for example, by extrapolation from appropriate animal models, such as transgenic mice.

The invention also provides nucleic acid molecules encoding variants of the Humanin nucleotide sequence (SEQ ID NO:1) and polypeptides encoded by these nucleic acid molecules. As described above, the inventors have identified about 30 copies of the Humanin nucleotide sequence, some identical to SEQ ID NO:1 and some with small modifications compared to SEQ ID NO:1, in the human genome. Humanin polypeptide variants expressed from these genomic sequences can be used in the methods of the invention.

The following examples are intended to illustrate but not limit the present invention.

EXAMPLE I

Identification of Humanin as Bax Binding Target Using a Yeast Two-Hybrid Screening Assay A yeast two-hybrid screening assay was performed to identify polypeptides that interact with an apoptotically-inactive mutant form of Bax. A yeast two-hybrid system is designed to screen a cDNA library for a gene encoding a polypeptide that interacts with a known target (bait) polypeptide (Golemis, et al., In Current Protocols in Molecular Biology, John Wiley & Sons, Inc., Ch.20.0 and 20.1.(1996); Mendelsohn and Brent, *Current Opinion in Biotechnology* 5:482-486 (1994)). In this experiment, a S184K (a serine at position 184 in the transmembrane domain mutated to a lysine) mutant of mouse Bax was used as a bait, since the wild type Bax induces cell death in yeast. The S184K mutant human Bax does not localize to mitochondria and does not induce apoptosis (Mechushtan et al., *EMBO Journal* 18(g): 2330-2341 (1999)).

Bax (S184K) cDNA was constructed in a pgilda yeast expression vector at EcoRV XhoI sites, producing a LexA-Bax fusion polypeptide. The prokaryotic LexA polypeptide, which functions as the DNA binding domain and binds to LexA operators, was used. A human adult testes cDNA library in a pYESTrp vector was purchased from Invitrogen. This library contains library cDNA fused with a B42 transcription activation domain (an 88-residue acidic *E. coli* peptide). The pGilda-Bax (S184K) and cDNA library plasmids were co-transfected into EGY48 yeast cells together with a reporter plasmid pSH18-34. The transformants were cultured on leucine-deficient galactose-containing media, which induces gene expression through the GAL1 promoter located within both the pGilda and pYESTrp vectors. Since the Leu-auxotrophic host EGY48 can not grow on Leu-deficient media, only the clones that contain Bax binding polypeptides (which binds to Bax and brings B42 and LexA into close proximity activating the LEU2 reporter gene) can grow and form colonies.

A total of 19 positive colonies were identified. To eliminate the false positives, a subsequent LacZ filter assay was performed. When B42 and LexA were brought into close proximity, they also activate the transcription of LacZ reporter in the pSH18-34 plasmid. The cells produced b-galactosidase and turned blue in LacZ filter assay. All 19 clones tested positive. When the plasmids were isolated from the yeast clones and sequenced, one of these clones contained a cDNA that encoded Humanin (Hashimoto, et al. supra 2001). The interaction between Humanin and Bax was further confirmed by co-transfection into EGY48 cells. Yeast cells expressing both pGilda-Bax (S184K) and pYESTrp-Humanin grew on Leu-media, while cells contain either Bax (S184K) or Humanin alone did not grow.

EXAMPLE II

Interaction of Humanin and Bax: Co-immunoprecipitation and Cellular Co-localization The following experiments confirm an interaction between Humanin and Bax. Similar experiments were performed to confirm an interaction between Humanin and Bid.

Humanin (HN) cDNA was sub-cloned into a Green Fluorescence Protein (GFP) expression vector GFP-C1 at the Xhol/Hind III sites, producing a GFP-HN fusion polypeptide. GFP and GFP-HN were transfected into 293T cells with pcDNA3-HA-Bax. Cell lysates from these cells were immunoprecipitated with anti-GFP antibody and subsequently blotted with anti-HA antibody. The lysates were also blotted with ani-GFP antibody to confirm polypeptide expression. Humanin was found to co-immunoprecipitate with Bax. The data shown were obtained using the cytosolic form of Humanin; however, both cytosolic and mitochondrial forms of Humanin were tested and the results were the same.

GFP-HN and a Red Fluorecence Protein (RFP) vector, RFP-Bax, were transfected into Cos-7 cells. The intracellular localization of the expressed polypeptides was examined using a confocal microscope. As a control, GFP and RFP alone were shown to localize diffusely inside the cells. GFP-HN localized to punctate intracellular membranes and when GFP-HN and RFP-Bax were co-expressed, the two polypeptides co-localized to intracellular membranes (data not shown).

EXAMPLE III

Expression of Humanin in Mitochondria

Mitochondria were isolated from $5 \times 10^6$ 293T cells using differential centrifugation. RNA was then isolated from the mitochondria using TriZol reagent (Gibco-BRL). The RNA was subjected to reverse transcription using an oligo-dT primer. The products of the reverse transcription reaction were digested with RNaseH and RNase A to remove any RNA. The remaining cDNA was used as a template for PCR reaction with primers specific for Bax, Humanin, NADHD and COX.

As seen in FIG. 3C, a product was detected for NADHD and COX which are known mitochondrial genes and no product was detected for Bax which is a cytosolic gene. However, a product was detected when using the Bax primers and a pcDNA3-Bax template demonstrating that the Bax primers are capable of generating a product. When using primers for Humanin with the mitochondrial cDNA, a product of the correct size was detected. The Humanin product was excised and sequenced and the sequence matched the published Humanin sequence (SEQ ID NO:1).

The PCR conditions used in this example were: initial denaturing at 95° C. for 30 seconds then 30 cycles of denaturing at 95° C., 30 seconds; annealing at 55° C., 30 seconds; and extension at 72° C., 1 minute; followed by final extension at 72° C., 5 minutes then hold at 4° C. The sequence of the forward (F) and reverse (R) primers used in the PCR reactions and the size of the expected PCR products are listed below.

For NADH the expected product size was 230 base pairs and the primers were NADHF CCTCATTGTACCCAT-TCTAATCGC (SEQ ID NO: 13) and NADHR GTAGAA-GAGCGATGGTGAGAGC (SEQ ID NO: 14). For COX the expected product size was 377 base pairs and the primers were COXF CTCCCTCTCTCCTACTCCTGCTCG (SEQ ID NO: 15) and COXR GGTATAGAATGGGGTCTCCTC-CTCC (SEQ ID NO: 16). For Humanin the expected product size was 75 base pairs and the primers were HNF ATGGCTC-CACGAGGGTTC (SEQ ID NO: 17) and HNR TTATGC-CCGCCTCTTCAC (SEQ ID NO: 18). For Bax the expected product size was 576 base pairs and the primers were BAXF ATGGACGGGTCCGGG (SEQ ID NO: 19) and BAXR TCAGCCCATCTTCTTCCAG (SEQ ID NO: 20). In addition, the sequence of primers used for making the mitochondrial form of Humanin cDNA were: BGHNF1 GGCTC-GAGATGGCTCCACGAGGGTTC (SEQ ID NO: 21) and BGHNI16MR GGAAGCTTACTTCACGGGCAGGTC-CATTTC (SEQ ID NO: 22).

EXAMPLE IV

Humanin Inhibition of Apoptosis

Rat neuronal cell line CSM14.1 cells were transfected with various plasmids using the Lipofectamine reagent (Invitrogen). For transfection, $10 \times 10^5$ cells were plated per well using 6 well plates. Each well received 1 µg DNA plus 4 ml of Lipofectamine. After 24 hours of transfection, the percentage of cell death was determined using 4'-6-diamidino-2-phenylindole (DAPI) staining. As seen in FIG. 4, Humanin decreased both Bax- and Bid-induced apoptosis. However, a mutant form of Humanin where the cysteine at position 8 was mutated to an alanine, was not able to decrease Bax- or Bid-induced apoptosis. The data shown were obtained using the cytosolic form of Humanin; however, both cytosolic and mitochondrial forms of Humanin were tested and the results were the same.

The mutant form of Humanin where the cysteine at position 8 was mutated to an alanine (C8A) was made by direct PCR using primers containing the desired mutation. The sequence of primers used for the C8A mutant were: BGXHOC8AF GGCTCGAGGAATGGCTCCAC-GAGGGTTCAGCGCTC (SEQ ID NO: 23) and BGHNR GGAAGCTTTTATGCCCGCCTCTTCAC (SEQ ID NO: 24).

EXAMPLE V

Humanin Binds Bax in Human Cells and Mouse Testis Lysates

This example shows the ability of Humanin to interact with Bax in human cells, and additionally shows that Humanin does not bind to Bcl-2, Bcl-XL, Bak, Bcl-B, Mcl-1, and Bok. Furthermore, this example shows that endogenous Humanin can interact with endogenous Bax in a mouse testis lysate.

Figure 5:
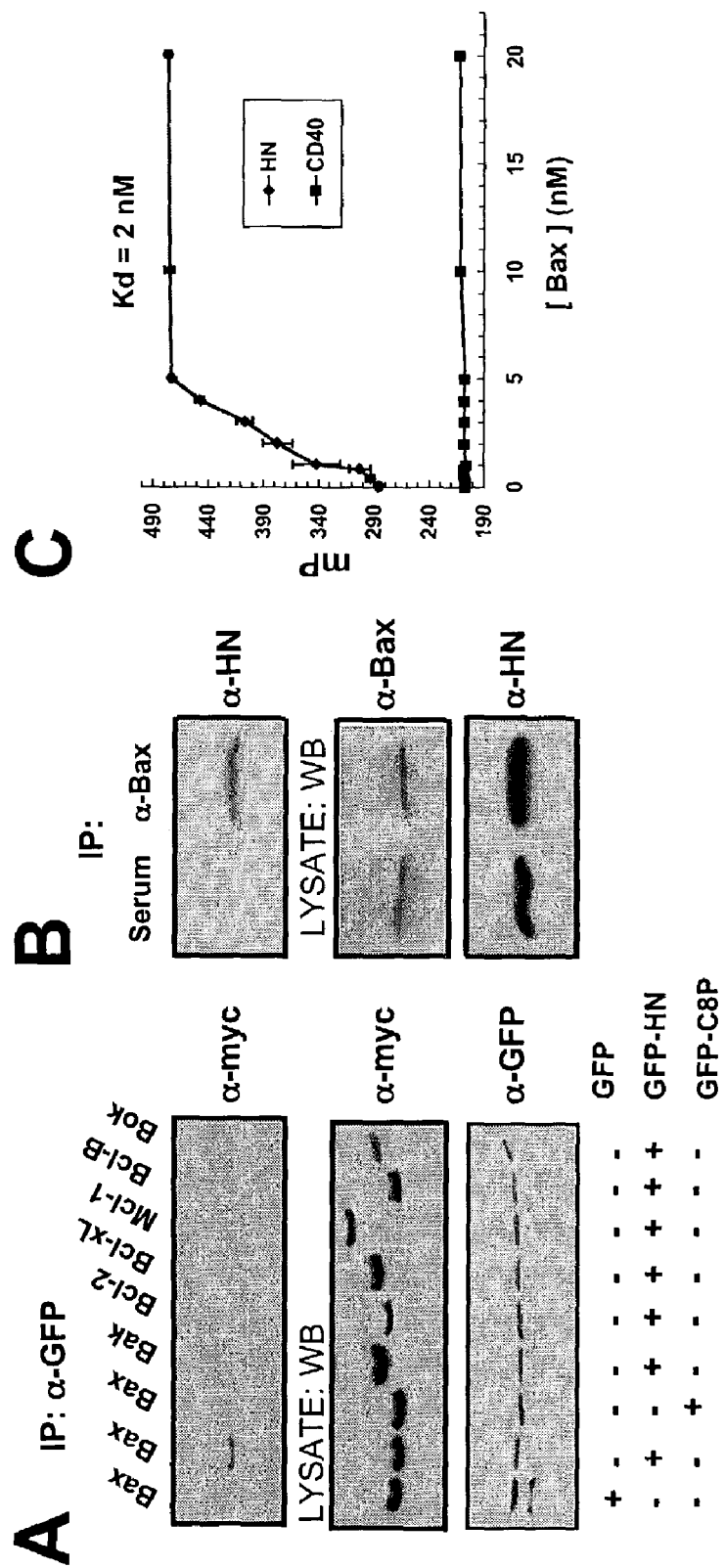
FIG. 5 shows the interaction between Humanin and Bax. (A) HEK293T cells were transfected with pcDNA3-myc plasmids encoding Bax or other Bcl-2 family proteins with GFP, GFP-HN, or GFP-HN(C8P). Cell lysates were immunoprecipitated with polyclonal anti-GFP antibody. The immunoprecipitates or the lysates were blotted with anti-myc or anti-GFP antibodies, respectively. The slower migrating form of GFP seen in lane 1 (asterisk)represents an alternative form of GFP produced from the wild-type (control) p-EGFP-Cl plasmid (http://clonotech.com). (B) Testes of three-week-old mice were homogenized in lysis buffer (0.1% Triton X-100, 50 mM Tris-HCl, pH7.5, 1 mM EDTA, plus protease inhibitor cocktail). The lysates were immunoprecipitated with control rabbit serum or polyclonal anti-mouse Bax antibody. The immunoprecipitates or the lysates were subjected to electrophoresis in Tris/Tricine gels (16% T, 3% C), electroblotted to PVDF membrane, and immunoblotted with polyclonal anti-HN antibody or monoclonal anti-Bax antibody 6A7 (Trevigen). (C) The affinity (Kd) of Bax/HN interaction was measured by fluorescence polarization assay, using various concentrations of purified recombinant Bax and 40 nM rhodamine-conjugated HN peptide. Control peptide from CD40 is also shown (mean +Std Dev; n=3).

Co-immunoprecipitation assays were performed using Humanin polypeptides expressed as fusion polypeptides with the Green Fluorescent Protein (GFP) in human cells. Wild-type Humanin fused to GFP is referred to as GFP-HN and a mutant form of Humanin, where the cysteine at position 8 is replaced with proline, fused to GFP is referred to as GFP-C8P. As shown in FIG. 5A, GFP-HN co-immunoprecipitated myc-tagged Bax from HEK293T cells, while GFP and GFP-HN (C8P) did not. Immunoblot analysis of lysates of the transfected cells confirmed production of all proteins. In addition, GFP-HN also coimmunoprecipitated endogenous Bax from cell lines, which contain relatively high levels of the Bax protein.

Furthermore, multiple Bcl-2 family proteins were surveyed for interactions with Humanin by coimmunoprecipitation experiments (FIG. 5A). GFP-HN did not co-immunoprecipitate with other Bcl-2 family proteins that are predicted to share structural similarity with Bax, including Bcl-2, Bcl-XL, Bak, Bcl-B, Mcl-1, and Bok.

Expression of endogenous Humanin has been demonstrated in the testis and colon of mice (Tajima et al., *Neurosci. Lett.* 324:227-231 (2002)). A rabbit polyclonal antibody raised against Humanin peptide (P04, gift of Dr. Ikuo Nishimoto) was used to examine whether endogenous Humanin peptide interacts with endogenous Bax polypeptide. As shown in FIG. 5B, Humanin can be co-immunoprecipitated together with Bax from the lysates of mouse testis. In addition, endogenous Humanin was determined to be a cytosolic protein, based on subcellular fractionation experiments.

Immunoblotting and immunoprecipitations were performed as follows. Immunoblotting was performed as described previously (Fields and Song, *Nature* 340:245-246 (1989)). For co-immunoprecipitations, cells were cultured in 50 uM benzocarbonyl Valine Alanine Asparate fluoromethylketone (zVAD-fmk) to prevent apoptosis. Cells were suspended in lysis buffer (50 mM Tris-HCl, pH7.4; 150 mM NaCl; 20 mM EDTA; 50 mM NaF; 0.5% NP-40; 0.1 mM Na3VO4; 20 ug/ml Leupeptin; 20 ug/ml Aprotinin; 1 mM DTT; and 1 mM PMSF). Lysates (200 ul diluted in 1 ml final volume of lysis buffer) were cleared by incubation with 15 ul of protein G-Sepharose 4B (Zymed) and then incubated with 15 ul of polyclonal antibody and 15 ul of protein G at 4° C. overnight. Beads were then washed 4 times with 1.5 mls lysis buffer before boiling in Laemmli sample buffer and performing SDS-PAGE/immunoblotting.

EXAMPLE VI

Fluorescence Polarization Assay (FPA)

This example demonstrates the binding of Humanin to Bax using a fluorescence polarization assay (FPA).

The binding of Humanin to Bax was further investigated using an in vitro binding assay. In this example, the in vitro binding assay is a fluorescence polarization assay (FPA). For this experiment, full-length Bax protein was produced in bacteria and purified. Various concentrations of Bax protein were incubated with 40 nM of rhodamine-conjugated synthetic purified Humanin peptide. The extent of peptide binding was then monitored by measuring polarization of monochromatic light passed through the sample, where peptide binding to the bulkier protein slows the rate of peptide tumbling in solution, enhancing the polarization effect. As shown in FIG. 5C, Bax bound rhodamine-HN in a concentration dependent and saturable manner, with an estimated Kd of 2 nM. In contrast, various control peptides of similar length, such as rhodamine-CD40 (residue 250P to 266G) did not display interactions with Bax in these fluorescence polarization assays. Recombinant Bcl-XL protein also did not bind rhodamine-HN, further confirming specificity.

Fluorescence Polarization Assays were performed as follows. Recombinant Bax protein was isolated from E. coli BL21 harboring pTYB1-Bax essentially as described (Suzuki et al., *Cell* 103:645-654 (2000)). For fluorescence polarization assays (FPA), various concentrations of Bax protein were incubated with 40 nM of rhodamine-conjugated synthetic purified Humanin peptide dissolved in water for 30 minutes in dark. Fluorescence polarization was measured using an AnalystTM AD Assay Detection System (LJL Biosystem, Sunnyvale, Calif.).

Peptides were synthesized as follows. Rhodamine-conjugated Humanin peptide was synthesized on MBHA resin and is amidated at the C-terminus. 1-aminohexanoic acid(ahx)-Humanin was initially prepared with an Advanced Chemtech 350 multiple peptide synthesizer using standard fluorenyl-methoxycarbonyl chemistry with DIC coupling (Atherton and Sheppard, *Solid-phase Synthesis,* Oxford Publishing Co., New York (1989)). Rhodamine B (Aldrich) was coupled to ahx-humanin using N—[(Dimethylamino0-1H-1,2,3-triazolo[4,5-b]pyridin-1-ylmethylene]—N-methylmethanaminium hexafluorophosphate N-oxide, 1-hydroxybenzotriazole hydrate, and Diisopropylethylamine and occasional sonication until the ninhydrin test was negative. The peptide was deprotected and cleaved from the resin, precipitated with ice-cold diethyl ether and purified by HPLC on a reverse-phase C18 Cosmosil column, eluted with a water-acetonitrile, 0.1% trifluoroacetic acid gradient and analyzed by matrix-assisted laser desorption/ionization (MALDI)-time-of-flight (TOF) mass spectrometry.

EXAMPLE VII

Effect of Humanin on Cell Death

This example demonstrates the effect of Humanin on cell death induced by several stimuli that are known to induce apoptosis, at least in part, through Bax-dependent mechanisms (Wei et al., *Science* 292:727-730 (2001)).

Figure 6:
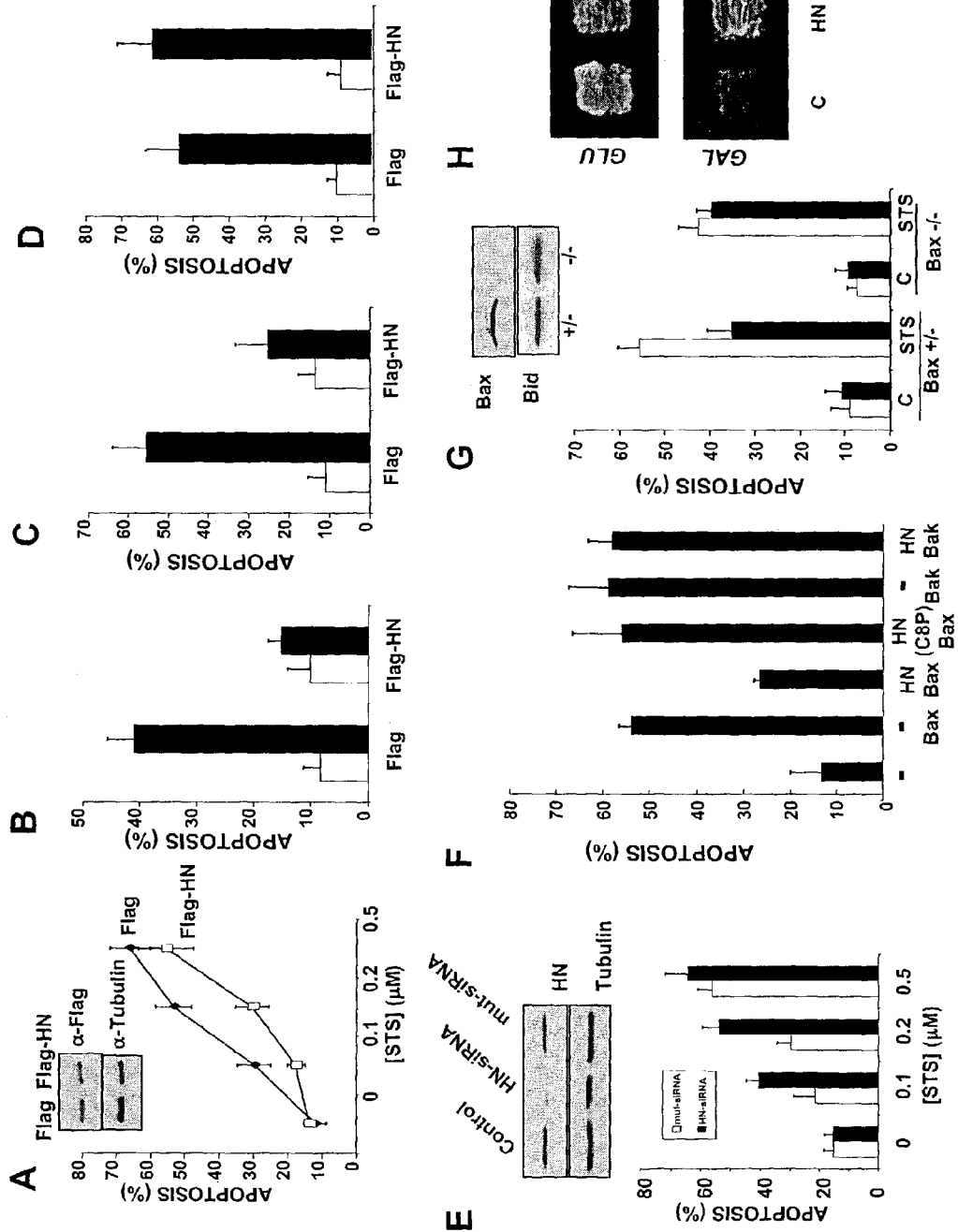
FIG. 6 shows Humanin can inhibit cell death induced by Bax. (A-D) CMS14.1 neuronal cells were transfected with plasmids encoding Flag-HN peptide or Flag-control (27-amino-acid) peptide, together with GFP-encoding plasmid at 4:1 ratio. Cells were either cultured without further treatment (open bars) or subjected to various apoptotic stimuli for various times (dark bars), including (A) STS for 8 h (dark symbols=Flag-control; open symbols=Flag-HN), (B) Serum-deprivation for 72 h, (C) 10 joules/m2 Uvirradiation followed by 24 h culture, and (D) 50 ng/ml TNFa in 1 μm CDDO for 24 h. Cells were then fixed and stained with DAPI to determine the percentage of apoptotic cells, evaluating=200 GFP-positive cells per sample (mean±SD; n=3). (inset) Lysates prepared from replicate cultures of transfected cells were normalized for total protein content and analyzed by immunoblotting using anti-Flag (top) and anti-tubulin (bottom) antibodies, confirming production of similar amounts of Flag-control and Flag-HN peptides. (E) SF268 cells were transfected with Humanin siRNA (HN-siRNA) (dark bars) or mutant siRNA containing two mismatches (mut-siRNA) as negative control (open bars). (Upper panel) After 72 hr, cell lysates were prepared and 100 ug was analyzed by immunoblotting using anti-HN and anti-tubulin (as a loading control) antibodies. (Lower panel) At 72 hr after siRNA transfection, SF268 cells were cultured with 0.1 μM STS for 8 hrs, then % apoptosis was determined (mean+std dev; n=3). (F) HN protects against Bax- but not Bak-induced apoptosis. CSM14.1 neuronal cells were co-transfected with pcDNA3-HA-Bax or pcDNA3-HA-Bak together with plasmids encoding with GFP (indicated by "-"), GFP-HN, or GFP-HN(C8P). Apoptosis (%) was measured 48 hrs later among GFP-positive cells. (G) Humanin inhibits STS-induced apoptosis in wild type HCT116 cells, but not HCT116 BAX -/- cells. HCT116 cells heterozygous or homozygous for BAX gene inactivation were transfected with plasmids encoding GFP (open bars) or GFP-HN (dark bars). After 24 h, cells were cultured without (C) or with STS (0.2 μM for wild type and 1.0 μM for Bax - /- cells) for 8 h, then % apoptosis was determined for GFP-positive cells (mean+std dev; n=3). (inset) Lysates from the cells were analyzed by immunoblotting (20 ug) using anti-Bax (top) and anti-Bid (bottom) antibodies. (H) HN prevents Bax-induced cell death in yeast. Cells were co-transformed with YEp51-Bax (encoding Bax under control of a GAL10 promoter) and plasmid control (C) or plasmids encoding Humanin or Humanin(C8P) fusion polypeptides. Cells initially grown in glucose-containing medium were streaked onto either glucose (top) or galactose (bottom) plates to suppress or induce Bax expression, respectively.

For these experiments, Flag-epitope tagged Humanin (Flag-HN) or Flag control polypeptides were expressed in CSM14.1 cells, an immortalized rat hippocampal neuronal cell line that has been used as a model for neuronal apoptosis studies (Kermer et al., *Cell Death Differ.* 9:405-413 (2002)). Apoptosis of CSM14.1 cells induced by Staurosporine (STS), UV-irradiation, and serum-deprivation was suppressed by Flag-HN (FIG. 6A-C). Conversely, apoptosis induced by a Bax-independent death stimulus, TNF, was not suppressed by Flag-HN (FIG. 6D). Note that at higher doses of STS (FIG. 6A), Humanin-mediated protection was overcome, indicating Humanin-insensitive mechanisms of apoptosis induction exist, even when using a mitochondria-dependent death stimuli.

Apoptosis assays were performed as follows. Both floating and adherent cells (after trypsinization) were collected 48 hr after transfection, fixed, and stained using 4',6-diamidine-2'-phenylindole dihydrochloride (DAPI) for assessing apoptosis based on nuclear fragmentation and chromatin condensation (Fields and Song, supra (1989)).

EXAMPLE VIII

Reduction of Humanin Using Small Interfering RNA (siRNA)

This example uses siRNA to demonstrate that endogenous Humanin can participate in cytoprotection.

Synthetic small interfering RNA (siRNA) (Elbashir et al., *Nature* 411:494-498 (2001)) was used to knock-down expression of endogenous Humanin in SF268 cells, a glioblastoma cell line that was empirically determined to contain high levels of endogenous Humanin peptide expression. As shown in FIG. 6E, transfection into SF268 cells of Humanin siRNA, but not a mutant siRNA containing two mismatches, reduced endogenous levels of Humanin peptide, as determined by immunoblotting, correlating with increased sensitivity to STS-induced apoptosis. Thus, endogenous Humanin can participate in cytoprotection.

Preparation and transfection of siRNA was performed as follows. Oligonucleotides with the following sequences were purchased from Qiagen: Humanin sense r(CCAGUGAAA-UUGACCUGCC)d(TT) [SEQ ID NO:25]; Humanin antisense r(GGCAGGUCAAUUUCACUGG)d(TT) [SEQ ID NO:26]; Humanin mutant sense r(CCGAUGAAAUUGAC-CUGCC)d(TT) [SEQ ID NO:27]; Humanin mutant antisense r(GGCAGGUCAAUUU.CAUCGG)d(TT) [SEQ ID NO:28] where "r" denotes a ribonucleotide sequence and "d" denotes a deoxynucleotide sequence. Complementary oligonucleotides were annealed by the manufacturer. The resulting double-strand RNAs were dissolved in sterile 100 mM potassium acetate, 30 mM HEPES-KOH, 2 mM magnesium acetate [pH 7.4] to final concentration of 20 μM. SF268 cells were cultured in 6-well plates in 2 ml DMEM media containing with 10% FBS. Cells were transfected at 40% confluency using a mixture of 10 μl of oligofectamine (Invitrogen) and 10 μl of siRNA (final concentration 100 nM) in serum-free media. Cells were rinsed with medium after 16 hours of incubation and cultured for 56 hours more before analysis.

EXAMPLE IX

Correlation Between Humanin binding to Bax and Humanin-mediated Suppression of Apoptosis This example shows a correlation between Humanin binding to Bax and suppression of apoptosis.

In order to explore whether a correlation exists between Humanin binding to Bax and Humanin-mediated suppression of apoptosis, Bax was co-expressed with various GFP-fusion polypeptides encoding wild-type, full-length Humanin or various truncation and site-specific mutants of Humanin (Table 1). Expression of all GFP-fusion polypeptides was confirmed by immunoblotting, and ability to bind Bax was determined by co-immunoprecipitation assay. Each Humanin mutant was scored for ability to suppress apoptosis induced by Bax over-expression by >50% using a 3:1 ratio of HN:Bax plasmid DNA. As shown in Table 1, a perfect correlation was observed between Bax-binding and suppression of apoptosis. Based on these studies, an active region of the 24 amino-acid Humanin peptide, mapped to residues 7-17. Two mutants within this region, C8P and L9R, previously were reported to lack anti-apoptotic activity when expressed in cells (Hashimoto et al., Proc Natl Acad Sci USA 98:6336-6341 (2001); Hashimoto et al., J. Neurosci, 21:9235-9245 (2001)). These Humanin mutants lacked Bax-binding activity and failed to protect against Bax-induced apoptosis, thus further confirming the correlation between binding to Bax and anti-apoptotic function of Humanin (Table 1).

TABLE 1

Analysis of Humanin Mutants: Correlation with Bax-binding and antiapoptotic function.

| HN Peptide | Bax binding | Bax suppression |
|---|---|---|
| 1-24 | + | + |
| 3-24 | + | + |
| 4-24 | + | + |
| 7-24 | + | + |
| 10-24 | − | − |
| 13-24 | − | − |
| 1-17 | + | + |

TABLE 1-continued

Analysis of Humanin Mutants: Correlation with Bax-binding and antiapoptotic function.

| HN Peptide | Bax binding | Bax suppression |
|---|---|---|
| 1-15 | − | − |
| 1-12 | − | − |
| 3-19 | + | + |
| 3-18 | + | + |
| 3-17 | + | + |
| C8P | − | − |
| L9R | − | − |
| GFP Only | − | − |

Plasmids were constructed as follows. A cDNA containing the ORF of Humanin without additional flanking sequences was generated by PCR using an EST clone encoding full-length Humanin as a template. The resulting PCR products were digested with restriction endonucleases and subcloned into the Xho I and Hind III sites of pEGFP-C1 and Xho I and EcoR I sites of pEGFP-N2 (Clontech). Truncation and site-specific mutants of Humanin were created by PCR.

Cell culture and transfections were performed as follows. CSM14.1, HCT116, Cos-7, and SF268 cells were cultured in DMEM high glucose media (Irvine Scientific, Santa Ana, Calif.) containing 10% fetal bovine serum (FBS). PC-3 cells were cultured with RPMI 1640 media containing 10% FBS. Transfection of cells was performed using SuperFect (Qiagen, Chatsworth, Calif.) or LipofectaminePLUS reagent (Nitrogen). CSM14.1 cells were cultured at 39° C. after transfection to inactive temperature-sensitive Large T antigen, as described (Kermer et al., Cell Death Differ 9:405-413 (2002)).

EXAMPLE X

The Effect of Humanin on Bak

This example shows Humanin does not affect apoptosis induced by Bak.

Since Humanin co-immunoprecipitates with Bax but not Bak, the effects of Humanin over-expression on apoptosis induced by these members of the Bcl-2 family was compared. As shown in FIG. 6F, when GFP-HN was co-expressed with plasmids encoding Bax or Bak by transient transfection into a CSM14.1 or human prostate cancer PC-3 cells, apoptosis induced by Bax was suppressed by about half, while Bak-induced apoptosis was not affected. Similar results were obtained regardless of whether Humanin was fused to the N- or C-terminus of GFP, with both of these GFP fusion polypeptides localizing to the cytosol of cells. In contrast to GFP-HN, expression of GFP control protein and non-Bax-binding GFP-HN(C8P) mutant protein did not suppress Bax-induced apoptosis, demonstrating the specificity of these results (FIG. 6F). Immunoblot analysis was used to demonstrate production of all plasmid-derived polypeptides.

EXAMPLE XI

Effect of Humanin in Bax-expressing and Bax-deficient Cells

This example shows the effect of Humanin in Bax-expressing and Bax-deficient human cells and in yeast cells which do not express Bax.

For these experiments, HCT116 colon cancer cells, which contain one intact and one mutant Bax allele, were used as well as a mutant of HCT116 (gift of B. Vogelstein) in which the remaining Bax allele was disrupted by homologous recombination, producing Bax-deficient cells (Zhange et al., *Science* 290:989-992 (2000)). In contrast to their differences in Bax expression, these cell lines both express comparable amounts of Bid (FIG. 6G) as well as several other Bcl-2 family proteins. The broad-spectrum kinase inhibitor, Staurosporine (STS), induces apoptosis through a mechanism involving translocation of Bax to mitochondria and release of cytochrome c (Korsmeyer et al., *Cell Death & Differ.* 7:1166-1173 (2000)). As shown in FIG. 6G, when apoptosis was induced by STS in HCT116 parental cells, GFP-HN reduced the percentage of cells undergoing apoptosis by about half. In contrast, GFP-HN failed to suppress apoptosis in Bax-deficient HCT116 cells. Based on previous studies using cells from gene knock-out mice that have shown either Bax or Bak is sufficient for STS-induced apoptosis, a reason that Humanin only partially suppresses apoptosis in these cells can be because it does not interfere with Bak.

Furthermore, the effects of Humanin in yeast (*S. cerevisiae*) was tested since these cells provide a heterologous system lacking endogenous Bcl-2 family proteins that might complicate interpretation of data. In yeast, ectopic expression of Bax induces cell death through a mechanism similar to mammalian cells (reviewed in Jin and Reed, *Nature Rev. Mol. Cell Biol.* 3:453-459 (2002)). For these experiments, Bax was expressed under a GAL10-promoter, which permits conditional expression, so that Bax is produced when yeast are plated on galactose-containing, but not glucose-containing medium (Xu et al., Methods in Enzymology 283-296 (Academic Press, San Diego, )2000)). As shown in FIG. 2H, coexpression of wild-type Humanin polypeptide, expressed as a TAD-fusion polypeptide, rescued yeast from Bax-induced lethality, while the Humanin (C8P) mutant did not rescue yeast from Bax-induced lethality. Immunoblot analysis demonstrated that both TAD-tagged wild-type Humanin and Humanin (C8P) mutant polypeptides were produced at comparable levels in yeast, excluding differences in expression as a trivial explanation for the findings.

EXAMPLE XII

Humanin Suppresses Bax Translocation to Mitochondria

This example shows suppression of Bax translocation to mitochondria by Humanin.

Figure 7:
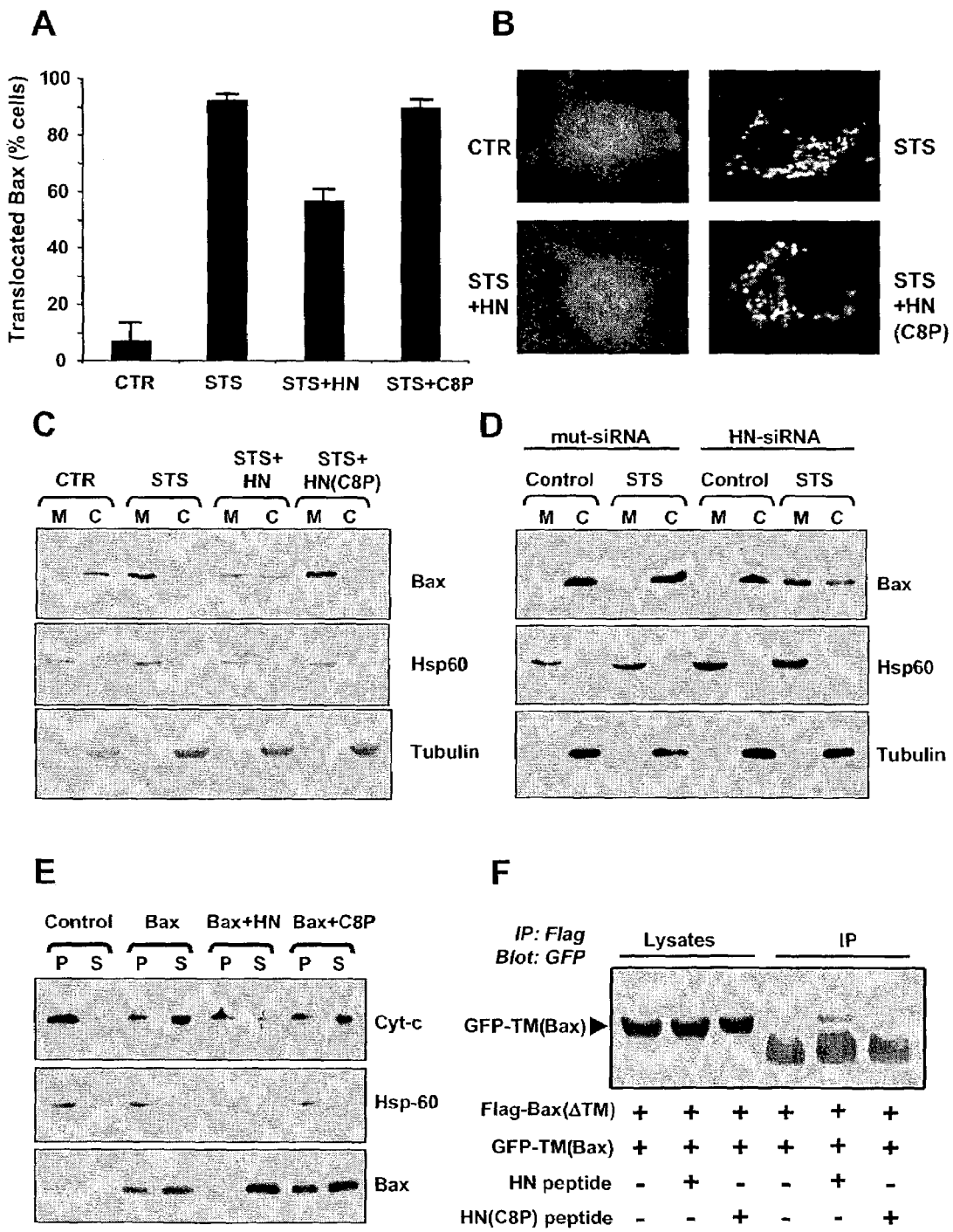
FIG. 7 shows that Humanin can block Bax translocation to mitochondria. (A-B) Humanin peptide prevents STS-induced Bax translocation in vivo. Cos-7 cells were first transfected with GFP-Bax plasmids. After 24 hrs, untagged wild-type or C8P mutant Humanin peptides were introduced into cells using ChariotTM reagent, and 2 h later cells were treated with 1 μM STS. After 4 h, the percentage of cells with translocated Bax was determined (mean±SD; n=3) by confocal microscopy (A) and representative photomicrographs (B). (C) Wild-type or C8P mutant Humanin peptides were introduced into Cos7 cells using ChariotTM reagent. Cytosolic (C) and mitochondria-containing (M) fractions were isolated by differential centrifugation 23 and analyzed by immunoblotting using anti-Bax (top), Hsp60 (middle) (mitochondrial marker), or Tubulin (bottom) (cytosol marker) antibodies. (D) HN or mutant control double-strand siRNAs were transfected into SF268 cells. After 48 h, cells were cultured without (Control) or with 0.1 uM STS. After 24 hr, cells were fractionated and analyzed by immunoblotting as above. (E) Isolated mitochondria were mixed with 400 ng Bax protein, with or without preincubating Bax with 100 uM Humanin or Humanin (C8P) peptides for 10 min. After 3 h at 30° C., mitochondria were centrifuged and the resulting pellets (P) and supernatants (S) were analyzed by immunoblotting using anti-Cytochrome c (top), Hsp60 (middle), and Bax (bottom) antibodies. (F) HN peptide enforces the interaction of Bax TM domain with Bax.TM. Lysates from HEK293T cells expressing Flag-Bax.TM were pretreated with or without Humanin or Humanin(C8P) peptides. Lysates were then mixed in vitro with lysates of HEK293T cells expressing GFP-TM(Bax). Immunoprecipitations were performed with anti-Flag antibody, analyzing lysates and immunoprecipitates (IP) by immunoblotting using monoclonal anti-GFP antibody.

To explore the mechanism by which Humanin suppresses apoptosis induced by Bax, the effects of Humanin over-expression on STS-induced translocation of GFP-Bax polypeptide from cytosol to mitochondria in Cos7 cells was examined. Cos7 cells are a cell model used previously for studies of the Bax translocation phenomenon (Wolter et al., *J. Cell Biol.* 139:1281-1292 (1997); Nechushtan et al., *EMBO Journal* 18:2330-2341 (1999); Nouraini et al., *Mol. Cell Biol.* 20:1604-1615 (2000)). For these experiments, synthetic Humanin or Humanin (C8P) peptides were introduced into cells using a reagent optimized for polypeptide delivery. Confocal UV-microscopy was used to monitor translocation of GFP-Bax to punctate cytosolic structures previously documented to represent mitochondria (Wolter et al, supra (1997); Nechushtan et al., supra (1999); Nouraini et al., supra (2000)), counting the percentage of cells in which cytosolic fluorescence was diffuse versus punctate. Confocal microscopy was performed as described (Nouraini et al., supra (2000); Guo et al., *J. Biol. Chem.* 276:2780-2785 (2001)). As shown in FIG. 7A and 7B, treatment of GFP-Bax-expressing Cos7 cells with STS induced mitochondrial translocation of GFP-Bax in most of the cells expressing this polypeptide. In contrast, GFP-Bax translocation was suppressed by about half in cells transduced with Humanin but not Humanin(C8P) peptide.

These findings were also confirmed by subcellular fractionation, where cytosol and mitochondria-enriched heavy membrane preparations were prepared from Cos7 cells transduced with untagged Humanin or Humanin(C8P) peptides, and the relative amounts of endogenous Bax protein in these two fractions were measured by immunoblot analysis of samples normalized for cell-equivalents. As shown in FIG. 7C, Bax protein was located primarily in the cytosol of unstimulated cells, but was predominantly membrane associated after STS treatment. Transduction of Humanin peptide reduced Bax translocation, while Humanin(C8P) had no effect. Conversely, when Humanin expression was knocked-down by siRNA in SF268 cells, which contain high endogenous levels of Humanin (FIG. 6E), then STS-induced translocation of Bax to membranes was enhanced (FIG. 7D). Incubating the same blots with antibodies to mitochondrial protein Hsp60 and cytosolic β-Tubulin verified proper fractionation and protein loading in these experiments (FIG. 7C and 7D). Therefore, Humanin can suppress translocation of Bax to mitochondria. Differences in the relative potency of Humanin at blocking Bax translocation as measured by microscopy (FIG. 7A) versus cell fractionation methods (FIG. 7C) can be explained by differences in the sensitivity of the assays, or could possibly indicate that even in cells where some Bax translocation has occurred, less of the total Bax protein associated with mitochondria.

To determine whether Humanin can act directly on Bax, the effects of Humanin on isolated mitochondria were tested. Addition of recombinant purified Bax protein to mitochondria in vitro induces cytochrome c release (Jurgensmeier et al., *Proc. Natl. Acad. Sci. USA* 95:4997-5002 (1998)). As shown in FIG. 7E, preincubating Bax with wild-type Humanin peptide suppressed Bax association with mitochondria and reduced cytochrome c release. In contrast, the non-Bax-binding Humanin(C8P) mutant peptide did not interfere with Bax effects on isolated mitochondria. Therefore Humanin can directly suppress Bax targeting to mitochondria, without requirement for intact cells.

Peptide transfections were performed as follows. Humanin or C8P peptides were transfected into GFP-Bax transfected Cos-7 cells using Chariot™ reagent (Active Motif, Carlsbad, Calif.). One microgram of peptide was mixed with 6 μl of Chariot reagent in 200 μl water and incubated for 30 minutes. Two hours before STS treatment, GFP-Bax-expressing cells in 6-well plates were washed with PBS and incubated with Chariot-peptide complex in serum-free media at 37° C. for 1 hour. Cells were incubated for an additional hour after 1 ml complete growth media was added. Cells were then treated with STS to induce Bax translocation.

Subcellular fractionation was performed as follows. Cells ($10^7$ cells) were resuspended with 5 volumes of buffer A (20 mM Hepes-KOH, pH 7.5, 10 mM KCl, 1.5 mM MgCl2, 1 mM Na2-EDTA, 1 mM Na2-EGTA, 1 mM dithiothreitoi, and 0.1 mM phenylmethylsulfonylfluoride) containing 250 mM sucrose. Cells were homogenized with 25 strokes of a Teflon homogenizer, and centrifuged two times at 750×g for 10 min at 4° C. Supernatants were centrifuged at 10,000×g for 20 min at 4° C. The resulting mitochondria-containing pellets were washed twice with buffer A, then resuspended in buffer A containing 250 mM sucrose. The supernatants of the 10,000×g spin were further centrifuged at 100,000×g for 1 h at 4° C. to produce cytosol.

Cytochrome c release assays were performed as follows. Mitochondria were isolated from HCT116 cells by differential centrifugation as described above. Purified recombinant human Bax protein (400 ng for each sample) was pre-incubated with or without 100 μM synthetic Humanin peptide or mutant Humanin (C8P) peptide for 10 min at 4° C. The untreated or peptide pre-treated Baxprotein samples were then mixed with equal amount of HCT116 mitochondria (in a volume of 40 μl) at 30° C. for 3 hours. Samples were then centrifuged at 10,000 g for 20 min to obtain pellet (P) and supernatant (S) fractions, measuring cytochrome c by immunoblotting.

EXAMPLE XIII

Humanin Can Stabilize the Latent Conformation of Bax

This example shows Humanin can stabilize the latent conformation of Bax (previously delineated by solution NMR), in which its C-terminal tail is docked onto a hydrophobic crevice on the surface of the Bax molecule.

Solution NMR and antibody-based epitope mapping studies suggest that the mechanism of conversion of Bax from latent to active form involves the dislodging of a C-terminal hydrophobic α-helix (transmembrane [TM]domain) from the body of the Bax protein, exposing this membrane-anchoring TM domain for insertion into mitochondrial membranes (Suzuki et al., *Cell* 103:645-654 (2000)). To test the effects of Humanin on the interaction of the TM domain of Bax with the rest of the Bax protein, a C-terminally truncated Bax protein (residues 1-169) (BaxΔTM) and a GFP-fusion containing the C-terminal TM domain of Bax (residues 170-192) were separately produced. The BaxΔTM protein was pre-incubated with Humanin or control peptide, then mixed with GFP-TM, testing for interaction by co-immunoprecipitation assay. As shown in FIG. 7F, in the absence of Humanin, no binding of GFP-TM to BaxΔTM was detected. In contrast, when Humanin was added, BaxΔTM was immunoprecipitated with GFP-TM. Humanin (C8P) peptide did not promote interaction of BaxΔTM with GFP-TM, demonstrating the specificity of these results. Thus, Humanin can stabilize the latent conformation of Bax (previously delineated by solution NMR), in which its C-terminal tail is docked onto a hydrophobic crevice on the surface of the Bax molecule.

EXAMPLE XIV

Nuclear and Mitochondria Encoded Humanin Can Bind Bax

This example shows both the nuclear and mitochondrial encoded Humanin can bind Bax and suppress Bax-induced apoptosis.

Figure 8:
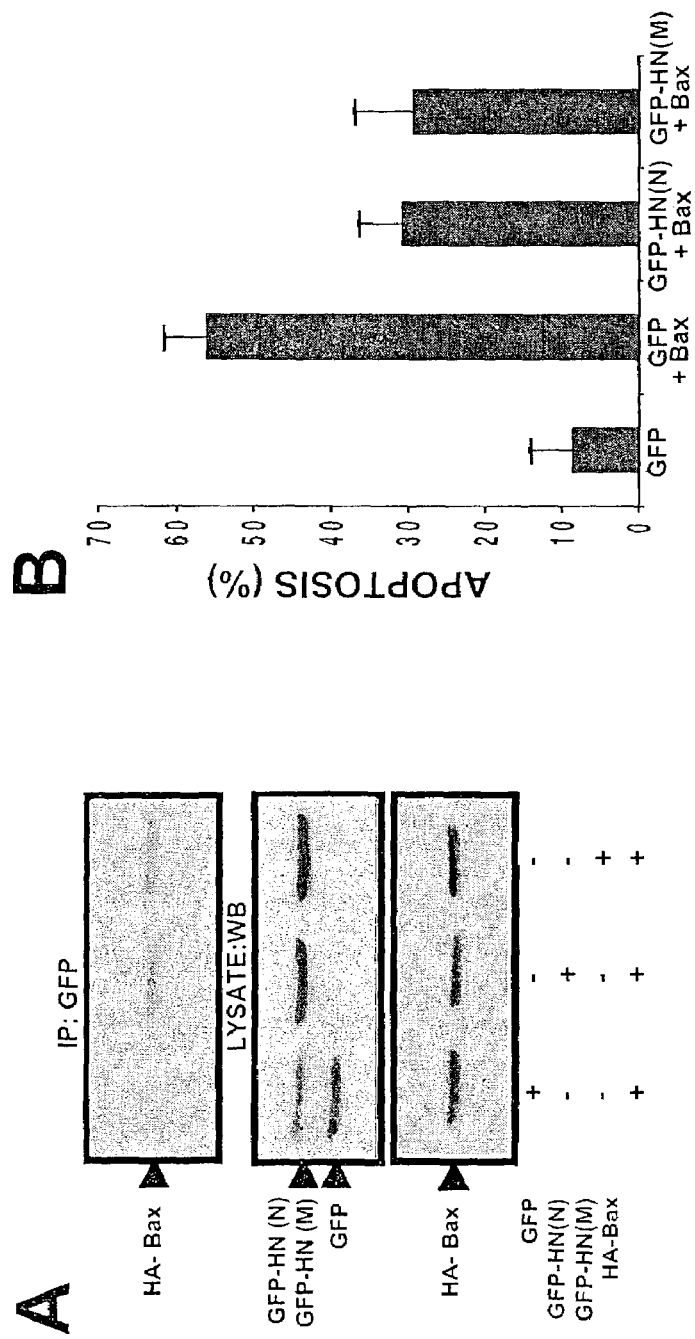
FIG. 8 shows a comparison of nuclear (N)- and mitochondria (M)-encoded HN. (A) HEK293T cells were transfected with pcDNA3-HA-Bax together with plasmids encoding GFP, GFP-HN(N), or GFP-HN(M). Cell lysates were immunoprecipitated with polyclonal anti-GFP antibody. Immunoprecipitates (IP) or cell lysates were analyzed by immunoblotting using anti-HA or anti-GFP antibodies, respectively. (B) CSM14.1 neuronal cells were co-transfected with pcDNA3-HA-Bax together with plasmids encoding GFP, GFP-HN(N), or GFP-HN(M). Percent apoptosis was determined 48 h later by DAPI staining (mean±SD; n=3).

As shown in Example IV and FIG. 3, during analysis of Humanin-encoding sequences in the human genome, an identical open reading frame embedded in the 16S rRNA gene of the mammalian mitocondria genome was discovered. Differences in codon usage by the endogenous protein translation machinery of mitochondria would be predicted to result in a slightly different Humanin polypeptide (SEQ ID NO:3). To investigate the ability of the predicted nuclear-encoded and mitochondria-encoded Humanin peptides [termed HN(N) and HN(M), respectively] to bind Bax and to suppress apoptosis induced by over-expression of Bax, HN(N) and HN(M) were expressed as GFP fusion polypeptides. As shown in FIG. 8A, comparable amounts of Bax co-immunoprecipitated with both GFP-HN(N) and GFP-HN(M). As shown in FIG. 8B, Bax-induced apoptosis was also suppressed to comparable extents by both GFP-HN(N) and GFP-HN(M). Thus, the nuclear and the mitochondrial translations of the Humanin ORF are capable of binding and suppressing Bax.

All journal article, reference and patent citations provided above, including referenced sequence accession numbers of nucleotide and amino acid sequences contained in various databases, in parentheses or otherwise, whether previously stated or not, are incorporated herein by reference in their entirety.

Although the invention has been described with reference to the disclosed embodiments, those skilled in the art will readily appreciate that the specific experiments detailed are only illustrative of the invention. It should be understood that various modifications can be made without departing from that spirit of the invention.

Summary of Nucleotide and Amino Acid Sequences

Sequence ID NO. 1 is a nucleotide sequence of a cytosolic form of human Humanin.

Sequence ID NO. 2 is an amino acid sequence of a cytosolic form of human Humanin.

Sequence ID NO. 3 is an amino acid sequence of a mitochondrial-derived form of human Humanin.

Sequence ID NO. 4 is a nucleotide sequence of a human Bax.

Sequence ID NO. 5 is an amino acid sequence of human Bax.

Sequence ID NO. 6 is a nucleotide sequence of human Bid.

Sequence ID NO. 7 is an amino acid sequence of human Bid.

Sequence ID NO. 8 is a nucleotide sequence of human truncated Bid (t-Bid).

Sequence ID NO. 9 is an amino acid sequence of human truncated Bid (t-Bid).

Sequence ID NO. 10 is an amino acid sequence derived from SV40 T Antigen.

Sequence ID NO. 11 is an amino acid sequence of a brain homing polypeptide.

Sequence ID NO. 12 is an amino acid sequence of a brain homing polypeptide.

Sequence ID NO. 13 is a nucleotide sequence of a NADH oligonucleotide forward primer.

Sequence ID NO. 14 is a nucleotide sequence of a NADH oligonucleotide reverse primer.

Sequence ID NO. 15 is a nucleotide sequence of a COX oligonucleotide forward primer.

Sequence ID NO. 16 is a nucleotide sequence of a COX oligonucleotide reverse primer.

Sequence ID NO. 17 is a nucleotide sequence of a Humanin oligonucleotide forward primer.

Sequence ID NO. 18 is a nucleotide sequence of a Humanin oligonucleotide reverse primer.

Sequence ID NO. 19 is a nucleotide sequence of a Bax oligonucleotide forward primer.

Sequence ID NO. 20 is a nucleotide sequence of a Bax oligonucleotide reverse primer.

Sequence ID NO. 21 is a nucleotide sequence of a mitochondrial derived Humanin oligonucleotide forward primer.

Sequence ID NO. 22 is a nucleotide sequence of a mitochondrial derived Humanin oligonucleotide reverse primer.

Sequence ID NO. 23 is a nucleotide sequence of a C8A Humanin oligonucleotide forward primer.

Sequence ID NO. 24 is a nucleotide sequence of a C8A Humanin oligonucleotide reverse primer.

Sequence ID NO. 25 is a small interfering RNA sequence of the sense strand of Humanin.

Sequence ID NO. 26 is a small interfering RNA sequence of the anti-sense strand of Humanin.

Sequence ID NO. 27 is a small interfering RNA sequence of the sense strand of a mutant Humanin.

Sequence ID NO. 28 is a small interfering RNA sequence of the anti-sense strand of a mutant Humanin.

We claim:

1. A method of identifying an effective compound that decreases the binding of Humanin to Bax, comprising the steps of:

(a) contacting said Humanin, wherein Humanin comprises the amino acid sequence SEQ ID NO:2 or SEQ ID NO:3, with said Bax, wherein Bax comprises the amino acid sequence SEQ ID NO:5, in vitro under conditions suitable to form a Humanin-Bax complex;

(b) contacting said Humanin-Bax complex with a candidate compound; and (c) determining the ability of said candidate compound to decrease the binding of said Humanin to said Bax, wherein decreasing the binding of said Humanin to said Bax indicates that said candidate compound is an effective compound that decreases the binding of said Humanin to said Bax.

2. The method of claim 1, wherein said candidate compound is selected from the group consisting of: a polypeptide, peptidomimetic, non-peptidyl compound, carbohydrate, lipid, a synthetic compound, a natural product, an antibody or antibody fragment, a small organic molecules, a small inorganic molecule, and a nucleotide sequence.

3. The method of claim 1, wherein said candidate compound is a small organic molecule.

4. The method of claim 1, wherein said candidate compound is a polypeptide.

5. The method of claim 1, wherein said binding is determined using a method selected from the group consisting of: a co-immunoprecipitation assay, scintillation proximity assay (SPA), UV or chemical cross-linking, biomolecular interaction analysis (BIA), mass spectrometry (MS), nuclear magnetic resonance (NMR), and fluorescence polarization assays (FPA).

6. A method of identifying an effective compound that decreases the binding of Humanin to Bax, comprising the steps of:
  (a) contacting said Humanin, wherein Humanin comprises the amino acid sequence SEQ ID NO:2 or SEQ ID NO:3, with said Bax, wherein Bax comprises the amino acid sequence SEQ ID NO:5, under conditions suitable to form a Humanin-Bax complex in a yeast two-hybrid assay;
  (b) contacting said Humanin-Bax complex with a candidate compound; and
  (c) determining the ability of said candidate compound to decrease the binding of said Humanin to said Bax, wherein decreasing the binding of said Humanin to said Bax indicates that said candidate compound is an effective compound that decreases the binding of said Humanin to said Bax.

7. The method of claim 6, wherein said candidate compound is selected from the group consisting of: a polypeptide, peptidomimetic, non-peptidyl compound, carbohydrate, lipid, a synthetic compound, a natural product, an antibody or antibody fragment, a small organic molecules, a small inorganic molecule, and a nucleotide sequence.

8. The method of claim 6, wherein said candidate compound is a small organic molecule.

9. The method of claim 6, wherein said candidate compound is a polypeptide.

10. The method of claim 1, wherein Humanin comprises the amino acid sequence SEQ ID NO:2.

11. The method of claim 1, wherein Humanin comprises the amino acid sequence SEQ ID NO:3.

12. The method of claim 6, wherein Humanin comprises the amino acid sequence SEQ ID NO:2.

13. The method of claim 6, wherein Humanin comprises the amino acid sequence SEQ ID NO:3.

* * * * *